US012569336B2

(12) United States Patent
Ottma et al.

(10) Patent No.: US 12,569,336 B2
(45) Date of Patent: Mar. 10, 2026

(54) CATHETER SYSTEM FOR IMPLANTATION OF PROSTHETIC HEART VALVES

(71) Applicant: JenaValve Technology, Inc., Irvine, CA (US)

(72) Inventors: Rudiger Ottma, GroBschwabhausen (DE); Robert Moszner, Bad Klosterlausnitz (DE); Hans-Reiner Figulla, Jena (DE); Markus Ferrari, Jena (DE); Christoph Damm, Jena (DE)

(73) Assignee: JenaValve Technology, Inc., Irvine, CA (US)

( * ) Notice: Subject to any disclaimer, the term of this patent is extended or adjusted under 35 U.S.C. 154(b) by 622 days.

(21) Appl. No.: 18/061,853

(22) Filed: Dec. 5, 2022

(65) Prior Publication Data

US 2023/0100094 A1 Mar. 30, 2023

Related U.S. Application Data

(63) Continuation of application No. 16/665,502, filed on Oct. 28, 2019, now Pat. No. 11,517,431, which is a
(Continued)

(51) Int. Cl.
| | |
|---|---|
| *A61F 2/24* | (2006.01) |
| *A61F 2/95* | (2013.01) |

(52) U.S. Cl.
CPC .......... *A61F 2/2427* (2013.01); *A61F 2/2418* (2013.01); *A61F 2/2436* (2013.01); *A61F 2/9517* (2020.05); *A61F 2240/008* (2013.01)

(58) Field of Classification Search
CPC .................................................. A61F 2/2436
See application file for complete search history.

(56) References Cited

U.S. PATENT DOCUMENTS

| | | | |
|---|---|---|---|
| 15,192 | A | 6/1856 | Peale |
| 388,776 | A | 8/1888 | Hall |

(Continued)

FOREIGN PATENT DOCUMENTS

| | | |
|---|---|---|
| AU | 757647 B2 | 2/2003 |
| AU | 776895 B2 | 9/2004 |

(Continued)

OTHER PUBLICATIONS

US 6,331,185 B1, 12/2001, Gambale et al. (withdrawn)
(Continued)

*Primary Examiner* — Jacqueline Woznicki
(74) *Attorney, Agent, or Firm* — Greenberg Traurig, LLP; Christopher C. Bolten; Robert D. Ward

(57) ABSTRACT

The invention relates to a catheter for the transvascular implantation of prosthetic heart valves, in particular including self-expanding anchorage supports (10), which allow a minimally invasive implantation of prosthetic heart valves. The aim of the invention is to reduce the risk to the patient during the implantation. To achieve this, according to the invention a prosthetic heart valve with anchorage supports is temporarily housed in a folded form in a cartridge-type unit (4) during the implantation. The cartridge-type unit can be fixed on the proximal end of a guide system (1), which includes a flexible region (9) that can be guided through the aorta. Actuating elements (2, 3) run through the interior of the hollow guide system, said elements permitting sections of the cartridge-type unit to be displaced radially about their longitudinal axis and/or laterally in a proximal direction, thus allowing individual sections of the anchorage support and the associated prosthetic heart valve to be sequentially released.

20 Claims, 6 Drawing Sheets

Related U.S. Application Data continuation of application No. 15/700,366, filed on Sep. 11, 2017, now Pat. No. 10,492,906, which is a continuation of application No. 15/464,891, filed on Mar. 21, 2017, now Pat. No. 9,788,945, which is a continuation of application No. 14/168,976, filed on Jan. 30, 2014, now Pat. No. 9,775,705, which is a continuation of application No. 11/795,590, filed as application No. PCT/DE2006/000056 on Jan. 12, 2006, now Pat. No. 8,679,174.

(56) References Cited

U.S. PATENT DOCUMENTS

| | | |
|---|---|---|
| 944,214 A | 12/1909 | Rydquist |
| 2,121,182 A | 6/1938 | Benjamin |
| 2,669,896 A | 2/1954 | Clough |
| 2,682,057 A | 6/1954 | Lord |
| 2,701,559 A | 2/1955 | Cooper |
| 2,832,078 A | 4/1958 | Williams |
| 3,029,819 A | 4/1962 | Edward et al. |
| 3,099,016 A | 7/1963 | Lowell et al. |
| 3,113,586 A | 12/1963 | Edmark, Jr. et al. |
| 3,130,418 A | 4/1964 | Head et al. |
| 3,143,742 A | 8/1964 | Cromie |
| 3,210,836 A | 10/1965 | Johanson et al. |
| 3,221,006 A | 11/1965 | Moore et al. |
| 3,334,629 A | 8/1967 | Cohn |
| 3,365,728 A | 1/1968 | Lowell et al. |
| 3,367,364 A | 2/1968 | Cruz, Jr. et al. |
| 3,409,013 A | 11/1968 | Henry et al. |
| 3,445,916 A | 5/1969 | Schulte et al. |
| 3,540,431 A | 11/1970 | Mobin-Uddin et al. |
| 3,548,417 A | 12/1970 | Kischer et al. |
| 3,570,014 A | 3/1971 | Hancock et al. |
| 3,574,865 A | 4/1971 | Hamaker |
| 3,587,115 A | 6/1971 | Shiley et al. |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,078,268 A | 3/1978 | Possis |
| 4,084,268 A | 4/1978 | Ionescu et al. |
| 4,106,126 A | 8/1978 | Traenkle |
| 4,106,129 A | 8/1978 | Carpentier et al. |
| 4,118,806 A | 10/1978 | Porier et al. |
| 4,164,046 A | 8/1979 | Cooley |
| 4,182,446 A | 1/1980 | Penny |
| 4,191,218 A | 3/1980 | Clark et al. |
| 4,214,587 A | 7/1980 | Sakura, Jr. |
| 4,215,871 A | 8/1980 | Hirsch et al. |
| 4,222,126 A | 9/1980 | Boretos et al. |
| 4,233,690 A | 11/1980 | Akins |
| 4,261,342 A | 4/1981 | Aranguren Duo |
| 4,263,680 A | 4/1981 | Reul et al. |
| 4,265,694 A | 5/1981 | Boretos et al. |
| 4,291,420 A | 9/1981 | Reul |
| 4,297,749 A | 11/1981 | Davis et al. |
| 4,319,831 A | 3/1982 | Matsui et al. |
| RE30,912 E | 4/1982 | Hancock |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,350,492 A | 9/1982 | Wright et al. |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,441,215 A | 4/1984 | Kaster |
| 4,441,216 A | 4/1984 | Ionescu et al. |
| 4,470,157 A | 9/1984 | Love |
| 4,484,579 A | 11/1984 | Meno et al. |
| 4,485,816 A | 12/1984 | Krumme |
| 4,491,986 A | 1/1985 | Gabbay |
| 4,501,030 A | 2/1985 | Lane |
| 4,502,488 A | 3/1985 | Degironimo et al. |
| 4,531,943 A | 7/1985 | Van Tassel et al. |
| 4,535,483 A | 8/1985 | Klawitter et al. |
| 4,546,499 A | 10/1985 | Possis et al. |
| 4,562,597 A | 1/1986 | Possis et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,619,246 A | 10/1986 | Molgaard-Nielsen et al. |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,665,918 A | 5/1987 | Garza et al. |
| 4,680,031 A | 7/1987 | Alonso |
| 4,681,908 A | 7/1987 | Broderick et al. |
| 4,687,483 A | 8/1987 | Fisher et al. |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,769,029 A | 9/1988 | Patel |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,806,595 A | 2/1989 | Noishiki et al. |
| 4,819,751 A | 4/1989 | Shimada et al. |
| 4,829,990 A | 5/1989 | Thuroff et al. |
| 4,834,755 A | 5/1989 | Silvestrini et al. |
| 4,846,830 A | 7/1989 | Knoch et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,950,227 A | 8/1990 | Savin et al. |
| 4,953,553 A | 9/1990 | Tremulis |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |

(56) References Cited

U.S. PATENT DOCUMENTS

| | | | |
|---|---|---|---|
| 5,002,559 A | 3/1991 | Tower |
| 5,002,566 A | 3/1991 | Carpentier et al. |
| 5,007,896 A | 4/1991 | Shiber |
| 5,026,366 A | 6/1991 | Leckrone |
| 5,026,377 A | 6/1991 | Burton et al. |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,053,008 A | 10/1991 | Bajaj |
| 5,059,177 A | 10/1991 | Towne et al. |
| 5,061,273 A | 10/1991 | Yock |
| 5,061,277 A | 10/1991 | Carpentier et al. |
| 5,064,435 A | 11/1991 | Porter |
| 5,078,720 A | 1/1992 | Burton et al. |
| 5,080,668 A | 1/1992 | Bolz et al. |
| 5,085,635 A | 2/1992 | Cragg |
| 5,089,015 A | 2/1992 | Ross |
| 5,094,661 A | 3/1992 | Levy et al. |
| 5,104,399 A | 4/1992 | Lazarus |
| 5,104,407 A | 4/1992 | Lam et al. |
| 5,108,425 A | 4/1992 | Hwang |
| 5,122,154 A | 6/1992 | Rhodes |
| 5,132,473 A | 7/1992 | Furutaka et al. |
| 5,141,494 A | 8/1992 | Danforth et al. |
| 5,143,987 A | 9/1992 | Hansel et al. |
| 5,147,388 A | 9/1992 | Yamazaki |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,178,632 A | 1/1993 | Hanson |
| 5,192,301 A | 3/1993 | Kamiya et al. |
| 5,193,546 A | 3/1993 | Shaknovich |
| 5,197,979 A | 3/1993 | Quintero et al. |
| 5,201,757 A | 4/1993 | Heyn et al. |
| 5,207,695 A | 5/1993 | Trout, III |
| 5,209,741 A | 5/1993 | Spaeth |
| 5,211,183 A | 5/1993 | Wilson |
| 5,215,541 A | 6/1993 | Nashef et al. |
| 5,217,481 A | 6/1993 | Barbara |
| 5,217,483 A | 6/1993 | Tower |
| 5,232,445 A | 8/1993 | Bonzel |
| 5,234,447 A | 8/1993 | Kaster et al. |
| 5,234,456 A | 8/1993 | Silvestrini |
| 5,238,004 A | 8/1993 | Sahatjian et al. |
| 5,258,008 A | 11/1993 | Wilk |
| 5,258,023 A | 11/1993 | Reger |
| 5,258,042 A | 11/1993 | Mehta |
| 5,272,909 A | 12/1993 | Nguyen et al. |
| 5,275,580 A | 1/1994 | Yamazaki |
| 5,279,612 A | 1/1994 | Eberhardt |
| 5,282,847 A | 2/1994 | Trescony et al. |
| 5,287,861 A | 2/1994 | Wilk |
| 5,295,958 A | 3/1994 | Shturman |
| 5,327,774 A | 7/1994 | Nguyen et al. |
| 5,330,486 A | 7/1994 | Wilk |
| 5,330,500 A | 7/1994 | Song |
| 5,332,402 A | 7/1994 | Teitelbaum |
| 5,336,258 A | 8/1994 | Quintero et al. |
| 5,342,348 A | 8/1994 | Kaplan |
| 5,344,426 A | 9/1994 | Lau et al. |
| 5,344,427 A | 9/1994 | Cottenceau et al. |
| 5,344,442 A | 9/1994 | Deac |
| 5,350,398 A | 9/1994 | Pavcnik et al. |
| 5,350,399 A | 9/1994 | Erlebacher et al. |
| 5,352,240 A | 10/1994 | Ross |
| 5,354,330 A | 10/1994 | Hanson et al. |
| 5,360,444 A | 11/1994 | Kusuhara |
| 5,368,608 A | 11/1994 | Levy et al. |
| 5,370,685 A | 12/1994 | Stevens |
| 5,380,054 A | 1/1995 | Galvis |
| 5,387,235 A | 2/1995 | Chuter |
| 5,389,096 A | 2/1995 | Aita et al. |
| 5,389,106 A | 2/1995 | Tower |
| 5,397,351 A | 3/1995 | Pavcnik et al. |
| 5,397,355 A | 3/1995 | Marin et al. |
| 5,409,019 A | 4/1995 | Wilk |
| 5,411,552 A | 5/1995 | Andersen et al. |
| 5,415,633 A | 5/1995 | Lazarus et al. |
| 5,425,739 A | 6/1995 | Jessen |
| 5,425,762 A | 6/1995 | Muller |
| 5,429,144 A | 7/1995 | Wilk |
| 5,431,676 A | 7/1995 | Dubrul et al. |
| 5,433,723 A | 7/1995 | Lindenberg et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,449,384 A | 9/1995 | Johnson |
| 5,456,712 A | 10/1995 | Maginot |
| 5,456,713 A | 10/1995 | Chuter |
| 5,464,449 A | 11/1995 | Ryan et al. |
| 5,469,868 A | 11/1995 | Reger |
| 5,470,320 A | 11/1995 | Tiefenbrun et al. |
| 5,476,506 A | 12/1995 | Lunn |
| 5,476,508 A | 12/1995 | Amstrup |
| 5,476,510 A | 12/1995 | Eberhardt et al. |
| 5,480,423 A | 1/1996 | Ravenscroft et al. |
| 5,480,424 A | 1/1996 | Cox |
| 5,486,193 A | 1/1996 | Bourne et al. |
| 5,487,760 A | 1/1996 | Villafana |
| 5,489,294 A | 2/1996 | McVenes et al. |
| 5,489,297 A | 2/1996 | Duran |
| 5,489,298 A | 2/1996 | Love et al. |
| 5,496,346 A | 3/1996 | Horzewski et al. |
| 5,499,995 A | 3/1996 | Teirstein |
| 5,500,014 A | 3/1996 | Quijano et al. |
| 5,500,015 A | 3/1996 | Deac |
| 5,507,767 A | 4/1996 | Maeda et al. |
| 5,509,930 A | 4/1996 | Love |
| 5,522,881 A | 6/1996 | Lentz |
| 5,527,337 A | 6/1996 | Stack et al. |
| 5,530,949 A | 6/1996 | Koda et al. |
| 5,534,007 A | 7/1996 | St. Germain et al. |
| 5,540,712 A | 7/1996 | Kleshinski et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,549,666 A | 8/1996 | Hata et al. |
| 5,554,119 A | 9/1996 | Harrison et al. |
| 5,554,185 A | 9/1996 | Block et al. |
| 5,569,274 A | 10/1996 | Rapacki et al. |
| 5,571,167 A | 11/1996 | Maginot |
| 5,571,174 A | 11/1996 | Love et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,580,922 A | 12/1996 | Park et al. |
| 5,591,185 A | 1/1997 | Kilmer et al. |
| 5,591,195 A | 1/1997 | Taheri et al. |
| 5,593,434 A | 1/1997 | Williams |
| 5,595,571 A | 1/1997 | Jaffe et al. |
| 5,596,471 A | 1/1997 | Hanlin |
| 5,607,464 A | 3/1997 | Trescony et al. |
| 5,607,465 A | 3/1997 | Camilli |
| 5,609,626 A | 3/1997 | Quijano et al. |
| 5,613,982 A | 3/1997 | Goldstein |
| 5,618,299 A | 4/1997 | Khosravi et al. |
| 5,626,553 A | 5/1997 | Frassica et al. |
| 5,628,784 A | 5/1997 | Strecker |
| 5,632,778 A | 5/1997 | Goldstein |
| 5,634,942 A | 6/1997 | Chevillon et al. |
| 5,643,278 A | 7/1997 | Wijay |
| 5,645,559 A | 7/1997 | Hachtman et al. |
| 5,653,684 A | 8/1997 | Laptewicz et al. |
| 5,653,745 A | 8/1997 | Trescony et al. |
| 5,653,749 A | 8/1997 | Love et al. |

(56) References Cited

U.S. PATENT DOCUMENTS

| | | | |
|---|---|---|---|
| 5,655,548 A | 8/1997 | Nelson et al. |
| 5,662,124 A | 9/1997 | Wilk |
| 5,662,671 A | 9/1997 | Barbut et al. |
| 5,662,703 A | 9/1997 | Yurek et al. |
| 5,665,115 A | 9/1997 | Cragg |
| 5,667,523 A | 9/1997 | Bynon et al. |
| 5,674,277 A | 10/1997 | Freitag |
| 5,674,298 A | 10/1997 | Levy et al. |
| 5,679,112 A | 10/1997 | Levy et al. |
| 5,681,345 A | 10/1997 | Euteneuer |
| 5,682,906 A | 11/1997 | Sterman et al. |
| 5,683,451 A | 11/1997 | Lenker et al. |
| 5,690,644 A | 11/1997 | Yurek et al. |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,697,972 A | 12/1997 | Kim et al. |
| 5,700,269 A | 12/1997 | Pinchuk et al. |
| 5,702,368 A | 12/1997 | Stevens et al. |
| 5,709,713 A | 1/1998 | Evans et al. |
| 5,713,917 A | 2/1998 | Leonhardt et al. |
| 5,713,950 A | 2/1998 | Cox |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,718,725 A | 2/1998 | Sterman et al. |
| 5,720,391 A | 2/1998 | Dohm et al. |
| 5,720,776 A | 2/1998 | Chuter et al. |
| 5,725,549 A | 3/1998 | Lam |
| 5,725,550 A | 3/1998 | Nadal |
| 5,728,068 A | 3/1998 | Leone et al. |
| 5,728,151 A | 3/1998 | Garrison et al. |
| 5,733,267 A | 3/1998 | Del Toro |
| 5,733,325 A | 3/1998 | Robinson et al. |
| 5,735,842 A | 4/1998 | Krueger et al. |
| 5,746,476 A | 5/1998 | Novak et al. |
| 5,746,709 A | 5/1998 | Rom et al. |
| 5,746,765 A | 5/1998 | Kleshinski et al. |
| 5,746,775 A | 5/1998 | Levy et al. |
| 5,749,890 A | 5/1998 | Shaknovich |
| 5,749,921 A | 5/1998 | Lenker et al. |
| 5,755,682 A | 5/1998 | Knudson et al. |
| 5,755,777 A | 5/1998 | Chuter |
| 5,755,783 A | 5/1998 | Stobie et al. |
| 5,756,476 A | 5/1998 | Epstein et al. |
| 5,758,663 A | 6/1998 | Wilk et al. |
| 5,766,151 A | 6/1998 | Valley et al. |
| 5,769,780 A | 6/1998 | Hata et al. |
| 5,769,812 A | 6/1998 | Stevens et al. |
| 5,769,882 A | 6/1998 | Fogarty et al. |
| 5,769,887 A | 6/1998 | Brown et al. |
| 5,772,609 A | 6/1998 | Nguyen et al. |
| 5,776,188 A | 7/1998 | Shepherd et al. |
| 5,782,809 A | 7/1998 | Umeno et al. |
| 5,782,904 A | 7/1998 | White et al. |
| 5,795,331 A | 8/1998 | Cragg et al. |
| 5,797,946 A | 8/1998 | Chin |
| 5,797,960 A | 8/1998 | Stevens et al. |
| 5,799,661 A | 9/1998 | Boyd et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,327 A | 9/1998 | Green et al. |
| 5,807,384 A | 9/1998 | Mueller |
| 5,807,405 A | 9/1998 | Vanney et al. |
| 5,810,836 A | 9/1998 | Hussein et al. |
| 5,814,016 A | 9/1998 | Valley et al. |
| 5,817,113 A | 10/1998 | Gifford, III et al. |
| 5,817,126 A | 10/1998 | Imran |
| 5,823,956 A | 10/1998 | Roth et al. |
| 5,824,037 A | 10/1998 | Fogarty et al. |
| 5,824,038 A | 10/1998 | Wall |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,063 A | 10/1998 | Cox |
| 5,824,064 A | 10/1998 | Taheri |
| 5,824,071 A | 10/1998 | Nelson et al. |
| 5,824,080 A | 10/1998 | Lamuraglia |
| 5,829,447 A | 11/1998 | Stevens et al. |
| 5,830,222 A | 11/1998 | Makower |
| 5,836,869 A | 11/1998 | Kudo et al. |
| 5,840,081 A | 11/1998 | Andersen et al. |
| 5,841,382 A | 11/1998 | Walden et al. |
| 5,843,158 A | 12/1998 | Lenker et al. |
| 5,843,161 A | 12/1998 | Solovay |
| 5,843,181 A | 12/1998 | Jaffe et al. |
| 5,851,232 A | 12/1998 | Lois |
| 5,853,419 A | 12/1998 | Imran |
| 5,853,420 A | 12/1998 | Chevillon et al. |
| 5,855,210 A | 1/1999 | Sterman et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,865,723 A | 2/1999 | Love |
| 5,868,783 A | 2/1999 | Tower |
| 5,873,812 A | 2/1999 | Ciana et al. |
| 5,873,906 A | 2/1999 | Lau et al. |
| 5,876,373 A | 3/1999 | Giba et al. |
| 5,876,419 A | 3/1999 | Carpenter et al. |
| 5,876,434 A | 3/1999 | Flomenblit et al. |
| 5,876,448 A | 3/1999 | Thompson et al. |
| 5,878,751 A | 3/1999 | Hussein et al. |
| 5,880,242 A | 3/1999 | Hu et al. |
| 5,885,228 A | 3/1999 | Rosenman et al. |
| 5,885,238 A | 3/1999 | Stevens et al. |
| 5,885,259 A | 3/1999 | Berg |
| 5,888,201 A | 3/1999 | Stinson et al. |
| 5,891,160 A | 4/1999 | Williamson, IV et al. |
| 5,891,191 A | 4/1999 | Stinson |
| 5,895,399 A | 4/1999 | Barbut et al. |
| 5,895,420 A | 4/1999 | Mirsch, II et al. |
| 5,899,936 A | 5/1999 | Goldstein |
| 5,906,619 A | 5/1999 | Olson et al. |
| 5,907,893 A | 6/1999 | Zadno-Azizi et al. |
| 5,908,028 A | 6/1999 | Wilk |
| 5,908,029 A | 6/1999 | Knudson et al. |
| 5,908,451 A | 6/1999 | Yeo |
| 5,908,452 A | 6/1999 | Bokros et al. |
| 5,910,144 A | 6/1999 | Hayashi |
| 5,910,154 A | 6/1999 | Tsugita et al. |
| 5,911,734 A | 6/1999 | Tsugita et al. |
| 5,911,752 A | 6/1999 | Dustrude et al. |
| 5,913,842 A | 6/1999 | Boyd et al. |
| 5,916,193 A | 6/1999 | Stevens et al. |
| 5,922,022 A | 7/1999 | Nash et al. |
| 5,924,424 A | 7/1999 | Stevens et al. |
| 5,925,012 A | 7/1999 | Murphy-Chutorian et al. |
| 5,925,063 A | 7/1999 | Khosravi |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,938,697 A | 8/1999 | Killion et al. |
| 5,941,908 A | 8/1999 | Goldsteen et al. |
| 5,944,019 A | 8/1999 | Knudson et al. |
| 5,944,738 A | 8/1999 | Amplatz et al. |
| 5,948,017 A | 9/1999 | Taheri |
| 5,954,764 A | 9/1999 | Parodi |
| 5,954,766 A | 9/1999 | Zadno-Azizi et al. |
| 5,957,949 A | 9/1999 | Leonhardt et al. |
| 5,961,549 A | 10/1999 | Nguyen et al. |

(56) References Cited

U.S. PATENT DOCUMENTS

| | | | |
|---|---|---|---|
| 5,964,405 A | 10/1999 | Benary et al. |
| 5,964,798 A | 10/1999 | Imran |
| 5,968,064 A | 10/1999 | Selmon et al. |
| 5,968,068 A | 10/1999 | Dehdashtian et al. |
| 5,968,070 A | 10/1999 | Bley et al. |
| 5,971,993 A | 10/1999 | Hussein et al. |
| 5,975,949 A | 11/1999 | Holliday et al. |
| 5,976,153 A | 11/1999 | Fischell et al. |
| 5,976,155 A | 11/1999 | Foreman et al. |
| 5,976,174 A | 11/1999 | Ruiz |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,455 A | 11/1999 | Daniel et al. |
| 5,980,533 A | 11/1999 | Holman |
| 5,980,548 A | 11/1999 | Evans et al. |
| 5,984,956 A | 11/1999 | Tweden et al. |
| 5,984,957 A | 11/1999 | Laptewicz, Jr. et al. |
| 5,984,959 A | 11/1999 | Robertson et al. |
| 5,984,964 A | 11/1999 | Roberts et al. |
| 5,987,344 A | 11/1999 | West |
| 5,989,276 A | 11/1999 | Houser et al. |
| 5,989,287 A | 11/1999 | Yang et al. |
| 5,993,469 A | 11/1999 | McKenzie et al. |
| 5,993,481 A | 11/1999 | Marcade et al. |
| 5,997,525 A | 12/1999 | March et al. |
| 5,997,557 A | 12/1999 | Barbut et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 6,010,522 A | 1/2000 | Barbut et al. |
| 6,010,530 A | 1/2000 | Goicoechea |
| 6,010,531 A | 1/2000 | Donlon et al. |
| 6,012,457 A | 1/2000 | Lesh |
| 6,013,854 A | 1/2000 | Moriuchi |
| 6,015,431 A | 1/2000 | Thornton et al. |
| 6,019,777 A | 2/2000 | Mackenzie |
| 6,019,778 A | 2/2000 | Wilson et al. |
| 6,022,370 A | 2/2000 | Tower |
| 6,026,814 A | 2/2000 | LaFontaine et al. |
| 6,027,476 A | 2/2000 | Sterman et al. |
| 6,027,520 A | 2/2000 | Tsugita et al. |
| 6,027,525 A | 2/2000 | Suh et al. |
| 6,029,671 A | 2/2000 | Stevens et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,554 A | 3/2000 | Rosenman et al. |
| 6,042,581 A | 3/2000 | Ryan et al. |
| 6,042,589 A | 3/2000 | Marianne |
| 6,042,598 A | 3/2000 | Tsugita et al. |
| 6,042,607 A | 3/2000 | Williamson, IV et al. |
| 6,045,565 A | 4/2000 | Ellis et al. |
| 6,051,014 A | 4/2000 | Jang |
| 6,051,104 A | 4/2000 | Oriaran et al. |
| 6,053,924 A | 4/2000 | Hussein |
| 6,053,942 A | 4/2000 | Eno et al. |
| 6,056,743 A | 5/2000 | Ellis et al. |
| 6,059,809 A | 5/2000 | Amor et al. |
| 6,059,827 A | 5/2000 | Fenton, Jr. |
| 6,066,160 A | 5/2000 | Colvin et al. |
| 6,067,988 A | 5/2000 | Mueller |
| 6,068,638 A | 5/2000 | Makower |
| 6,071,292 A | 6/2000 | Makower et al. |
| 6,074,416 A | 6/2000 | Berg et al. |
| 6,074,417 A | 6/2000 | Peredo |
| 6,074,418 A | 6/2000 | Buchanan et al. |
| 6,076,529 A | 6/2000 | Vanney et al. |
| 6,076,742 A | 6/2000 | Benary |
| 6,077,297 A | 6/2000 | Robinson et al. |
| 6,079,414 A | 6/2000 | Roth |
| 6,080,163 A | 6/2000 | Hussein et al. |
| 6,080,170 A | 6/2000 | Nash et al. |
| 6,083,257 A | 7/2000 | Taylor et al. |
| 6,091,042 A | 7/2000 | Benary |
| 6,092,526 A | 7/2000 | LaFontaine et al. |
| 6,092,529 A | 7/2000 | Cox |
| 6,093,166 A | 7/2000 | Knudson et al. |
| 6,093,177 A | 7/2000 | Javier, Jr. et al. |
| 6,093,185 A | 7/2000 | Ellis et al. |
| 6,093,203 A | 7/2000 | Uflacker |
| 6,093,530 A | 7/2000 | Mcilroy et al. |
| 6,096,074 A | 8/2000 | Pedros |
| 6,102,941 A | 8/2000 | Tweden et al. |
| 6,102,944 A | 8/2000 | Huynh et al. |
| 6,106,550 A | 8/2000 | Magovern et al. |
| 6,110,191 A | 8/2000 | Dehdashtian et al. |
| 6,110,198 A | 8/2000 | Fogarty et al. |
| 6,110,201 A | 8/2000 | Quijano et al. |
| 6,113,612 A | 9/2000 | Swanson et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,120,534 A | 9/2000 | Ruiz |
| 6,123,682 A | 9/2000 | Knudson et al. |
| 6,123,723 A | 9/2000 | Konya et al. |
| 6,125,852 A | 10/2000 | Stevens et al. |
| 6,126,649 A | 10/2000 | Vantassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,132,473 A | 10/2000 | Williams et al. |
| 6,132,986 A | 10/2000 | Pathak et al. |
| 6,139,510 A | 10/2000 | Palermo |
| 6,139,541 A | 10/2000 | Vanney et al. |
| 6,142,987 A | 11/2000 | Tsugita |
| 6,143,021 A | 11/2000 | Staehle |
| 6,143,987 A | 11/2000 | Makita |
| 6,146,366 A | 11/2000 | Schachar |
| 6,146,415 A | 11/2000 | Fitz |
| 6,146,417 A | 11/2000 | Ischinger |
| 6,152,937 A | 11/2000 | Peterson et al. |
| 6,152,956 A | 11/2000 | Pierce |
| 6,155,264 A | 12/2000 | Ressemann et al. |
| 6,156,031 A | 12/2000 | Aita et al. |
| 6,156,055 A | 12/2000 | Ravenscroft |
| 6,156,531 A | 12/2000 | Pathak et al. |
| 6,157,852 A | 12/2000 | Selmon et al. |
| 6,159,225 A | 12/2000 | Makower |
| 6,159,239 A | 12/2000 | Greenhalgh |
| 6,162,208 A | 12/2000 | Hipps |
| 6,162,245 A | 12/2000 | Jayaraman |
| 6,165,185 A | 12/2000 | Shennib et al. |
| 6,165,188 A | 12/2000 | Saadat et al. |
| 6,165,200 A | 12/2000 | Tsugita et al. |
| 6,165,209 A | 12/2000 | Patterson et al. |
| 6,167,605 B1 | 1/2001 | Morales |
| 6,168,579 B1 | 1/2001 | Tsugita |
| 6,168,614 B1 | 1/2001 | Andersen et al. |
| 6,168,616 B1 | 1/2001 | Brown, III |
| 6,171,251 B1 | 1/2001 | Mueller et al. |
| 6,171,327 B1 | 1/2001 | Daniel et al. |
| 6,171,335 B1 | 1/2001 | Wheatley et al. |
| 6,177,514 B1 | 1/2001 | Pathak et al. |
| 6,179,859 B1 | 1/2001 | Bates et al. |
| 6,182,664 B1 | 2/2001 | Cosgrove |
| 6,182,668 B1 | 2/2001 | Tweden et al. |
| 6,183,481 B1 | 2/2001 | Lee et al. |
| 6,186,972 B1 | 2/2001 | Nelson et al. |
| 6,187,016 B1 | 2/2001 | Hedges et al. |
| 6,190,353 B1 | 2/2001 | Makower et al. |
| 6,190,393 B1 | 2/2001 | Bevier et al. |

(56)  References Cited

U.S. PATENT DOCUMENTS

| | | | |
|---|---|---|---|
| 6,190,405 B1 | 2/2001 | Culombo et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,053 B1 | 3/2001 | Cosgrove et al. |
| 6,197,296 B1 | 3/2001 | Davies et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,550 B1 | 3/2001 | Olson |
| 6,203,556 B1 | 3/2001 | Evans et al. |
| 6,206,888 B1 | 3/2001 | Bicek et al. |
| 6,206,911 B1 | 3/2001 | Milo |
| 6,210,408 B1 | 4/2001 | Chandrasekaran et al. |
| 6,210,957 B1 | 4/2001 | Carpentier et al. |
| 6,213,126 B1 | 4/2001 | LaFontaine et al. |
| 6,214,036 B1 | 4/2001 | Letendre et al. |
| 6,214,041 B1 | 4/2001 | Tweden et al. |
| 6,214,054 B1 | 4/2001 | Cunanan et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,217,609 B1 | 4/2001 | Haverkost |
| 6,218,662 B1 | 4/2001 | Tchakarov et al. |
| 6,221,006 B1 | 4/2001 | Dubrul et al. |
| 6,221,049 B1 | 4/2001 | Selmon et al. |
| 6,221,091 B1 | 4/2001 | Khosravi |
| 6,221,096 B1 | 4/2001 | Aiba et al. |
| 6,221,100 B1 | 4/2001 | Strecker |
| 6,223,752 B1 | 5/2001 | Vanney et al. |
| 6,224,584 B1 | 5/2001 | March et al. |
| 6,231,544 B1 | 5/2001 | Tsugita et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,738 B1 | 6/2001 | Dereume |
| 6,241,741 B1 | 6/2001 | Duhaylongsod et al. |
| 6,241,757 B1 | 6/2001 | An et al. |
| 6,245,102 B1 | 6/2001 | Jayaraman |
| 6,245,103 B1 | 6/2001 | Stinson |
| 6,245,105 B1 | 6/2001 | Nguyen et al. |
| 6,248,112 B1 | 6/2001 | Gambale et al. |
| 6,248,116 B1 | 6/2001 | Chevillon et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,135 B1 | 6/2001 | Stinson et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,635 B1 | 7/2001 | Schroeder et al. |
| 6,254,636 B1 | 7/2001 | Peredo |
| 6,257,634 B1 | 7/2001 | Wei |
| 6,258,052 B1 | 7/2001 | Milo |
| 6,258,087 B1 | 7/2001 | Edwards et al. |
| 6,258,114 B1 | 7/2001 | Konya et al. |
| 6,258,115 B1 | 7/2001 | Dubrul |
| 6,258,119 B1 | 7/2001 | Hussein et al. |
| 6,258,120 B1 | 7/2001 | McKenzie et al. |
| 6,258,129 B1 | 7/2001 | Dybdal et al. |
| 6,258,150 B1 | 7/2001 | MacKellar |
| 6,261,304 B1 | 7/2001 | Hall et al. |
| 6,267,783 B1 | 7/2001 | Letendre et al. |
| 6,269,819 B1 | 8/2001 | Oz et al. |
| 6,270,513 B1 | 8/2001 | Tsugita et al. |
| 6,270,521 B1 | 8/2001 | Fischell et al. |
| 6,270,526 B1 | 8/2001 | Cox |
| 6,273,876 B1 | 8/2001 | Klima et al. |
| 6,273,895 B1 | 8/2001 | Pinchuk et al. |
| 6,276,661 B1 | 8/2001 | Laird |
| 6,277,555 B1 | 8/2001 | Duran et al. |
| 6,283,127 B1 | 9/2001 | Sterman et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,334 B1 | 9/2001 | Moll et al. |
| 6,287,338 B1 | 9/2001 | Sarnowski et al. |
| 6,287,339 B1 | 9/2001 | Vazquez et al. |
| 6,290,709 B1 | 9/2001 | Ellis et al. |
| 6,290,728 B1 | 9/2001 | Phelps et al. |
| 6,296,662 B1 | 10/2001 | Caffey |
| 6,299,637 B1 | 10/2001 | Shaolian et al. |
| 6,302,875 B1 | 10/2001 | Makower et al. |
| 6,302,892 B1 | 10/2001 | Wilk |
| 6,302,906 B1 | 10/2001 | Goicoechea et al. |
| 6,306,164 B1 | 10/2001 | Kujawski |
| 6,309,382 B1 | 10/2001 | Garrison et al. |
| 6,309,417 B1 | 10/2001 | Spence et al. |
| 6,311,693 B1 | 11/2001 | Sterman et al. |
| 6,312,465 B1 | 11/2001 | Griffin et al. |
| 6,319,281 B1 | 11/2001 | Patel |
| 6,322,548 B1 | 11/2001 | Payne et al. |
| 6,322,593 B1 | 11/2001 | Pathak et al. |
| 6,325,067 B1 | 12/2001 | Sterman et al. |
| 6,327,772 B1 | 12/2001 | Zadno-Azizi et al. |
| 6,330,884 B1 | 12/2001 | Kim |
| 6,331,189 B1 | 12/2001 | Wolinsky et al. |
| 6,334,873 B1 | 1/2002 | Lane et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,346,074 B1 | 2/2002 | Roth |
| 6,346,116 B1 | 2/2002 | Brooks et al. |
| 6,348,063 B1 | 2/2002 | Yassour et al. |
| 6,350,248 B1 | 2/2002 | Knudson et al. |
| 6,350,277 B1 | 2/2002 | Kocur |
| 6,350,278 B1 | 2/2002 | Lenker et al. |
| 6,352,547 B1 | 3/2002 | Brown et al. |
| 6,352,554 B2 | 3/2002 | De Paulis |
| 6,352,708 B1 | 3/2002 | Duran et al. |
| 6,357,104 B1 | 3/2002 | Myers |
| 6,358,277 B1 | 3/2002 | Duran |
| 6,361,519 B1 | 3/2002 | Knudson et al. |
| 6,361,545 B1 | 3/2002 | Macoviak et al. |
| 6,363,938 B2 | 4/2002 | Saadat et al. |
| 6,363,939 B1 | 4/2002 | Wilk |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,983 B1 | 4/2002 | Lane |
| 6,375,615 B1 | 4/2002 | Flaherty et al. |
| 6,378,221 B1 | 4/2002 | Ekholm, Jr. et al. |
| 6,379,319 B1 | 4/2002 | Garibotto et al. |
| 6,379,365 B1 | 4/2002 | Diaz |
| 6,379,372 B1 | 4/2002 | Dehdashtian et al. |
| 6,379,383 B1 | 4/2002 | Palmaz et al. |
| 6,379,740 B1 | 4/2002 | Rinaldi et al. |
| 6,380,457 B1 | 4/2002 | Yurek et al. |
| 6,383,193 B1 | 5/2002 | Cathcart et al. |
| 6,387,119 B2 | 5/2002 | Wolf et al. |
| 6,387,122 B1 | 5/2002 | Cragg |
| 6,390,098 B1 | 5/2002 | LaFontaine et al. |
| 6,391,051 B2 | 5/2002 | Sullivan, III et al. |
| 6,391,538 B1 | 5/2002 | Vyavahare et al. |
| 6,395,208 B1 | 5/2002 | Herweck et al. |
| 6,398,807 B1 | 6/2002 | Chouinard et al. |
| 6,401,720 B1 | 6/2002 | Stevens et al. |
| 6,402,736 B1 | 6/2002 | Brown et al. |
| 6,402,740 B1 | 6/2002 | Ellis et al. |
| 6,406,488 B1 | 6/2002 | Tweden et al. |

(56)　　　　　　References Cited

U.S. PATENT DOCUMENTS

| | | | |
|---|---|---|---|
| 6,406,491 B1 | 6/2002 | Vanney |
| 6,406,493 B1 | 6/2002 | Tu et al. |
| 6,409,697 B2 | 6/2002 | Eno et al. |
| 6,409,750 B1 | 6/2002 | Hyodoh et al. |
| 6,409,751 B1 | 6/2002 | Hall et al. |
| 6,409,755 B1 | 6/2002 | Vrba |
| 6,409,759 B1 | 6/2002 | Peredo |
| 6,413,275 B1 | 7/2002 | Nguyen et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,440,164 B1 | 8/2002 | DiMatteo et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,025 B1 | 9/2002 | Jervis |
| 6,451,054 B1 | 9/2002 | Stevens |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,153 B1 | 10/2002 | Bailey et al. |
| 6,458,323 B1 | 10/2002 | Boekstegers |
| 6,461,382 B1 | 10/2002 | Cao |
| 6,464,709 B2 | 10/2002 | Shennib et al. |
| 6,468,303 B1 | 10/2002 | Amplatz et al. |
| 6,468,660 B2 | 10/2002 | Ogle et al. |
| 6,471,723 B1 | 10/2002 | Ashworth et al. |
| 6,475,169 B2 | 11/2002 | Ferrera |
| 6,475,226 B1 | 11/2002 | Belef et al. |
| 6,475,239 B1 | 11/2002 | Campbell et al. |
| 6,475,244 B2 | 11/2002 | Herweck et al. |
| 6,478,819 B2 | 11/2002 | Moe |
| 6,479,079 B1 | 11/2002 | Pathak et al. |
| 6,482,220 B1 | 11/2002 | Mueller |
| 6,482,228 B1 | 11/2002 | Norred |
| 6,485,501 B1 | 11/2002 | Green |
| 6,485,502 B2 | 11/2002 | Don Michael et al. |
| 6,485,513 B1 | 11/2002 | Fan |
| 6,485,524 B2 | 11/2002 | Strecker |
| 6,487,581 B1 | 11/2002 | Spence et al. |
| 6,488,704 B1 | 12/2002 | Connelly et al. |
| 6,491,689 B1 | 12/2002 | Ellis et al. |
| 6,491,707 B2 | 12/2002 | Makower et al. |
| 6,494,211 B1 | 12/2002 | Boyd et al. |
| 6,494,897 B2 | 12/2002 | Sterman et al. |
| 6,494,909 B2 | 12/2002 | Greenhalgh |
| 6,503,272 B2 | 1/2003 | Duerig et al. |
| 6,508,496 B1 | 1/2003 | Huang |
| 6,508,803 B1 | 1/2003 | Horikawa et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,511,491 B2 | 1/2003 | Grudem et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,517,573 B1 | 2/2003 | Pollock et al. |
| 6,521,179 B1 | 2/2003 | Girardot et al. |
| 6,524,323 B1 | 2/2003 | Nash et al. |
| 6,524,335 B1 | 2/2003 | Hartley et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,533,807 B2 | 3/2003 | Wolinsky et al. |
| 6,537,297 B2 | 3/2003 | Tsugita et al. |
| 6,537,310 B1 | 3/2003 | Palmaz et al. |
| 6,540,768 B1 | 4/2003 | Diaz et al. |
| 6,540,782 B1 | 4/2003 | Snyders |
| 6,544,230 B1 | 4/2003 | Flaherty et al. |
| 6,547,827 B2 | 4/2003 | Carpentier et al. |
| 6,551,303 B1 | 4/2003 | Van Tassel et al. |
| 6,558,318 B1 | 5/2003 | Daniel et al. |
| 6,558,417 B2 | 5/2003 | Peredo |
| 6,558,418 B2 | 5/2003 | Carpentier et al. |
| 6,558,429 B2 | 5/2003 | Taylor |
| 6,559,132 B1 | 5/2003 | Holmer |
| 6,561,998 B1 | 5/2003 | Roth et al. |
| 6,562,031 B2 | 5/2003 | Chandrasekaran et al. |
| 6,562,058 B2 | 5/2003 | Seguin et al. |
| 6,562,063 B1 | 5/2003 | Euteneuer et al. |
| 6,562,069 B2 | 5/2003 | Cai et al. |
| 6,564,805 B2 | 5/2003 | Garrison et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,569,196 B1 | 5/2003 | Vesely |
| 6,572,593 B1 | 6/2003 | Daum |
| 6,572,642 B2 | 6/2003 | Rinaldi et al. |
| 6,572,643 B1 | 6/2003 | Gharibadeh |
| 6,572,652 B2 | 6/2003 | Shaknovich |
| 6,575,168 B2 | 6/2003 | LaFontaine et al. |
| 6,579,311 B1 | 6/2003 | Makower |
| 6,582,444 B2 | 6/2003 | Wilk |
| 6,582,460 B1 | 6/2003 | Cryer |
| 6,582,462 B1 | 6/2003 | Andersen et al. |
| 6,585,756 B1 | 7/2003 | Strecker |
| 6,585,758 B1 | 7/2003 | Chouinard et al. |
| 6,585,766 B1 | 7/2003 | Huynh et al. |
| 6,589,279 B1 | 7/2003 | Anderson et al. |
| 6,592,546 B1 | 7/2003 | Barbut et al. |
| 6,592,614 B2 | 7/2003 | Lenker et al. |
| 6,599,304 B1 | 7/2003 | Selmon et al. |
| 6,600,803 B2 | 7/2003 | Bruder et al. |
| 6,605,053 B1 | 8/2003 | Kamm et al. |
| 6,605,112 B1 | 8/2003 | Moll et al. |
| 6,605,113 B2 | 8/2003 | Wilk |
| 6,608,040 B1 | 8/2003 | Lin et al. |
| 6,610,077 B1 | 8/2003 | Hancock et al. |
| 6,610,085 B1 | 8/2003 | Lazarus |
| 6,610,100 B2 | 8/2003 | Phelps et al. |
| 6,613,069 B2 | 9/2003 | Boyd et al. |
| 6,613,077 B2 | 9/2003 | Gilligan et al. |
| 6,613,079 B1 | 9/2003 | Wolinsky et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,626,939 B1 | 9/2003 | Burnside et al. |
| 6,632,241 B1 | 10/2003 | Hancock et al. |
| 6,632,243 B1 | 10/2003 | Zadno-Azizi et al. |
| 6,632,470 B2 | 10/2003 | Morra et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,635,085 B1 | 10/2003 | Caffey et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,546 B1 | 11/2003 | Nash et al. |
| 6,652,555 B1 | 11/2003 | Vantassel et al. |
| 6,652,571 B1 | 11/2003 | White et al. |
| 6,652,578 B2 | 11/2003 | Bailey et al. |
| 6,655,386 B1 | 12/2003 | Makower et al. |
| 6,656,213 B2 | 12/2003 | Solem |
| 6,660,003 B1 | 12/2003 | DeVore et al. |

(56) References Cited

U.S. PATENT DOCUMENTS

| | | |
|---|---|---|
| 6,660,024 B1 | 12/2003 | Flaherty et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,666,863 B2 | 12/2003 | Wentzel et al. |
| 6,669,709 B1 | 12/2003 | Cohn et al. |
| 6,669,724 B2 | 12/2003 | Park et al. |
| 6,673,089 B1 | 1/2004 | Yassour et al. |
| 6,673,101 B1 | 1/2004 | Fitzgerald et al. |
| 6,673,106 B2 | 1/2004 | Mitelberg et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,693 B1 | 1/2004 | Belding et al. |
| 6,676,698 B2 | 1/2004 | McGuckin, Jr. et al. |
| 6,679,268 B2 | 1/2004 | Stevens et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,648 B2 | 2/2004 | Flaherty et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,694,983 B2 | 2/2004 | Wolf et al. |
| 6,695,864 B2 | 2/2004 | Macoviak et al. |
| 6,695,865 B2 | 2/2004 | Boyle et al. |
| 6,695,875 B2 | 2/2004 | Stelter et al. |
| 6,695,878 B2 | 2/2004 | McGuckin, Jr. et al. |
| 6,699,274 B2 | 3/2004 | Stinson |
| 6,701,932 B2 | 3/2004 | Knudson et al. |
| 6,702,851 B1 | 3/2004 | Chinn et al. |
| 6,709,425 B2 | 3/2004 | Gambale et al. |
| 6,709,444 B1 | 3/2004 | Makower |
| 6,712,842 B1 | 3/2004 | Gifford, III et al. |
| 6,712,843 B2 | 3/2004 | Elliott |
| 6,714,841 B1 | 3/2004 | Wright et al. |
| 6,714,842 B1 | 3/2004 | Ito |
| 6,719,770 B2 | 4/2004 | Laufer et al. |
| 6,719,787 B2 | 4/2004 | Cox |
| 6,719,788 B2 | 4/2004 | Cox |
| 6,719,789 B2 | 4/2004 | Cox |
| 6,723,116 B2 | 4/2004 | Taheri |
| 6,723,122 B2 | 4/2004 | Yang et al. |
| 6,726,677 B1 | 4/2004 | Flaherty et al. |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,730,377 B2 | 5/2004 | Wang |
| 6,733,513 B2 | 5/2004 | Boyle et al. |
| 6,733,525 B2 | 5/2004 | Yang et al. |
| 6,736,827 B1 | 5/2004 | McAndrew et al. |
| 6,736,839 B2 | 5/2004 | Cummings |
| 6,736,845 B2 | 5/2004 | Marquez et al. |
| 6,736,846 B2 | 5/2004 | Cox |
| 6,743,252 B1 | 6/2004 | Bates et al. |
| 6,746,464 B1 | 6/2004 | Makower |
| 6,752,828 B2 | 6/2004 | Thornton |
| 6,755,854 B2 | 6/2004 | Gillick et al. |
| 6,755,855 B2 | 6/2004 | Yurek et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,767,362 B2 | 7/2004 | Schreck |
| 6,769,434 B2 | 8/2004 | Liddicoat et al. |
| 6,773,454 B2 | 8/2004 | Wholey et al. |
| 6,773,455 B2 | 8/2004 | Allen et al. |
| 6,773,456 B1 | 8/2004 | Gordon et al. |
| 6,774,278 B1 | 8/2004 | Ragheb et al. |
| 6,776,791 B1 | 8/2004 | Stallings et al. |
| 6,786,925 B1 | 9/2004 | Schoon et al. |
| 6,786,929 B2 | 9/2004 | Gambale et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,000 B2 | 9/2004 | Simpson et al. |
| 6,797,002 B2 | 9/2004 | Spence et al. |
| 6,802,319 B2 | 10/2004 | Stevens et al. |
| 6,802,858 B2 | 10/2004 | Gambale et al. |
| 6,805,711 B2 | 10/2004 | Quijano et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,814,746 B2 | 11/2004 | Thompson et al. |
| 6,814,754 B2 | 11/2004 | Greenhalgh |
| 6,820,676 B2 | 11/2004 | Palmaz et al. |
| 6,821,211 B2 | 11/2004 | Otten et al. |
| 6,821,297 B2 | 11/2004 | Snyders |
| 6,824,041 B2 | 11/2004 | Grieder et al. |
| 6,824,970 B2 | 11/2004 | Vyavahare et al. |
| 6,830,568 B1 | 12/2004 | Kesten et al. |
| 6,830,575 B2 | 12/2004 | Stenzel et al. |
| 6,830,584 B1 | 12/2004 | Seguin |
| 6,830,585 B1 | 12/2004 | Artof et al. |
| 6,830,586 B2 | 12/2004 | Quijano et al. |
| 6,837,901 B2 | 1/2005 | Rabkin et al. |
| 6,837,902 B2 | 1/2005 | Nguyen et al. |
| 6,840,957 B2 | 1/2005 | DiMatteo et al. |
| 6,843,802 B1 | 1/2005 | Villalobos et al. |
| 6,846,325 B2 | 1/2005 | Liddicoat |
| 6,849,084 B2 | 2/2005 | Rabkin et al. |
| 6,849,085 B2 | 2/2005 | Marton |
| 6,854,467 B2 | 2/2005 | Boekstegers |
| 6,860,898 B2 | 3/2005 | Stack et al. |
| 6,861,211 B2 | 3/2005 | Levy et al. |
| 6,863,668 B2 | 3/2005 | Gillespie et al. |
| 6,863,684 B2 | 3/2005 | Kim et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,199 B2 | 4/2005 | Wilk et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,899,704 B2 | 5/2005 | Sterman et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,913,021 B2 | 7/2005 | Knudson et al. |
| 6,913,600 B2 | 7/2005 | Valley et al. |
| 6,916,304 B2 | 7/2005 | Eno et al. |
| 6,920,674 B2 | 7/2005 | Thornton |
| 6,920,732 B2 | 7/2005 | Martensson |
| 6,926,690 B2 | 8/2005 | Renati |
| 6,926,732 B2 | 8/2005 | Derus et al. |
| 6,929,009 B2 | 8/2005 | Makower et al. |
| 6,929,011 B2 | 8/2005 | Knudson et al. |
| 6,929,653 B2 | 8/2005 | Strecter |
| 6,936,058 B2 | 8/2005 | Forde et al. |
| 6,936,066 B2 | 8/2005 | Palmaz et al. |
| 6,936,067 B2 | 8/2005 | Buchanan |
| 6,939,352 B2 | 9/2005 | Buzzard et al. |
| 6,939,359 B2 | 9/2005 | Tu et al. |
| 6,939,365 B1 | 9/2005 | Fogarty et al. |
| 6,939,370 B2 | 9/2005 | Hartley et al. |
| 6,942,682 B2 | 9/2005 | Vrba et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,951,571 B1 | 10/2005 | Srivastava |

(56)            References Cited

U.S. PATENT DOCUMENTS

| | | | |
|---|---|---|---|
| 6,953,332 B1 | 10/2005 | Kurk et al. |
| 6,953,481 B2 | 10/2005 | Phelps et al. |
| 6,955,175 B2 | 10/2005 | Stevens et al. |
| 6,955,681 B2 | 10/2005 | Evans et al. |
| 6,964,652 B2 | 11/2005 | Guiles et al. |
| 6,964,673 B2 | 11/2005 | Tsugita et al. |
| 6,964,676 B1 | 11/2005 | Gerberding et al. |
| 6,969,395 B2 | 11/2005 | Eskuri |
| 6,972,025 B2 | 12/2005 | Wasdyke |
| 6,972,029 B2 | 12/2005 | Mayrhofer et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,990 B2 | 12/2005 | Mowry |
| 6,979,350 B2 | 12/2005 | Moll et al. |
| 6,984,242 B2 | 1/2006 | Campbell et al. |
| 6,984,244 B2 | 1/2006 | Perez et al. |
| 6,986,742 B2 | 1/2006 | Hart et al. |
| 6,986,784 B1 | 1/2006 | Weiser et al. |
| 6,988,949 B2 | 1/2006 | Wang |
| 6,989,027 B2 | 1/2006 | Allen et al. |
| 6,989,028 B2 | 1/2006 | Lashinski et al. |
| 6,991,649 B2 | 1/2006 | Sievers |
| 7,001,425 B2 | 2/2006 | McCullagh et al. |
| 7,004,176 B2 | 2/2006 | Lau |
| 7,008,397 B2 | 3/2006 | Tweden et al. |
| 7,011,095 B2 | 3/2006 | Wolf et al. |
| 7,011,681 B2 | 3/2006 | Vesely |
| 7,014,655 B2 | 3/2006 | Barbarash et al. |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,022,134 B1 | 4/2006 | Quijano et al. |
| 7,025,773 B2 | 4/2006 | Gittings et al. |
| 7,025,780 B2 | 4/2006 | Gabbay |
| 7,025,791 B2 | 4/2006 | Levine et al. |
| 7,028,692 B2 | 4/2006 | Sterman et al. |
| 7,037,331 B2 | 5/2006 | Mitelberg et al. |
| 7,037,333 B2 | 5/2006 | Myers et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,048,757 B2 | 5/2006 | Shaknovich |
| 7,050,276 B2 | 5/2006 | Nishiyama |
| 7,074,236 B2 | 7/2006 | Rabkin et al. |
| 7,078,163 B2 | 7/2006 | Torrianni |
| 7,081,132 B2 | 7/2006 | Cook et al. |
| 7,097,658 B2 | 8/2006 | Oktay |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,108,715 B2 | 9/2006 | Lawrence-Brown et al. |
| 7,115,141 B2 | 10/2006 | Menz et al. |
| 7,118,585 B2 | 10/2006 | Addis |
| 7,122,020 B2 | 10/2006 | Mogul |
| 7,125,418 B2 | 10/2006 | Duran et al. |
| 7,128,759 B2 | 10/2006 | Osborne et al. |
| 7,137,184 B2 | 11/2006 | Schreck |
| 7,141,063 B2 | 11/2006 | White et al. |
| 7,141,064 B2 | 11/2006 | Scott et al. |
| 7,143,312 B1 | 11/2006 | Wang et al. |
| 7,147,662 B1 | 12/2006 | Pollock et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,163,556 B2 | 1/2007 | Xie et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,189,258 B2 | 3/2007 | Johnson et al. |
| 7,189,259 B2 | 3/2007 | Simionescu et al. |
| 7,191,018 B2 | 3/2007 | Gielen et al. |
| 7,191,406 B1 | 3/2007 | Barber et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,214,344 B2 | 5/2007 | Carpentier et al. |
| 7,217,287 B2 | 5/2007 | Wilson et al. |
| 7,235,092 B2 | 6/2007 | Banas et al. |
| 7,235,093 B2 | 6/2007 | Gregorich |
| 7,238,200 B2 | 7/2007 | Lee et al. |
| 7,241,257 B1 | 7/2007 | Ainsworth et al. |
| 7,252,682 B2 | 8/2007 | Seguin |
| 7,258,696 B2 | 8/2007 | Rabkin et al. |
| 7,258,891 B2 | 8/2007 | Pacetti et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,285,130 B2 | 10/2007 | Austin |
| 7,297,150 B2 | 11/2007 | Cartledge et al. |
| 7,300,457 B2 | 11/2007 | Palmaz |
| 7,300,463 B2 | 11/2007 | Liddicoat |
| 7,311,730 B2 | 12/2007 | Gabbay |
| 7,314,449 B2 | 1/2008 | Pfeiffer et al. |
| 7,314,485 B2 | 1/2008 | Mathis |
| 7,314,880 B2 | 1/2008 | Chang et al. |
| 7,316,706 B2 | 1/2008 | Bloom et al. |
| 7,316,712 B2 | 1/2008 | Peredo |
| 7,317,005 B2 | 1/2008 | Hoekstra et al. |
| 7,317,942 B2 | 1/2008 | Brown |
| 7,317,950 B2 | 1/2008 | Lee |
| 7,318,278 B2 | 1/2008 | Zhang et al. |
| 7,318,998 B2 | 1/2008 | Goldstein et al. |
| 7,319,096 B2 | 1/2008 | Malm et al. |
| 7,320,692 B1 | 1/2008 | Bender et al. |
| 7,320,704 B2 | 1/2008 | Lashinski et al. |
| 7,320,705 B2 | 1/2008 | Quintessenza |
| 7,320,706 B2 | 1/2008 | Al-Najjar |
| 7,322,932 B2 | 1/2008 | Xie et al. |
| 7,323,006 B2 | 1/2008 | Andreas et al. |
| 7,323,066 B1 | 1/2008 | Budron |
| 7,326,174 B2 | 2/2008 | Cox et al. |
| 7,326,219 B2 | 2/2008 | Mowry et al. |
| 7,326,236 B2 | 2/2008 | Andreas et al. |
| 7,327,862 B2 | 2/2008 | Murphy et al. |
| 7,329,278 B2 | 2/2008 | Seguin et al. |
| 7,329,279 B2 | 2/2008 | Haug et al. |
| 7,329,280 B2 | 2/2008 | Bolling et al. |
| 7,329,777 B2 | 2/2008 | Harter et al. |
| 7,331,991 B2 | 2/2008 | Kheradvar et al. |
| 7,331,993 B2 | 2/2008 | White |
| 7,333,643 B2 | 2/2008 | Murphy et al. |
| 7,335,158 B2 | 2/2008 | Taylor |
| 7,335,213 B1 | 2/2008 | Hyde et al. |
| 7,335,218 B2 | 2/2008 | Wilson et al. |
| 7,335,490 B2 | 2/2008 | Van Gilst et al. |
| 7,338,484 B2 | 3/2008 | Schoon et al. |
| 7,338,520 B2 | 3/2008 | Bailey et al. |
| 7,361,189 B2 | 4/2008 | Case et al. |
| 7,361,190 B2 | 4/2008 | Shaoulian et al. |
| 7,364,588 B2 | 4/2008 | Mathis et al. |
| 7,371,258 B2 | 5/2008 | Woo et al. |
| 7,374,560 B2 | 5/2008 | Ressemann et al. |
| 7,374,571 B2 | 5/2008 | Pease et al. |
| 7,377,895 B2 | 5/2008 | Spence et al. |
| 7,377,938 B2 | 5/2008 | Sarac et al. |
| 7,377,940 B2 | 5/2008 | Ryan et al. |
| 7,381,210 B2 | 6/2008 | Zarbatany et al. |
| 7,381,216 B2 | 6/2008 | Buzzard et al. |
| 7,381,218 B2 | 6/2008 | Schreck |
| 7,381,219 B2 | 6/2008 | Salahieh et al. |
| 7,381,220 B2 | 6/2008 | Macoviak et al. |
| 7,384,411 B1 | 6/2008 | Condado |
| 7,387,640 B2 | 6/2008 | Cummings |
| 7,389,874 B2 | 6/2008 | Quest et al. |
| 7,390,325 B2 | 6/2008 | Wang et al. |

(56) References Cited

U.S. PATENT DOCUMENTS

| | | | |
|---|---|---|---|
| 7,393,358 B2 | 7/2008 | Malewicz |
| 7,393,360 B2 | 7/2008 | Spenser et al. |
| 7,396,364 B2 | 7/2008 | Moaddeb et al. |
| 7,399,315 B2 | 7/2008 | Iobbi |
| 7,402,171 B2 | 7/2008 | Osborne et al. |
| 7,404,792 B2 | 7/2008 | Spence et al. |
| 7,404,793 B2 | 7/2008 | Lau et al. |
| 7,405,259 B2 | 7/2008 | Frye et al. |
| 7,410,499 B2 | 8/2008 | Bicer |
| 7,412,274 B2 | 8/2008 | Mejia |
| 7,412,290 B2 | 8/2008 | Janke et al. |
| 7,415,861 B2 | 8/2008 | Sokel |
| 7,416,530 B2 | 8/2008 | Turner et al. |
| 7,422,603 B2 | 9/2008 | Lane |
| 7,422,606 B2 | 9/2008 | Ung-Chhun et al. |
| 7,423,032 B2 | 9/2008 | Ozaki et al. |
| 7,426,413 B2 | 9/2008 | Balczewski et al. |
| 7,427,279 B2 | 9/2008 | Frazier et al. |
| 7,427,287 B2 | 9/2008 | Turovskiy et al. |
| 7,427,291 B2 | 9/2008 | Liddicoat et al. |
| 7,429,269 B2 | 9/2008 | Schwammenthal et al. |
| 7,430,448 B1 | 9/2008 | Zimmer et al. |
| 7,430,484 B2 | 9/2008 | Ohara |
| 7,431,691 B1 | 10/2008 | Wilk |
| 7,431,733 B2 | 10/2008 | Knight |
| 7,435,059 B2 | 10/2008 | Smith et al. |
| 7,435,257 B2 | 10/2008 | Lashinski et al. |
| 7,442,204 B2 | 10/2008 | Schwammenthal et al. |
| RE40,570 E | 11/2008 | Carpentier et al. |
| 7,445,630 B2 | 11/2008 | Lashinski et al. |
| 7,445,631 B2 | 11/2008 | Salahieh et al. |
| 7,445,632 B2 | 11/2008 | McGuckin, Jr. et al. |
| 7,452,371 B2 | 11/2008 | Pavcnik et al. |
| 7,455,689 B2 | 11/2008 | Johnson |
| 7,462,156 B2 | 12/2008 | Mitrev |
| 7,462,184 B2 | 12/2008 | Worley et al. |
| 7,462,191 B2 | 12/2008 | Spenser et al. |
| 7,468,050 B1 | 12/2008 | Kantrowitz |
| 7,470,282 B2 | 12/2008 | Shelso |
| 7,470,284 B2 | 12/2008 | Lambrecht et al. |
| 7,470,285 B2 | 12/2008 | Nugent et al. |
| 7,473,271 B2 | 1/2009 | Gunderson |
| 7,473,275 B2 | 1/2009 | Marquez |
| 7,473,417 B2 | 1/2009 | Zeltinger et al. |
| 7,476,196 B2 | 1/2009 | Spence et al. |
| 7,476,199 B2 | 1/2009 | Spence et al. |
| 7,476,200 B2 | 1/2009 | Tal |
| 7,476,244 B2 | 1/2009 | Buzzard et al. |
| 7,481,838 B2 | 1/2009 | Carpentier et al. |
| 7,485,088 B2 | 2/2009 | Murphy et al. |
| 7,485,143 B2 | 2/2009 | Webler et al. |
| 7,488,346 B2 | 2/2009 | Navia |
| 7,491,232 B2 | 2/2009 | Bolduc et al. |
| 7,493,869 B1 | 2/2009 | Foster et al. |
| 7,497,824 B2 | 3/2009 | Taylor |
| 7,500,949 B2 | 3/2009 | Gottlieb et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,507,199 B2 | 3/2009 | Wang et al. |
| 7,510,572 B2 | 3/2009 | Gabbay |
| 7,510,574 B2 | 3/2009 | Le et al. |
| 7,510,575 B2 | 3/2009 | Spenser et al. |
| 7,510,577 B2 | 3/2009 | Moaddeb et al. |
| 7,513,863 B2 | 4/2009 | Bolling et al. |
| 7,513,909 B2 | 4/2009 | Lane et al. |
| 7,522,950 B2 | 4/2009 | Fuimaono et al. |
| 7,524,330 B2 | 4/2009 | Berreklouw |
| 7,530,253 B2 | 5/2009 | Spenser et al. |
| 7,530,995 B2 | 5/2009 | Quijano et al. |
| 7,534,261 B2 | 5/2009 | Friedman |
| 7,544,206 B2 | 6/2009 | Cohn |
| 7,547,322 B2 | 6/2009 | Sarac et al. |
| 7,553,324 B2 | 6/2009 | Andreas et al. |
| 7,556,386 B2 | 7/2009 | Smith |
| 7,556,646 B2 | 7/2009 | Yang et al. |
| 7,569,071 B2 | 8/2009 | Haverkost et al. |
| 7,578,828 B2 | 8/2009 | Gittings et al. |
| 7,585,321 B2 | 9/2009 | Cribier |
| 7,591,848 B2 | 9/2009 | Allen |
| 7,594,974 B2 | 9/2009 | Cali et al. |
| 7,601,159 B2 | 10/2009 | Ewers et al. |
| 7,601,195 B2 | 10/2009 | Ichikawa |
| 7,608,099 B2 | 10/2009 | Johnson et al. |
| 7,611,534 B2 | 11/2009 | Kapadia et al. |
| 7,618,446 B2 | 11/2009 | Andersen et al. |
| 7,622,276 B2 | 11/2009 | Cunanan et al. |
| 7,625,403 B2 | 12/2009 | Krivoruchko |
| 7,628,802 B2 | 12/2009 | White et al. |
| 7,628,803 B2 | 12/2009 | Pavcnik et al. |
| 7,632,296 B2 | 12/2009 | Malewicz |
| 7,632,298 B2 | 12/2009 | Hijlkema et al. |
| 7,635,386 B1 | 12/2009 | Gammie |
| 7,641,687 B2 | 1/2010 | Chinn et al. |
| 7,651,519 B2 | 1/2010 | Dittman |
| 7,655,034 B2 | 2/2010 | Mitchell et al. |
| 7,674,282 B2 | 3/2010 | Wu et al. |
| 7,682,390 B2 | 3/2010 | Seguin |
| 7,704,222 B2 | 4/2010 | Wilk et al. |
| 7,704,277 B2 | 4/2010 | Zakay et al. |
| 7,708,775 B2 | 5/2010 | Rowe et al. |
| 7,712,606 B2 | 5/2010 | Salahieh et al. |
| 7,715,903 B2 | 5/2010 | Hartley et al. |
| 7,717,955 B2 | 5/2010 | Lane et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,722,671 B1 | 5/2010 | Carlyle et al. |
| 7,731,742 B2 | 6/2010 | Schlick et al. |
| 7,735,493 B2 | 6/2010 | Van Der Burg et al. |
| 7,736,327 B2 | 6/2010 | Wilk et al. |
| 7,736,388 B2 | 6/2010 | Goldfarb et al. |
| 7,743,481 B2 | 6/2010 | Lafont et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,771,463 B2 | 8/2010 | Ton et al. |
| 7,771,467 B2 | 8/2010 | Svensson |
| 7,776,083 B2 | 8/2010 | Vesely |
| 7,780,725 B2 | 8/2010 | Haug et al. |
| 7,780,726 B2 | 8/2010 | Seguin |
| 7,785,360 B2 | 8/2010 | Freitag |
| 7,794,487 B2 | 9/2010 | Majercak et al. |
| 7,799,046 B2 | 9/2010 | White et al. |
| 7,799,065 B2 | 9/2010 | Pappas |
| 7,803,185 B2 | 9/2010 | Gabbay |
| 7,806,919 B2 | 10/2010 | Bloom et al. |
| 7,823,267 B2 | 11/2010 | Bolduc |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,837,727 B2 | 11/2010 | Goetz et al. |
| 7,846,203 B2 | 12/2010 | Cribier |
| 7,846,204 B2 | 12/2010 | Letac et al. |
| 7,854,758 B2 | 12/2010 | Taheri |
| 7,857,845 B2 | 12/2010 | Stacchino et al. |
| 7,862,602 B2 | 1/2011 | Licata et al. |
| 7,867,274 B2 | 1/2011 | Hill et al. |
| 7,887,583 B2 | 2/2011 | Macoviak |
| 7,892,276 B2 | 2/2011 | Stocker et al. |
| 7,892,292 B2 | 2/2011 | Stack et al. |
| 7,896,913 B2 | 3/2011 | Damm et al. |
| 7,896,915 B2 | 3/2011 | Guyenot et al. |
| 7,914,569 B2 | 3/2011 | Nguyen et al. |
| 7,914,574 B2 | 3/2011 | Schmid et al. |
| 7,914,575 B2 | 3/2011 | Guyenot et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,947,075 B2 | 5/2011 | Goetz et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |

(56) References Cited

U.S. PATENT DOCUMENTS

| | | | |
|---|---|---|---|
| 7,967,853 B2 | 6/2011 | Eidenschink et al. |
| 7,972,359 B2 | 7/2011 | Kreidler |
| 7,972,376 B1 | 7/2011 | Dove et al. |
| 7,972,378 B2 | 7/2011 | Tabor et al. |
| 7,988,724 B2 | 8/2011 | Salahieh et al. |
| 7,993,386 B2 | 8/2011 | Elliott |
| 8,002,824 B2 | 8/2011 | Jenson et al. |
| 8,002,825 B2 | 8/2011 | Letac et al. |
| 8,012,198 B2 | 9/2011 | Hill et al. |
| 8,021,421 B2 | 9/2011 | Fogarty et al. |
| RE42,818 E | 10/2011 | Cali et al. |
| RE42,857 E | 10/2011 | Cali et al. |
| 8,038,704 B2 | 10/2011 | Sherburne |
| 8,038,709 B2 | 10/2011 | Palasis et al. |
| 8,043,450 B2 | 10/2011 | Cali et al. |
| 8,048,153 B2 | 11/2011 | Salahieh et al. |
| 8,052,715 B2 | 11/2011 | Quinn et al. |
| 8,052,749 B2 | 11/2011 | Salahieh et al. |
| 8,052,750 B2 | 11/2011 | Tuval et al. |
| 8,057,540 B2 | 11/2011 | Letac et al. |
| 8,062,355 B2 | 11/2011 | Figulla et al. |
| 8,062,536 B2 | 11/2011 | Liu et al. |
| 8,062,537 B2 | 11/2011 | Tuominen et al. |
| 8,062,749 B2 | 11/2011 | Shelestak et al. |
| 8,070,799 B2 | 12/2011 | Righini et al. |
| 8,075,641 B2 | 12/2011 | Aravanis et al. |
| 8,083,788 B2 | 12/2011 | Acosta et al. |
| 8,092,518 B2 | 1/2012 | Schreck |
| 8,092,520 B2 | 1/2012 | Quadri |
| 8,092,521 B2 | 1/2012 | Figulla et al. |
| 8,128,676 B2 | 3/2012 | Cummings |
| 8,128,681 B2 | 3/2012 | Shoemaker et al. |
| 8,133,217 B2 | 3/2012 | Stokes et al. |
| 8,133,270 B2 | 3/2012 | Kheradvar et al. |
| 8,136,659 B2 | 3/2012 | Salahieh et al. |
| 8,137,394 B2 | 3/2012 | Stocker et al. |
| 8,137,398 B2 | 3/2012 | Tuval et al. |
| 8,147,534 B2 | 4/2012 | Berez et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,206,437 B2 | 6/2012 | Bonhoeffer et al. |
| 8,211,107 B2 | 7/2012 | Parks et al. |
| 8,216,174 B2 | 7/2012 | Wilk et al. |
| 8,216,301 B2 | 7/2012 | Bonhoeffer et al. |
| 8,221,493 B2 | 7/2012 | Boyle et al. |
| 8,226,707 B2 | 7/2012 | White |
| 8,226,710 B2 | 7/2012 | Nguyen et al. |
| 8,230,717 B2 | 7/2012 | Matonick |
| 8,231,670 B2 | 7/2012 | Salahieh et al. |
| 8,236,049 B2 | 8/2012 | Rowe et al. |
| 8,236,241 B2 | 8/2012 | Carpentier et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,303,653 B2 | 11/2012 | Bonhoeffer et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,136 B2 | 1/2013 | Howat et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,999 B2 | 1/2013 | Kheradvar et al. |
| 8,357,387 B2 | 1/2013 | Dove et al. |
| 8,366,767 B2 | 2/2013 | Zhang |
| 8,372,134 B2 | 2/2013 | Schlick et al. |
| 8,376,865 B2 | 2/2013 | Forster et al. |
| 8,377,117 B2 | 2/2013 | Keidar et al. |
| 8,382,822 B2 | 2/2013 | Pavcnik et al. |
| 8,398,704 B2 | 3/2013 | Straubinger et al. |
| 8,398,708 B2 | 3/2013 | Meiri et al. |
| 8,403,983 B2 | 3/2013 | Quadri et al. |
| 8,414,641 B2 | 4/2013 | Stocker et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,439,961 B2 | 5/2013 | Jagger et al. |
| 8,445,278 B2 | 5/2013 | Everaerts et al. |
| 8,460,365 B2 | 6/2013 | Haverkost et al. |
| 8,465,540 B2 | 6/2013 | Straubinger et al. |
| 8,468,667 B2 | 6/2013 | Straubinger et al. |
| 8,470,023 B2 | 6/2013 | Eidenschink et al. |
| 8,491,650 B2 | 7/2013 | Wiemeyer et al. |
| 8,512,394 B2 | 8/2013 | Schmid et al. |
| 8,512,399 B2 | 8/2013 | Lafontaine |
| 8,512,400 B2 | 8/2013 | Tran et al. |
| 8,512,401 B2 | 8/2013 | Murray, III et al. |
| 8,523,936 B2 | 9/2013 | Schmid et al. |
| 8,535,368 B2 | 9/2013 | Headley, Jr. et al. |
| 8,540,762 B2 | 9/2013 | Schmid et al. |
| 8,545,547 B2 | 10/2013 | Schmid et al. |
| 8,545,552 B2 | 10/2013 | Garrison et al. |
| 8,551,160 B2 | 10/2013 | Figulla et al. |
| 8,556,880 B2 | 10/2013 | Freyman et al. |
| 8,556,966 B2 | 10/2013 | Jenson |
| 8,568,475 B2 | 10/2013 | Nguyen et al. |
| 8,579,936 B2 | 11/2013 | Abbott et al. |
| 8,579,962 B2 | 11/2013 | Salahieh et al. |
| 8,579,965 B2 | 11/2013 | Bonhoeffer et al. |
| 8,585,756 B2 | 11/2013 | Bonhoeffer et al. |
| 8,585,759 B2 | 11/2013 | Bumbalough |
| 8,591,570 B2 | 11/2013 | Revuelta et al. |
| 8,597,226 B2 | 12/2013 | Wilk et al. |
| 8,603,159 B2 | 12/2013 | Seguin et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,075 B2 | 1/2014 | Murray, III et al. |
| 8,623,076 B2 | 1/2014 | Salahieh et al. |
| 8,623,078 B2 | 1/2014 | Salahieh et al. |
| 8,628,562 B2 | 1/2014 | Cummings |
| 8,628,571 B1 | 1/2014 | Hacohen et al. |
| 8,647,381 B2 | 2/2014 | Essinger et al. |
| 8,668,733 B2 | 3/2014 | Haug et al. |
| 8,672,997 B2 | 3/2014 | Drasler et al. |
| 8,679,174 B2 | 3/2014 | Ottma et al. |
| 8,685,077 B2 | 4/2014 | Laske et al. |
| 8,696,743 B2 | 4/2014 | Holecek et al. |
| 8,721,713 B2 | 5/2014 | Tower et al. |
| 8,721,717 B2 | 5/2014 | Shoemaker et al. |
| 8,734,508 B2 | 5/2014 | Hastings et al. |
| 8,758,430 B2 | 6/2014 | Ferrari et al. |
| 8,764,818 B2 | 7/2014 | Gregg |
| 8,778,020 B2 | 7/2014 | Gregg et al. |
| 8,790,395 B2 | 7/2014 | Straubinger et al. |
| 8,795,305 B2 | 8/2014 | Martin et al. |
| 8,795,356 B2 | 8/2014 | Quadri et al. |
| 8,808,356 B2 | 8/2014 | Braido et al. |
| 8,808,364 B2 | 8/2014 | Palasis et al. |
| RE45,130 E | 9/2014 | Figulla et al. |
| 8,828,078 B2 | 9/2014 | Salahieh et al. |
| 8,828,079 B2 | 9/2014 | Thielen et al. |
| 8,840,662 B2 | 9/2014 | Salahieh et al. |
| 8,840,663 B2 | 9/2014 | Salahieh et al. |
| 8,845,721 B2 | 9/2014 | Braido et al. |
| 8,851,286 B2 | 10/2014 | Chang et al. |
| 8,852,272 B2 | 10/2014 | Gross et al. |
| 8,858,620 B2 | 10/2014 | Salahieh et al. |
| 8,894,703 B2 | 11/2014 | Salahieh et al. |
| 8,932,349 B2 | 1/2015 | Jenson et al. |
| 8,940,014 B2 | 1/2015 | Gamarra et al. |
| 8,951,243 B2 | 2/2015 | Crisostomo et al. |
| 8,951,299 B2 | 2/2015 | Paul et al. |
| 8,956,383 B2 | 2/2015 | Aklog et al. |
| 8,992,608 B2 | 3/2015 | Haug et al. |
| 8,998,976 B2 | 4/2015 | Gregg et al. |

(56) References Cited

U.S. PATENT DOCUMENTS

| | | | |
|---|---|---|---|
| 9,005,273 | B2 | 4/2015 | Salahieh et al. |
| 9,011,521 | B2 | 4/2015 | Haug et al. |
| 9,023,099 | B2 | 5/2015 | Duffy et al. |
| 9,028,542 | B2 | 5/2015 | Hill et al. |
| 9,039,756 | B2 | 5/2015 | White |
| 9,044,318 | B2 | 6/2015 | Straubinger et al. |
| 9,131,926 | B2 | 9/2015 | Crisostomo et al. |
| 9,138,315 | B2 | 9/2015 | Straubinger et al. |
| 9,149,358 | B2 | 10/2015 | Tabor et al. |
| 9,168,130 | B2 | 10/2015 | Straubinger et al. |
| 9,168,131 | B2 | 10/2015 | Yohanan et al. |
| 9,168,136 | B2 | 10/2015 | Yang et al. |
| RE45,790 | E | 11/2015 | Figulla et al. |
| 9,180,005 | B1 | 11/2015 | Lashinski et al. |
| 9,186,482 | B2 | 11/2015 | Dorn |
| 9,211,266 | B2 | 12/2015 | Iwazawa et al. |
| 9,216,082 | B2 | 12/2015 | Von Segesser et al. |
| 9,248,037 | B2 | 2/2016 | Roeder et al. |
| 9,265,608 | B2 | 2/2016 | Miller et al. |
| 9,277,991 | B2 | 3/2016 | Salahieh et al. |
| 9,277,993 | B2 | 3/2016 | Gamarra et al. |
| 9,295,551 | B2 | 3/2016 | Straubinger et al. |
| 9,301,840 | B2 | 4/2016 | Nguyen et al. |
| 9,301,843 | B2 | 4/2016 | Richardson et al. |
| 9,308,085 | B2 | 4/2016 | Salahieh et al. |
| 9,320,599 | B2 | 4/2016 | Salahieh et al. |
| 9,326,853 | B2 | 5/2016 | Olson et al. |
| 9,358,106 | B2 | 6/2016 | Salahieh et al. |
| 9,358,110 | B2 | 6/2016 | Paul et al. |
| 9,370,419 | B2 | 6/2016 | Hill et al. |
| 9,370,421 | B2 | 6/2016 | Crisostomo et al. |
| 9,387,076 | B2 | 7/2016 | Paul et al. |
| 9,393,094 | B2 | 7/2016 | Salahieh et al. |
| 9,393,113 | B2 | 7/2016 | Salahieh et al. |
| 9,393,114 | B2 | 7/2016 | Sutton et al. |
| 9,393,115 | B2 | 7/2016 | Tabor et al. |
| 9,415,567 | B2 | 8/2016 | Sogard et al. |
| 9,421,083 | B2 | 8/2016 | Eidenschink et al. |
| 9,439,759 | B2 | 9/2016 | Straubinger et al. |
| 9,463,084 | B2 | 10/2016 | Stinson |
| 9,474,598 | B2 | 10/2016 | Gregg et al. |
| 9,474,609 | B2 | 10/2016 | Haverkost et al. |
| 9,492,276 | B2 | 11/2016 | Lee et al. |
| 9,510,945 | B2 | 12/2016 | Sutton et al. |
| 9,510,947 | B2 | 12/2016 | Straubinger et al. |
| 9,526,609 | B2 | 12/2016 | Salahieh et al. |
| 9,532,872 | B2 | 1/2017 | Salahieh et al. |
| 9,539,091 | B2 | 1/2017 | Yang et al. |
| 9,554,924 | B2 | 1/2017 | Schlick et al. |
| 9,597,432 | B2 | 3/2017 | Nakamura |
| 9,649,212 | B2 | 5/2017 | Fargahi |
| 9,675,413 | B2 | 6/2017 | Deem et al. |
| 9,717,593 | B2 | 8/2017 | Alkhatib et al. |
| 9,744,031 | B2 | 8/2017 | Girard et al. |
| D800,908 | S | 10/2017 | Hariton et al. |
| 9,775,709 | B2 | 10/2017 | Miller et al. |
| 9,788,945 | B2 | 10/2017 | Ottma et al. |
| 9,861,476 | B2 | 1/2018 | Salahieh et al. |
| 9,867,694 | B2 | 1/2018 | Girard et al. |
| 9,867,699 | B2 | 1/2018 | Straubinger et al. |
| 9,872,768 | B2 | 1/2018 | Paul et al. |
| 9,878,127 | B2 | 1/2018 | Damm et al. |
| 9,889,002 | B2 | 2/2018 | Bonhoeffer et al. |
| 9,901,445 | B2 | 2/2018 | Backus et al. |
| 9,918,835 | B2 | 3/2018 | Guyenot et al. |
| 9,949,824 | B2 | 4/2018 | Bonhoeffer et al. |
| 9,956,075 | B2 | 5/2018 | Salahieh et al. |
| 9,968,761 | B2 | 5/2018 | Brecker |
| 9,987,133 | B2 | 6/2018 | Straubinger et al. |
| 10,092,324 | B2 | 10/2018 | Gillespie et al. |
| 10,143,552 | B2 | 12/2018 | Wallace et al. |
| 10,154,901 | B2 | 12/2018 | Straubinger et al. |
| 10,321,987 | B2 | 6/2019 | Wang et al. |
| 10,363,134 | B2 | 7/2019 | Figulla et al. |
| 10,543,084 | B2 | 1/2020 | Guyenot et al. |
| 10,575,947 | B2 | 3/2020 | Straubinger et al. |
| 10,638,918 | B2 | 5/2020 | Atarot et al. |
| 10,653,427 | B2 | 5/2020 | Goldfarb et al. |
| 10,702,382 | B2 | 7/2020 | Straubinger et al. |
| 10,709,555 | B2 | 7/2020 | Schreck et al. |
| 10,856,978 | B2 | 12/2020 | Straubinger et al. |
| 10,856,987 | B2 | 12/2020 | Cabiri et al. |
| 11,065,138 | B2 | 7/2021 | Schreck et al. |
| 11,147,669 | B2 | 10/2021 | Straubinger et al. |
| 11,154,398 | B2 | 10/2021 | Straubinger et al. |
| 11,185,405 | B2 | 11/2021 | Girard et al. |
| 11,197,754 | B2 | 12/2021 | Saffari et al. |
| 11,266,497 | B2 | 3/2022 | Cao et al. |
| 11,357,624 | B2 | 6/2022 | Guyenot et al. |
| 11,911,264 | B2 | 2/2024 | Chau et al. |
| 11,951,005 | B2 | 4/2024 | Gross et al. |
| 12,121,461 | B2 | 10/2024 | Schreck et al. |
| 12,171,658 | B2 | 12/2024 | Chu et al. |
| 12,232,957 | B2 | 2/2025 | Straubinger et al. |
| 12,318,281 | B2 | 6/2025 | Girard et al. |
| 12,343,255 | B2 | 7/2025 | Schreck et al. |
| 2001/0000041 | A1 | 3/2001 | Selmon et al. |
| 2001/0001314 | A1 | 5/2001 | Davison et al. |
| 2001/0002445 | A1 | 5/2001 | Vesely |
| 2001/0004683 | A1 | 6/2001 | Gambale et al. |
| 2001/0004690 | A1 | 6/2001 | Gambale et al. |
| 2001/0004699 | A1 | 6/2001 | Gittings et al. |
| 2001/0007956 | A1 | 7/2001 | Letac et al. |
| 2001/0008969 | A1 | 7/2001 | Evans et al. |
| 2001/0010017 | A1 | 7/2001 | Letac et al. |
| 2001/0011187 | A1 | 8/2001 | Pavcnik et al. |
| 2001/0011189 | A1 | 8/2001 | Drasler et al. |
| 2001/0012948 | A1 | 8/2001 | Vanney |
| 2001/0014813 | A1 | 8/2001 | Saadat et al. |
| 2001/0016700 | A1 | 8/2001 | Eno et al. |
| 2001/0018596 | A1 | 8/2001 | Selmon et al. |
| 2001/0020172 | A1 | 9/2001 | Selmon et al. |
| 2001/0021872 | A1 | 9/2001 | Bailey et al. |
| 2001/0025196 | A1 | 9/2001 | Chinn et al. |
| 2001/0025643 | A1 | 10/2001 | Foley |
| 2001/0027287 | A1 | 10/2001 | Shmulewitz et al. |
| 2001/0027338 | A1 | 10/2001 | Greenberg |
| 2001/0027339 | A1 | 10/2001 | Boatman et al. |
| 2001/0029385 | A1 | 10/2001 | Shennib et al. |
| 2001/0032013 | A1 | 10/2001 | Marton |
| 2001/0034547 | A1 | 10/2001 | Hall et al. |
| 2001/0037117 | A1 | 11/2001 | Gambale et al. |
| 2001/0037141 | A1 | 11/2001 | Yee et al. |
| 2001/0037149 | A1 | 11/2001 | Wilk |
| 2001/0039426 | A1 | 11/2001 | Makower et al. |
| 2001/0039445 | A1 | 11/2001 | Hall et al. |
| 2001/0039450 | A1 | 11/2001 | Pavcnik et al. |
| 2001/0041902 | A1 | 11/2001 | Lepulu et al. |
| 2001/0041928 | A1 | 11/2001 | Pavcnik et al. |
| 2001/0041930 | A1 | 11/2001 | Globerman et al. |
| 2001/0044631 | A1 | 11/2001 | Akin et al. |
| 2001/0044634 | A1 | 11/2001 | Don Michael et al. |
| 2001/0044647 | A1 | 11/2001 | Pinchuk et al. |
| 2001/0044652 | A1 | 11/2001 | Moore |
| 2001/0044656 | A1 | 11/2001 | Williamson, IV et al. |
| 2001/0047165 | A1 | 11/2001 | Makower et al. |
| 2001/0049523 | A1 | 12/2001 | DeVore et al. |
| 2001/0051822 | A1 | 12/2001 | Stack et al. |
| 2001/0053930 | A1 | 12/2001 | Kugler et al. |
| 2001/0053932 | A1 | 12/2001 | Phelps et al. |
| 2002/0002349 | A1 | 1/2002 | Flaherty et al. |
| 2002/0002396 | A1 | 1/2002 | Fulkerson |
| 2002/0002401 | A1 | 1/2002 | McGuckin, Jr. et al. |
| 2002/0004662 | A1 | 1/2002 | Wilk |
| 2002/0004663 | A1 | 1/2002 | Gittings et al. |
| 2002/0007138 | A1 | 1/2002 | Wilk et al. |
| 2002/0010489 | A1 | 1/2002 | Grayzel et al. |
| 2002/0010508 | A1 | 1/2002 | Chobotov |
| 2002/0026233 | A1 | 2/2002 | Shaknovich |
| 2002/0029014 | A1 | 3/2002 | Jayaraman |
| 2002/0029079 | A1 | 3/2002 | Kim et al. |
| 2002/0029981 | A1 | 3/2002 | Nigam |
| 2002/0032476 | A1 | 3/2002 | Gambale et al. |
| 2002/0032478 | A1 | 3/2002 | Boekstegers et al. |

(56) References Cited

U.S. PATENT DOCUMENTS

| | | |
|---|---|---|
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |
| 2002/0045928 A1 | 4/2002 | Boekstegers |
| 2002/0045929 A1 | 4/2002 | Diaz |
| 2002/0049486 A1 | 4/2002 | Knudson et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055772 A1 | 5/2002 | McGuckin, Jr. et al. |
| 2002/0055774 A1 | 5/2002 | Liddicoat |
| 2002/0055775 A1 | 5/2002 | Carpentier et al. |
| 2002/0058897 A1 | 5/2002 | Renati |
| 2002/0058987 A1 | 5/2002 | Butaric et al. |
| 2002/0058993 A1 | 5/2002 | Landau et al. |
| 2002/0058995 A1 | 5/2002 | Stevens |
| 2002/0062146 A1 | 5/2002 | Makower et al. |
| 2002/0065478 A1 | 5/2002 | Knudson et al. |
| 2002/0065485 A1 | 5/2002 | DuBois et al. |
| 2002/0072699 A1 | 6/2002 | Knudson et al. |
| 2002/0072789 A1 | 6/2002 | Hackett et al. |
| 2002/0077566 A1 | 6/2002 | Laroya et al. |
| 2002/0077654 A1 | 6/2002 | Javier, Jr. et al. |
| 2002/0077696 A1 | 6/2002 | Zadno-Azizi et al. |
| 2002/0082584 A1 | 6/2002 | Rosenman et al. |
| 2002/0082585 A1 | 6/2002 | Carroll et al. |
| 2002/0082609 A1 | 6/2002 | Green |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095173 A1 | 7/2002 | Mazzocchi et al. |
| 2002/0095206 A1 | 7/2002 | Addonizio et al. |
| 2002/0095209 A1 | 7/2002 | Zadno-Azizi et al. |
| 2002/0099405 A1 | 7/2002 | Yurek et al. |
| 2002/0099439 A1 | 7/2002 | Schwartz et al. |
| 2002/0100484 A1 | 8/2002 | Hall et al. |
| 2002/0103533 A1 | 8/2002 | Langberg et al. |
| 2002/0107565 A1 | 8/2002 | Greenhalgh |
| 2002/0111627 A1 | 8/2002 | Vincent-Prestigiacomo |
| 2002/0111665 A1 | 8/2002 | Lauterjung |
| 2002/0111668 A1 | 8/2002 | Smith |
| 2002/0111672 A1 | 8/2002 | Kim et al. |
| 2002/0111674 A1 | 8/2002 | Chouinard et al. |
| 2002/0117789 A1 | 8/2002 | Childers et al. |
| 2002/0120322 A1 | 8/2002 | Thompson et al. |
| 2002/0120323 A1 | 8/2002 | Thompson et al. |
| 2002/0120328 A1 | 8/2002 | Pathak et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0123802 A1 | 9/2002 | Snyders |
| 2002/0128552 A1 | 9/2002 | Nowlin et al. |
| 2002/0133183 A1 | 9/2002 | Lentz et al. |
| 2002/0133226 A1 | 9/2002 | Marquez et al. |
| 2002/0138087 A1 | 9/2002 | Shennib et al. |
| 2002/0138138 A1 | 9/2002 | Yang |
| 2002/0143285 A1 | 10/2002 | Eno et al. |
| 2002/0143289 A1 | 10/2002 | Ellis et al. |
| 2002/0143387 A1 | 10/2002 | Soetikno et al. |
| 2002/0144696 A1 | 10/2002 | Sharkawy et al. |
| 2002/0151913 A1 | 10/2002 | Berg et al. |
| 2002/0151970 A1 | 10/2002 | Garrison et al. |
| 2002/0156522 A1 | 10/2002 | Ivancev et al. |
| 2002/0161377 A1 | 10/2002 | Rabkin |
| 2002/0161383 A1 | 10/2002 | Akin et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0161424 A1 | 10/2002 | Rapacki et al. |
| 2002/0161426 A1 | 10/2002 | Iancea |
| 2002/0165479 A1 | 11/2002 | Wilk |
| 2002/0165576 A1 | 11/2002 | Boyle et al. |
| 2002/0165606 A1 | 11/2002 | Wolf et al. |
| 2002/0173842 A1 | 11/2002 | Buchanan |
| 2002/0177766 A1 | 11/2002 | Mogul |
| 2002/0177772 A1 | 11/2002 | Altman et al. |
| 2002/0177840 A1 | 11/2002 | Farnholtz |
| 2002/0177894 A1 | 11/2002 | Acosta et al. |
| 2002/0179098 A1 | 12/2002 | Makower et al. |
| 2002/0183716 A1 | 12/2002 | Herweck et al. |
| 2002/0183781 A1 | 12/2002 | Casey et al. |
| 2002/0186558 A1 | 12/2002 | Plank et al. |
| 2002/0188341 A1 | 12/2002 | Elliott |
| 2002/0188344 A1 | 12/2002 | Bolea et al. |
| 2002/0193782 A1 | 12/2002 | Ellis et al. |
| 2002/0193871 A1 | 12/2002 | Beyersdorf et al. |
| 2002/0198594 A1 | 12/2002 | Schreck |
| 2003/0004541 A1 | 1/2003 | Linder et al. |
| 2003/0004560 A1 | 1/2003 | Chobotov et al. |
| 2003/0009189 A1 | 1/2003 | Gilson et al. |
| 2003/0014104 A1 | 1/2003 | Cribier |
| 2003/0018377 A1 | 1/2003 | Berg et al. |
| 2003/0018379 A1 | 1/2003 | Knudson et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0028213 A1 | 2/2003 | Thill et al. |
| 2003/0028247 A1 | 2/2003 | Cali |
| 2003/0033001 A1 | 2/2003 | Igaki |
| 2003/0036791 A1 | 2/2003 | Philipp et al. |
| 2003/0036795 A1 | 2/2003 | Andersen et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0042186 A1 | 3/2003 | Boyle |
| 2003/0044315 A1 | 3/2003 | Boekstegers |
| 2003/0045828 A1 | 3/2003 | Wilk |
| 2003/0050694 A1 | 3/2003 | Yang et al. |
| 2003/0055371 A1 | 3/2003 | Wolf et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0065386 A1 | 4/2003 | Weadock |
| 2003/0069492 A1 | 4/2003 | Abrams et al. |
| 2003/0069646 A1 | 4/2003 | Stinson |
| 2003/0070944 A1 | 4/2003 | Nigam |
| 2003/0073973 A1 | 4/2003 | Evans et al. |
| 2003/0074058 A1 | 4/2003 | Sherry |
| 2003/0078561 A1 | 4/2003 | Gambale et al. |
| 2003/0078652 A1 | 4/2003 | Sutherland |
| 2003/0083730 A1 | 5/2003 | Stinson |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0100920 A1 | 5/2003 | Akin et al. |
| 2003/0105514 A1 | 6/2003 | Phelps et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0120195 A1 | 6/2003 | Milo et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0130746 A1 | 7/2003 | Ashworth et al. |
| 2003/0135257 A1 | 7/2003 | Taheri |
| 2003/0139796 A1 | 7/2003 | Sequin et al. |
| 2003/0139798 A1 | 7/2003 | Brown et al. |
| 2003/0139803 A1 | 7/2003 | Sequin et al. |
| 2003/0139804 A1 | 7/2003 | Hankh et al. |
| 2003/0144657 A1 | 7/2003 | Bowe et al. |
| 2003/0144732 A1 | 7/2003 | Cosgrove et al. |
| 2003/0149474 A1 | 8/2003 | Becker |
| 2003/0149475 A1 | 8/2003 | Hyodoh et al. |
| 2003/0149476 A1 | 8/2003 | Damm et al. |
| 2003/0149477 A1 | 8/2003 | Gabbay |
| 2003/0149478 A1 | 8/2003 | Figulla et al. |

(56)             References Cited

U.S. PATENT DOCUMENTS

| | | |
|---|---|---|
| 2003/0153971 A1 | 8/2003 | Chandrasekaran |
| 2003/0153974 A1 | 8/2003 | Spenser et al. |
| 2003/0158573 A1 | 8/2003 | Gittings et al. |
| 2003/0158595 A1 | 8/2003 | Randall et al. |
| 2003/0163193 A1 | 8/2003 | Widenhouse |
| 2003/0163198 A1 | 8/2003 | Morra et al. |
| 2003/0165352 A1 | 9/2003 | Ibrahim et al. |
| 2003/0171803 A1 | 9/2003 | Shimon |
| 2003/0171805 A1 | 9/2003 | Berg et al. |
| 2003/0176884 A1 | 9/2003 | Berrada et al. |
| 2003/0181850 A1 | 9/2003 | Diamond et al. |
| 2003/0181938 A1 | 9/2003 | Roth et al. |
| 2003/0181942 A1 | 9/2003 | Sutton et al. |
| 2003/0187495 A1 | 10/2003 | Cully et al. |
| 2003/0191449 A1 | 10/2003 | Nash et al. |
| 2003/0191516 A1 | 10/2003 | Weldon et al. |
| 2003/0191519 A1 | 10/2003 | Lombardi et al. |
| 2003/0191526 A1 | 10/2003 | Van Tassel et al. |
| 2003/0195457 A1 | 10/2003 | LaFontaine et al. |
| 2003/0195458 A1 | 10/2003 | Phelps et al. |
| 2003/0195609 A1 | 10/2003 | Berenstein et al. |
| 2003/0195620 A1 | 10/2003 | Huynh et al. |
| 2003/0198722 A1 | 10/2003 | Johnston, Jr. et al. |
| 2003/0199759 A1 | 10/2003 | Richard |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0204160 A1 | 10/2003 | Kamm et al. |
| 2003/0204249 A1 | 10/2003 | Letort |
| 2003/0208224 A1 | 11/2003 | Broome |
| 2003/0212410 A1 | 11/2003 | Stenzel et al. |
| 2003/0212413 A1 | 11/2003 | Wilk |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216678 A1 | 11/2003 | March et al. |
| 2003/0216679 A1 | 11/2003 | Wolf et al. |
| 2003/0216774 A1 | 11/2003 | Larson |
| 2003/0220661 A1 | 11/2003 | Mowry et al. |
| 2003/0220667 A1 | 11/2003 | Van Der Burg et al. |
| 2003/0225445 A1 | 12/2003 | Derus et al. |
| 2003/0229366 A1 | 12/2003 | Reggie et al. |
| 2003/0229390 A1 | 12/2003 | Ashton et al. |
| 2003/0233117 A1 | 12/2003 | Adams et al. |
| 2003/0236542 A1 | 12/2003 | Makower |
| 2003/0236567 A1 | 12/2003 | Elliot |
| 2003/0236568 A1 | 12/2003 | Hojeibane et al. |
| 2003/0236570 A1 | 12/2003 | Cook et al. |
| 2004/0004926 A1 | 1/2004 | Maeda |
| 2004/0006298 A1 | 1/2004 | Wilk |
| 2004/0006380 A1 | 1/2004 | Buck et al. |
| 2004/0015225 A1 | 1/2004 | Kim et al. |
| 2004/0015228 A1 | 1/2004 | Lombardi et al. |
| 2004/0018651 A1 | 1/2004 | Nadeau |
| 2004/0019348 A1 | 1/2004 | Stevens et al. |
| 2004/0019374 A1 | 1/2004 | Hojeibane et al. |
| 2004/0026389 A1 | 2/2004 | Kessler et al. |
| 2004/0033364 A1 | 2/2004 | Spiridigliozzi et al. |
| 2004/0034411 A1 | 2/2004 | Quijano et al. |
| 2004/0037946 A1 | 2/2004 | Morra et al. |
| 2004/0039343 A1 | 2/2004 | Eppstein et al. |
| 2004/0039436 A1 | 2/2004 | Spenser et al. |
| 2004/0044350 A1 | 3/2004 | Martin et al. |
| 2004/0044361 A1 | 3/2004 | Frazier et al. |
| 2004/0044392 A1 | 3/2004 | Von Oepen |
| 2004/0044400 A1 | 3/2004 | Cheng et al. |
| 2004/0044402 A1 | 3/2004 | Jung et al. |
| 2004/0049204 A1 | 3/2004 | Harari et al. |
| 2004/0049207 A1 | 3/2004 | Goldfarb et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0058097 A1 | 3/2004 | Weder |
| 2004/0059280 A1 | 3/2004 | Makower et al. |
| 2004/0059407 A1 | 3/2004 | Escamilla et al. |
| 2004/0059409 A1 | 3/2004 | Stenzel |
| 2004/0059429 A1 | 3/2004 | Amin et al. |
| 2004/0073157 A1 | 4/2004 | Knudson et al. |
| 2004/0073198 A1 | 4/2004 | Gilson et al. |
| 2004/0073238 A1 | 4/2004 | Makower |
| 2004/0073289 A1 | 4/2004 | Hartley |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0078950 A1 | 4/2004 | Schreck |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088042 A1 | 5/2004 | Kim et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093016 A1 | 5/2004 | Root et al. |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0102855 A1 | 5/2004 | Shank |
| 2004/0106931 A1 | 6/2004 | Guiles et al. |
| 2004/0106976 A1 | 6/2004 | Bailey et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127847 A1 | 7/2004 | DuBois et al. |
| 2004/0127912 A1 | 7/2004 | Rabkin et al. |
| 2004/0127936 A1 | 7/2004 | Salahieh et al. |
| 2004/0127979 A1 | 7/2004 | Wilson et al. |
| 2004/0127982 A1 | 7/2004 | Machold et al. |
| 2004/0133154 A1 | 7/2004 | Flaherty et al. |
| 2004/0133225 A1 | 7/2004 | Makower |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0138745 A1 | 7/2004 | Macoviak et al. |
| 2004/0147868 A1 | 7/2004 | Bardsley et al. |
| 2004/0147869 A1 | 7/2004 | Wolf et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0153145 A1 | 8/2004 | Simionescu et al. |
| 2004/0153146 A1 | 8/2004 | Lashinski et al. |
| 2004/0158143 A1 | 8/2004 | Flaherty et al. |
| 2004/0158277 A1 | 8/2004 | Lowe et al. |
| 2004/0163094 A1 | 8/2004 | Matsui et al. |
| 2004/0167444 A1 | 8/2004 | Laroya et al. |
| 2004/0167565 A1 | 8/2004 | Beulke et al. |
| 2004/0167573 A1 | 8/2004 | Williamson, IV et al. |
| 2004/0167619 A1 | 8/2004 | Case et al. |
| 2004/0167620 A1 | 8/2004 | Ortiz et al. |
| 2004/0168691 A1 | 9/2004 | Sharkawy et al. |
| 2004/0176791 A1 | 9/2004 | Lim et al. |
| 2004/0181140 A1 | 9/2004 | Falwell et al. |
| 2004/0186378 A1 | 9/2004 | Gesswein |

(56)                References Cited

U.S. PATENT DOCUMENTS

| | | |
|---|---|---|
| 2004/0186507 A1 | 9/2004 | Hall et al. |
| 2004/0186557 A1 | 9/2004 | Gambale et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186587 A1 | 9/2004 | Ahern |
| 2004/0193180 A1 | 9/2004 | Buzzard et al. |
| 2004/0193244 A1 | 9/2004 | Hartley et al. |
| 2004/0193252 A1 | 9/2004 | Perez et al. |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204683 A1 | 10/2004 | McGuckin, Jr. et al. |
| 2004/0204755 A1 | 10/2004 | Robin |
| 2004/0206363 A1 | 10/2004 | McCarthy et al. |
| 2004/0210104 A1 | 10/2004 | Lau et al. |
| 2004/0210190 A1 | 10/2004 | Kohler et al. |
| 2004/0210240 A1 | 10/2004 | Saint |
| 2004/0210301 A1 | 10/2004 | Obermiller |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215317 A1 | 10/2004 | Cummings |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0219180 A1 | 11/2004 | Gambale et al. |
| 2004/0220598 A1 | 11/2004 | Bolduc et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0236418 A1 | 11/2004 | Stevens |
| 2004/0243143 A1 | 12/2004 | Corcoran et al. |
| 2004/0243221 A1 | 12/2004 | Fawzi et al. |
| 2004/0249343 A1 | 12/2004 | Cioanta |
| 2004/0254594 A1 | 12/2004 | Alfaro |
| 2004/0254636 A1 | 12/2004 | Flagle et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0000858 A1 | 1/2005 | Roovers |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0008589 A1 | 1/2005 | Legrand et al. |
| 2005/0009000 A1 | 1/2005 | Wilhelm et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021136 A1 | 1/2005 | Xie et al. |
| 2005/0025857 A1 | 2/2005 | Schoenherr et al. |
| 2005/0027305 A1 | 2/2005 | Shiu et al. |
| 2005/0027348 A1 | 2/2005 | Case et al. |
| 2005/0033220 A1 | 2/2005 | Wilk et al. |
| 2005/0033398 A1 | 2/2005 | Seguin |
| 2005/0033402 A1 | 2/2005 | Cully et al. |
| 2005/0038495 A1 | 2/2005 | Greenan |
| 2005/0038509 A1 | 2/2005 | Ashe |
| 2005/0043585 A1 | 2/2005 | Datta et al. |
| 2005/0043711 A1 | 2/2005 | Corcoran et al. |
| 2005/0043757 A1 | 2/2005 | Arad et al. |
| 2005/0043759 A1 | 2/2005 | Chanduszko |
| 2005/0043760 A1 | 2/2005 | Fogarty et al. |
| 2005/0043781 A1 | 2/2005 | Foley |
| 2005/0043790 A1 | 2/2005 | Seguin |
| 2005/0049674 A1 | 3/2005 | Berra et al. |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060018 A1 | 3/2005 | Dittman |
| 2005/0060029 A1 | 3/2005 | Le et al. |
| 2005/0060030 A1 | 3/2005 | Lashinski et al. |
| 2005/0065594 A1 | 3/2005 | DiMatteo et al. |
| 2005/0070794 A1 | 3/2005 | Deal et al. |
| 2005/0070957 A1 | 3/2005 | Das |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0075776 A1 | 4/2005 | Cho |
| 2005/0084595 A1 | 4/2005 | Shukla et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0090846 A1 | 4/2005 | Pedersen et al. |
| 2005/0090890 A1 | 4/2005 | Wu et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096726 A1 | 5/2005 | Sequin et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096768 A1 | 5/2005 | Huang et al. |
| 2005/0098547 A1 | 5/2005 | Cali et al. |
| 2005/0100580 A1 | 5/2005 | Osborne et al. |
| 2005/0101903 A1 | 5/2005 | Kohler et al. |
| 2005/0101904 A1 | 5/2005 | Wilk |
| 2005/0101968 A1 | 5/2005 | Dadourian |
| 2005/0102020 A1 | 5/2005 | Grayzel et al. |
| 2005/0107822 A1 | 5/2005 | Wasdyke |
| 2005/0107871 A1 | 5/2005 | Realyvasquez et al. |
| 2005/0113902 A1 | 5/2005 | Geiser et al. |
| 2005/0113904 A1 | 5/2005 | Shank et al. |
| 2005/0113910 A1 | 5/2005 | Paniagua et al. |
| 2005/0119688 A1 | 6/2005 | Bergheim |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0131438 A1 | 6/2005 | Cohn |
| 2005/0137499 A1 | 6/2005 | Sheets et al. |
| 2005/0137609 A1 | 6/2005 | Guiraudon |
| 2005/0137681 A1 | 6/2005 | Shoemaker et al. |
| 2005/0137682 A1 | 6/2005 | Justino |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |

(56)  References Cited

U.S. PATENT DOCUMENTS

| | | |
|---|---|---|
| 2005/0149159 A1 | 7/2005 | Andreas et al. |
| 2005/0149166 A1 | 7/2005 | Schaeffer et al. |
| 2005/0149181 A1 | 7/2005 | Eberhardt |
| 2005/0150775 A1 | 7/2005 | Zhang et al. |
| 2005/0159726 A1 | 7/2005 | Evans et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0171597 A1 | 8/2005 | Boatman et al. |
| 2005/0171598 A1 | 8/2005 | Schaeffer |
| 2005/0177227 A1 | 8/2005 | Heim et al. |
| 2005/0182483 A1 | 8/2005 | Osborne et al. |
| 2005/0182486 A1 | 8/2005 | Gabbay |
| 2005/0186349 A1 | 8/2005 | Loper et al. |
| 2005/0187616 A1 | 8/2005 | Realyvasquez |
| 2005/0192527 A1 | 9/2005 | Gharib et al. |
| 2005/0192665 A1 | 9/2005 | Spenser et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0214342 A1 | 9/2005 | Tweden et al. |
| 2005/0222664 A1 | 10/2005 | Parker |
| 2005/0222668 A1 | 10/2005 | Schaeffer et al. |
| 2005/0222674 A1 | 10/2005 | Paine |
| 2005/0228334 A1 | 10/2005 | Knudson et al. |
| 2005/0228472 A1 | 10/2005 | Case et al. |
| 2005/0228495 A1 | 10/2005 | Macoviak |
| 2005/0228496 A1 | 10/2005 | Mensah et al. |
| 2005/0234546 A1 | 10/2005 | Nugent et al. |
| 2005/0240200 A1 | 10/2005 | Bergheim |
| 2005/0240262 A1 | 10/2005 | White |
| 2005/0240263 A1 | 10/2005 | Fogarty et al. |
| 2005/0251243 A1 | 11/2005 | Seppala et al. |
| 2005/0251250 A1 | 11/2005 | Verhoeven et al. |
| 2005/0251251 A1 | 11/2005 | Cribier |
| 2005/0251252 A1 | 11/2005 | Stobie |
| 2005/0256532 A1 | 11/2005 | Nayak et al. |
| 2005/0261759 A1 | 11/2005 | Lambrecht et al. |
| 2005/0267523 A1 | 12/2005 | Devellian et al. |
| 2005/0267560 A1 | 12/2005 | Bates |
| 2005/0267567 A1 | 12/2005 | Shalev |
| 2005/0267573 A9 | 12/2005 | Macoviak et al. |
| 2005/0283231 A1 | 12/2005 | Haug et al. |
| 2005/0283962 A1 | 12/2005 | Boudjemline |
| 2005/0288627 A1 | 12/2005 | Mogul |
| 2005/0288685 A1 | 12/2005 | Gulles et al. |
| 2005/0288706 A1 | 12/2005 | Widomski et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0009842 A1 | 1/2006 | Huynh et al. |
| 2006/0015168 A1 | 1/2006 | Gunderson |
| 2006/0025855 A1 | 2/2006 | Lashinski et al. |
| 2006/0025857 A1 | 2/2006 | Bergheim et al. |
| 2006/0028766 A1 | 2/2006 | Khizroev |
| 2006/0041218 A1 | 2/2006 | Phelps et al. |
| 2006/0047338 A1 | 3/2006 | Jenson et al. |
| 2006/0047343 A1 | 3/2006 | Oviatt et al. |
| 2006/0052736 A1 | 3/2006 | Tweden et al. |
| 2006/0052867 A1 | 3/2006 | Revuelta et al. |
| 2006/0058775 A1 | 3/2006 | Stevens et al. |
| 2006/0058864 A1 | 3/2006 | Schaeffer et al. |
| 2006/0058871 A1 | 3/2006 | Zakay et al. |
| 2006/0058872 A1 | 3/2006 | Salahieh et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0074484 A1 | 4/2006 | Huber |
| 2006/0074485 A1 | 4/2006 | Realyvasquez |
| 2006/0077447 A1 | 4/2006 | Sojian et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0111770 A1 | 5/2006 | Pavcnik et al. |
| 2006/0116757 A1 | 6/2006 | Lashinski et al. |
| 2006/0122692 A1 | 6/2006 | Gilad et al. |
| 2006/0135961 A1 | 6/2006 | Rosenman et al. |
| 2006/0135964 A1 | 6/2006 | Vesely |
| 2006/0136034 A1 | 6/2006 | Modesitt et al. |
| 2006/0142846 A1 | 6/2006 | Pavcnik et al. |
| 2006/0142848 A1 | 6/2006 | Gabbay |
| 2006/0149360 A1 | 7/2006 | Schwammenthal et al. |
| 2006/0155312 A1 | 7/2006 | Levine et al. |
| 2006/0155363 A1 | 7/2006 | LaDuca et al. |
| 2006/0155366 A1 | 7/2006 | LaDuca et al. |
| 2006/0161248 A1 | 7/2006 | Case et al. |
| 2006/0161249 A1 | 7/2006 | Realyvasquez et al. |
| 2006/0161265 A1 | 7/2006 | Levine et al. |
| 2006/0167474 A1 | 7/2006 | Bloom et al. |
| 2006/0167543 A1 | 7/2006 | Bailey et al. |
| 2006/0173524 A1 | 8/2006 | Salahieh et al. |
| 2006/0178740 A1 | 8/2006 | Stacchino et al. |
| 2006/0190070 A1 | 8/2006 | Dieck et al. |
| 2006/0193885 A1 | 8/2006 | Leonard Neethling et al. |
| 2006/0195134 A1 | 8/2006 | Crittenden |
| 2006/0195183 A1 | 8/2006 | Navia et al. |
| 2006/0195186 A1 | 8/2006 | Drews et al. |
| 2006/0206192 A1 | 9/2006 | Tower et al. |
| 2006/0206202 A1 | 9/2006 | Bonhoeffer et al. |
| 2006/0210597 A1 | 9/2006 | Hiles |
| 2006/0212110 A1 | 9/2006 | Osborne et al. |
| 2006/0212111 A1 | 9/2006 | Case et al. |
| 2006/0217802 A1 | 9/2006 | Ruiz et al. |
| 2006/0224183 A1 | 10/2006 | Freudenthal |
| 2006/0229561 A1 | 10/2006 | Huszar |
| 2006/0229700 A1 | 10/2006 | Acosta et al. |
| 2006/0229718 A1 | 10/2006 | Marquez |
| 2006/0229719 A1 | 10/2006 | Marquez et al. |
| 2006/0241745 A1 | 10/2006 | Solem |
| 2006/0246584 A1 | 11/2006 | Covelli |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265043 A1 | 11/2006 | Mandrusov et al. |
| 2006/0265056 A1 | 11/2006 | Nguyen et al. |
| 2006/0270958 A1 | 11/2006 | George |
| 2006/0271149 A1 | 11/2006 | Berez et al. |
| 2006/0271161 A1 | 11/2006 | Meyer et al. |
| 2006/0271166 A1 | 11/2006 | Thill et al. |
| 2006/0271175 A1 | 11/2006 | Woolfson et al. |
| 2006/0276872 A1 | 12/2006 | Arbefeuille et al. |
| 2006/0276873 A1 | 12/2006 | Sato |
| 2006/0276874 A1 | 12/2006 | Wilson et al. |
| 2006/0276882 A1 | 12/2006 | Case et al. |
| 2006/0276887 A1 | 12/2006 | Brady et al. |
| 2006/0282161 A1 | 12/2006 | Huynh et al. |
| 2006/0287668 A1 | 12/2006 | Fawzi et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0010877 A1 | 1/2007 | Salahieh et al. |
| 2007/0010878 A1 | 1/2007 | Rafiee et al. |
| 2007/0010887 A1 | 1/2007 | Williams et al. |
| 2007/0016286 A1 | 1/2007 | Herrmann et al. |
| 2007/0016288 A1 | 1/2007 | Gurskis et al. |
| 2007/0020248 A1 | 1/2007 | Everaerts et al. |

(56) References Cited

U.S. PATENT DOCUMENTS

| | | |
|---|---|---|
| 2007/0021826 A1 | 1/2007 | Case et al. |
| 2007/0027518 A1 | 2/2007 | Case et al. |
| 2007/0027520 A1 | 2/2007 | Sherburne |
| 2007/0027533 A1 | 2/2007 | Douk |
| 2007/0027535 A1 | 2/2007 | Purdy, Jr. et al. |
| 2007/0032856 A1 | 2/2007 | Limon |
| 2007/0032879 A1 | 2/2007 | Levine et al. |
| 2007/0038291 A1 | 2/2007 | Case et al. |
| 2007/0038295 A1 | 2/2007 | Case et al. |
| 2007/0043420 A1 | 2/2007 | Lostetter |
| 2007/0043424 A1 | 2/2007 | Pryor |
| 2007/0043431 A1 | 2/2007 | Melsheimer |
| 2007/0043435 A1 | 2/2007 | Seguin et al. |
| 2007/0050014 A1 | 3/2007 | Johnson |
| 2007/0051377 A1 | 3/2007 | Douk et al. |
| 2007/0055340 A1 | 3/2007 | Pryor |
| 2007/0056346 A1 | 3/2007 | Spenser et al. |
| 2007/0060998 A1 | 3/2007 | Butterwick et al. |
| 2007/0061002 A1 | 3/2007 | Paul, Jr. et al. |
| 2007/0061008 A1 | 3/2007 | Salahieh et al. |
| 2007/0073389 A1 | 3/2007 | Bolduc et al. |
| 2007/0073392 A1 | 3/2007 | Heyninck-Jantz et al. |
| 2007/0078504 A1 | 4/2007 | Mialhe |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0100427 A1 | 5/2007 | Perouse |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112355 A1 | 5/2007 | Salahieh et al. |
| 2007/0112358 A1 | 5/2007 | Abbott et al. |
| 2007/0112415 A1 | 5/2007 | Bartlett |
| 2007/0112422 A1 | 5/2007 | Dehdashtian |
| 2007/0118214 A1 | 5/2007 | Salahieh et al. |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0142907 A1 | 6/2007 | Moaddeb et al. |
| 2007/0155010 A1 | 7/2007 | Farnsworth et al. |
| 2007/0156233 A1 | 7/2007 | Kapadia et al. |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162113 A1 | 7/2007 | Sharkawy et al. |
| 2007/0173918 A1 | 7/2007 | Dreher et al. |
| 2007/0173932 A1 | 7/2007 | Cali et al. |
| 2007/0179592 A1 | 8/2007 | Schaeffer |
| 2007/0179600 A1 | 8/2007 | Vardi |
| 2007/0185513 A1 | 8/2007 | Woolfson et al. |
| 2007/0185565 A1 | 8/2007 | Schwammenthal et al. |
| 2007/0185571 A1 | 8/2007 | Kapadia et al. |
| 2007/0198078 A1 | 8/2007 | Berra et al. |
| 2007/0198097 A1 | 8/2007 | Zegdi |
| 2007/0203391 A1 | 8/2007 | Bloom et al. |
| 2007/0203503 A1 | 8/2007 | Salahieh et al. |
| 2007/0203560 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0225681 A1 | 9/2007 | House |
| 2007/0225802 A1 | 9/2007 | Forsell |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244543 A1 | 10/2007 | Mitchell |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244551 A1 | 10/2007 | Stobie |
| 2007/0244552 A1 | 10/2007 | Salahieh et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250151 A1 | 10/2007 | Pereira |
| 2007/0250160 A1 | 10/2007 | Rafiee |
| 2007/0255386 A1 | 11/2007 | Tenne |
| 2007/0255390 A1 | 11/2007 | Ducke et al. |
| 2007/0255394 A1 | 11/2007 | Ryan |
| 2007/0255396 A1 | 11/2007 | Douk et al. |
| 2007/0260301 A1 | 11/2007 | Chuter et al. |
| 2007/0260327 A1 | 11/2007 | Case et al. |
| 2007/0265701 A1 | 11/2007 | Gurskis et al. |
| 2007/0270751 A1 | 11/2007 | Stangenes et al. |
| 2007/0270943 A1 | 11/2007 | Solem et al. |
| 2007/0273813 A1 | 11/2007 | Yoshida et al. |
| 2007/0282436 A1 | 12/2007 | Pinchuk |
| 2007/0287717 A1 | 12/2007 | Fanning et al. |
| 2007/0288000 A1 | 12/2007 | Bonan |
| 2007/0288087 A1 | 12/2007 | Fearnot et al. |
| 2007/0288089 A1 | 12/2007 | Gurskis et al. |
| 2008/0004688 A1 | 1/2008 | Spenser et al. |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0022504 A1 | 1/2008 | Melsheimer |
| 2008/0033534 A1 | 2/2008 | Cook et al. |
| 2008/0033541 A1 | 2/2008 | Gelbart et al. |
| 2008/0039925 A1 | 2/2008 | Ishimaru et al. |
| 2008/0039934 A1 | 2/2008 | Styrc |
| 2008/0045921 A1 | 2/2008 | Anderson et al. |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077234 A1 | 3/2008 | Styrc |
| 2008/0077236 A1 | 3/2008 | Letac et al. |
| 2008/0082165 A1 | 4/2008 | Wilson et al. |
| 2008/0082166 A1 | 4/2008 | Styrc et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0109070 A1 | 5/2008 | Wagner et al. |
| 2008/0125859 A1 | 5/2008 | Salahieh et al. |
| 2008/0127707 A1 | 6/2008 | Kokish et al. |
| 2008/0133002 A1 | 6/2008 | Gelbart et al. |
| 2008/0133003 A1 | 6/2008 | Seguin et al. |
| 2008/0140188 A1 | 6/2008 | Rahdert et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161909 A1 | 7/2008 | Kheradvar et al. |
| 2008/0161910 A1 | 7/2008 | Revuelta et al. |
| 2008/0161911 A1 | 7/2008 | Revuelta et al. |
| 2008/0172119 A1 | 7/2008 | Yamasaki et al. |

(56)                References Cited

U.S. PATENT DOCUMENTS

| | | |
|---|---|---|
| 2008/0177381 A1 | 7/2008 | Navia et al. |
| 2008/0183273 A1 | 7/2008 | Mesana et al. |
| 2008/0188928 A1 | 8/2008 | Salahieh et al. |
| 2008/0195193 A1 | 8/2008 | Purdy et al. |
| 2008/0195199 A1 | 8/2008 | Kheradvar et al. |
| 2008/0200977 A1 | 8/2008 | Paul et al. |
| 2008/0208209 A1 | 8/2008 | Fischer et al. |
| 2008/0208327 A1 | 8/2008 | Rowe |
| 2008/0208328 A1 | 8/2008 | Antocci et al. |
| 2008/0208332 A1 | 8/2008 | Lamphere et al. |
| 2008/0215143 A1 | 9/2008 | Seguin |
| 2008/0215144 A1 | 9/2008 | Ryan et al. |
| 2008/0221672 A1 | 9/2008 | Lamphere et al. |
| 2008/0221703 A1 | 9/2008 | Que et al. |
| 2008/0228254 A1 | 9/2008 | Ryan |
| 2008/0228263 A1 | 9/2008 | Ryan |
| 2008/0234443 A1 | 9/2008 | Kiss et al. |
| 2008/0234797 A1 | 9/2008 | Styrc |
| 2008/0234814 A1 | 9/2008 | Salahieh et al. |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262590 A1 | 10/2008 | Murray |
| 2008/0262592 A1 | 10/2008 | Jordan et al. |
| 2008/0262593 A1 | 10/2008 | Ryan et al. |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288054 A1 | 11/2008 | Pulnev et al. |
| 2009/0005863 A1 | 1/2009 | Goetz et al. |
| 2009/0012356 A1 | 1/2009 | Dann et al. |
| 2009/0012600 A1 | 1/2009 | Styrc et al. |
| 2009/0030512 A1 | 1/2009 | Thielen et al. |
| 2009/0048656 A1 | 2/2009 | Wen |
| 2009/0054968 A1 | 2/2009 | Bonhoeffer et al. |
| 2009/0054969 A1 | 2/2009 | Salahieh et al. |
| 2009/0054976 A1 | 2/2009 | Tuval et al. |
| 2009/0062908 A1 | 3/2009 | Bonhoeffer et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0076598 A1 | 3/2009 | Salahieh et al. |
| 2009/0082844 A1 | 3/2009 | Zacharias et al. |
| 2009/0082858 A1 | 3/2009 | Nugent et al. |
| 2009/0085900 A1 | 4/2009 | Weiner |
| 2009/0093876 A1 | 4/2009 | Nitzan et al. |
| 2009/0093877 A1 | 4/2009 | Keidar et al. |
| 2009/0099640 A1 | 4/2009 | Weng |
| 2009/0099641 A1 | 4/2009 | Wu et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0163951 A1 | 6/2009 | Simmons et al. |
| 2009/0164004 A1 | 6/2009 | Cohn |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192601 A1 | 7/2009 | Rafiee et al. |
| 2009/0198316 A1 | 8/2009 | Laske et al. |
| 2009/0198323 A1 | 8/2009 | Johnson et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0222082 A1 | 9/2009 | Lock et al. |
| 2009/0234407 A1 | 9/2009 | Hastings et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264759 A1 | 10/2009 | Byrd |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287290 A1 | 11/2009 | Macaulay et al. |
| 2009/0287296 A1 | 11/2009 | Manasse |
| 2009/0287299 A1 | 11/2009 | Tabor et al. |
| 2009/0299462 A1 | 12/2009 | Fawzi et al. |
| 2009/0319037 A1 | 12/2009 | Rowe et al. |
| 2010/0004739 A1 | 1/2010 | Vesely |
| 2010/0004740 A1 | 1/2010 | Seguin et al. |
| 2010/0011564 A1 | 1/2010 | Millwee et al. |
| 2010/0022948 A1 | 1/2010 | Wilson et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049313 A1 | 2/2010 | Alon et al. |
| 2010/0057051 A1 | 3/2010 | Howat et al. |
| 2010/0057185 A1 | 3/2010 | Melsheimer et al. |
| 2010/0063573 A1 | 3/2010 | Hijlkema et al. |
| 2010/0069852 A1 | 3/2010 | Kelley |
| 2010/0069916 A1 | 3/2010 | Cully et al. |
| 2010/0070027 A1 | 3/2010 | Bonhoeffer et al. |
| 2010/0082089 A1 | 4/2010 | Quadri et al. |
| 2010/0082094 A1 | 4/2010 | Quadri et al. |
| 2010/0087913 A1 | 4/2010 | Rabkin et al. |
| 2010/0094399 A1 | 4/2010 | Dorn et al. |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0131057 A1 | 5/2010 | Subramanian et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0160725 A1 | 6/2010 | Kiser et al. |
| 2010/0161045 A1 | 6/2010 | Righini |
| 2010/0168839 A1 | 7/2010 | Braido et al. |
| 2010/0174362 A1 | 7/2010 | Straubinger et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0198346 A1 | 8/2010 | Keogh et al. |
| 2010/0210991 A1 | 8/2010 | Wilk et al. |
| 2010/0219092 A1 | 9/2010 | Salahieh et al. |
| 2010/0234932 A1 | 9/2010 | Arbefeuille et al. |
| 2010/0234940 A1 | 9/2010 | Dolan |
| 2010/0239917 A1 | 9/2010 | Lee et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256723 A1 | 10/2010 | Murray |
| 2010/0262231 A1 | 10/2010 | Tuval et al. |
| 2010/0268332 A1 | 10/2010 | Tuval et al. |
| 2010/0280459 A1 | 11/2010 | Werner |
| 2010/0280495 A1 | 11/2010 | Paul et al. |
| 2010/0286768 A1 | 11/2010 | Alkhatib |
| 2010/0292779 A1 | 11/2010 | Straubinger et al. |
| 2010/0292780 A1 | 11/2010 | Straubinger et al. |
| 2010/0292785 A1 | 11/2010 | Seguin et al. |
| 2010/0298931 A1 | 11/2010 | Quadri et al. |
| 2011/0004297 A1 | 1/2011 | Sogard et al. |
| 2011/0015616 A1 | 1/2011 | Straubinger et al. |
| 2011/0022157 A1 | 1/2011 | Essinger et al. |
| 2011/0028290 A1 | 2/2011 | Ozawa |
| 2011/0029066 A1 | 2/2011 | Gilad et al. |
| 2011/0034852 A1 | 2/2011 | Hausler et al. |
| 2011/0040366 A1 | 2/2011 | Goetz et al. |

(56) References Cited

U.S. PATENT DOCUMENTS

| | | |
|---|---|---|
| 2011/0040374 A1 | 2/2011 | Goetz et al. |
| 2011/0071613 A1 | 3/2011 | Wood et al. |
| 2011/0093007 A1 | 4/2011 | Abbott et al. |
| 2011/0098805 A1 | 4/2011 | Dwork et al. |
| 2011/0106244 A1 | 5/2011 | Ferrari et al. |
| 2011/0118545 A1 | 5/2011 | Williams et al. |
| 2011/0137397 A1 | 6/2011 | Chau et al. |
| 2011/0166637 A1 | 7/2011 | Irwin et al. |
| 2011/0190862 A1 | 8/2011 | Bashiri et al. |
| 2011/0190874 A1 | 8/2011 | Celermajer et al. |
| 2011/0208290 A1 | 8/2011 | Straubinger et al. |
| 2011/0208297 A1 | 8/2011 | Tuval et al. |
| 2011/0224780 A1 | 9/2011 | Tabor et al. |
| 2011/0238159 A1 | 9/2011 | Guyenot et al. |
| 2011/0238167 A1 | 9/2011 | Dove et al. |
| 2011/0257729 A1 | 10/2011 | Spenser et al. |
| 2011/0257733 A1 | 10/2011 | Dwork |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276091 A1 | 11/2011 | Melanson et al. |
| 2011/0276121 A1 | 11/2011 | Levine |
| 2011/0276129 A1 | 11/2011 | Salahieh et al. |
| 2011/0288626 A1 | 11/2011 | Straubinger et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0035719 A1 | 2/2012 | Forster et al. |
| 2012/0035720 A1 | 2/2012 | Cali et al. |
| 2012/0041547 A1 | 2/2012 | Duffy et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0065464 A1 | 3/2012 | Ellis et al. |
| 2012/0078347 A1 | 3/2012 | Braido et al. |
| 2012/0078357 A1 | 3/2012 | Conklin |
| 2012/0078360 A1 | 3/2012 | Rafiee |
| 2012/0089224 A1 | 4/2012 | Haug et al. |
| 2012/0100182 A1 | 4/2012 | Mooney et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |
| 2012/0123515 A1 | 5/2012 | Hosford et al. |
| 2012/0123529 A1 | 5/2012 | Levi et al. |
| 2012/0130468 A1 | 5/2012 | Khosravi et al. |
| 2012/0132547 A1 | 5/2012 | Salahieh et al. |
| 2012/0136430 A1 | 5/2012 | Sochman et al. |
| 2012/0143084 A1 | 6/2012 | Shoham |
| 2012/0165957 A1 | 6/2012 | Everland et al. |
| 2012/0172982 A1 | 7/2012 | Stacchino et al. |
| 2012/0179244 A1 | 7/2012 | Schankereli et al. |
| 2012/0185030 A1 | 7/2012 | Igaki et al. |
| 2012/0197379 A1 | 8/2012 | Laske et al. |
| 2012/0197391 A1 | 8/2012 | Alkhatib et al. |
| 2012/0209374 A1 | 8/2012 | Bonhoeffer et al. |
| 2012/0209376 A1 | 8/2012 | Hauser et al. |
| 2012/0221100 A1 | 8/2012 | Huber |
| 2012/0226341 A1 | 9/2012 | Schreck et al. |
| 2012/0265296 A1 | 10/2012 | McNamara et al. |
| 2012/0283715 A1 | 11/2012 | Mihalik et al. |
| 2012/0283823 A1 | 11/2012 | Bonhoeffer et al. |
| 2012/0303113 A1 | 11/2012 | Benichou et al. |
| 2012/0303116 A1 | 11/2012 | Gorman, III et al. |
| 2012/0305441 A1 | 12/2012 | Murray et al. |
| 2012/0310332 A1 | 12/2012 | Murray et al. |
| 2012/0316637 A1 | 12/2012 | Holm et al. |
| 2012/0330408 A1 | 12/2012 | Hillukka et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0023984 A1 | 1/2013 | Conklin |
| 2013/0030519 A1 | 1/2013 | Tran et al. |
| 2013/0030520 A1 | 1/2013 | Lee et al. |
| 2013/0046373 A1 | 2/2013 | Cartledge et al. |
| 2013/0053949 A1 | 2/2013 | Pintor et al. |
| 2013/0066342 A1 | 3/2013 | Dell et al. |
| 2013/0066419 A1 | 3/2013 | Gregg |
| 2013/0071441 A1 | 3/2013 | Iwazawa et al. |
| 2013/0073037 A1 | 3/2013 | Gregg et al. |
| 2013/0079867 A1 | 3/2013 | Hoffman et al. |
| 2013/0079869 A1 | 3/2013 | Straubinger et al. |
| 2013/0089655 A1 | 4/2013 | Gregg |
| 2013/0090728 A1 | 4/2013 | Solem |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0138207 A1 | 5/2013 | Quadri et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0166017 A1 | 6/2013 | Cartledge et al. |
| 2013/0178930 A1 | 7/2013 | Straubinger et al. |
| 2013/0184813 A1 | 7/2013 | Quadri et al. |
| 2013/0190865 A1 | 7/2013 | Anderson |
| 2013/0204359 A1 | 8/2013 | Thubrikar et al. |
| 2013/0231735 A1 | 9/2013 | Deem et al. |
| 2013/0245752 A1 | 9/2013 | Goetz et al. |
| 2013/0253342 A1 | 9/2013 | Griswold et al. |
| 2013/0253635 A1 | 9/2013 | Straubinger et al. |
| 2013/0253640 A1 | 9/2013 | Meiri et al. |
| 2013/0268067 A1 | 10/2013 | Forster et al. |
| 2013/0274865 A1 | 10/2013 | Haverkost et al. |
| 2013/0274870 A1 | 10/2013 | Lombardi et al. |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2013/0310928 A1 | 11/2013 | Morriss et al. |
| 2013/0325101 A1 | 12/2013 | Goetz et al. |
| 2013/0338595 A1 | 12/2013 | Voss |
| 2013/0338755 A1 | 12/2013 | Goetz et al. |
| 2013/0345799 A1 | 12/2013 | Lafontaine |
| 2014/0012368 A1 | 1/2014 | Sugimoto et al. |
| 2014/0012370 A1 | 1/2014 | Bonhoeffer et al. |
| 2014/0018911 A1 | 1/2014 | Zhou et al. |
| 2014/0052239 A1 | 2/2014 | Kong et al. |
| 2014/0058501 A1 | 2/2014 | Bonhoeffer et al. |
| 2014/0083190 A1 | 3/2014 | Kaack et al. |
| 2014/0088680 A1 | 3/2014 | Costello et al. |
| 2014/0094904 A1 | 4/2014 | Salahieh et al. |
| 2014/0114390 A1 | 4/2014 | Tobis et al. |
| 2014/0114405 A1 | 4/2014 | Paul et al. |
| 2014/0114406 A1 | 4/2014 | Salahieh et al. |
| 2014/0114407 A1 | 4/2014 | Rajamannan |
| 2014/0121763 A1 | 5/2014 | Duffy et al. |
| 2014/0121766 A1 | 5/2014 | Salahieh et al. |
| 2014/0128969 A1 | 5/2014 | Hill et al. |
| 2014/0135909 A1 | 5/2014 | Carr et al. |
| 2014/0135912 A1 | 5/2014 | Salahieh et al. |
| 2014/0207229 A1 | 7/2014 | Shoemaker et al. |
| 2014/0222039 A1 | 8/2014 | Khosrovaninejad |
| 2014/0222142 A1 | 8/2014 | Kovalsky et al. |
| 2014/0236287 A1 | 8/2014 | Clague et al. |
| 2014/0243962 A1 | 8/2014 | Wilson et al. |
| 2014/0243963 A1 | 8/2014 | Sheps et al. |
| 2014/0243967 A1 | 8/2014 | Salahieh et al. |
| 2014/0249621 A1 | 9/2014 | Eidenschink |
| 2014/0249622 A1 | 9/2014 | Carmi et al. |

(56) References Cited

U.S. PATENT DOCUMENTS

| | | |
|---|---|---|
| 2014/0257473 A1 | 9/2014 | Rajamannan |
| 2014/0277414 A1 | 9/2014 | Kheradvar |
| 2014/0296962 A1 | 10/2014 | Cartledge et al. |
| 2014/0309732 A1 | 10/2014 | Solem |
| 2014/0316518 A1 | 10/2014 | Kheradvar et al. |
| 2014/0330371 A1 | 11/2014 | Gloss et al. |
| 2014/0343669 A1 | 11/2014 | Lane et al. |
| 2014/0364799 A1 | 12/2014 | Beauvais et al. |
| 2014/0379068 A1 | 12/2014 | Thielen et al. |
| 2015/0012085 A1 | 1/2015 | Salahieh et al. |
| 2015/0032056 A1 | 1/2015 | Okamura et al. |
| 2015/0032198 A1 | 1/2015 | Folk |
| 2015/0073540 A1 | 3/2015 | Salahieh et al. |
| 2015/0073541 A1 | 3/2015 | Salahieh et al. |
| 2015/0088252 A1 | 3/2015 | Jenson et al. |
| 2015/0094804 A1 | 4/2015 | Bonhoeffer et al. |
| 2015/0105857 A1 | 4/2015 | Bonhoeffer et al. |
| 2015/0127092 A1 | 5/2015 | Straubinger et al. |
| 2015/0127094 A1 | 5/2015 | Salahieh et al. |
| 2015/0142102 A1 | 5/2015 | Lafontaine et al. |
| 2015/0148894 A1 | 5/2015 | Damm et al. |
| 2015/0209142 A1 | 7/2015 | Paul et al. |
| 2015/0209146 A1 | 7/2015 | Hill et al. |
| 2015/0223933 A1 | 8/2015 | Haug et al. |
| 2015/0238315 A1 | 8/2015 | Rabito et al. |
| 2015/0245909 A1 | 9/2015 | Salahieh et al. |
| 2015/0272731 A1 | 10/2015 | Racchini et al. |
| 2015/0320557 A1 | 11/2015 | Sutton et al. |
| 2015/0335423 A1 | 11/2015 | Gregg et al. |
| 2015/0352252 A1 | 12/2015 | Nakamura et al. |
| 2015/0359997 A1 | 12/2015 | Crisostomo et al. |
| 2016/0022418 A1 | 1/2016 | Salahieh et al. |
| 2016/0045306 A1 | 2/2016 | Agrawal et al. |
| 2016/0045307 A1 | 2/2016 | Yohanan et al. |
| 2016/0051362 A1 | 2/2016 | Cooper et al. |
| 2016/0067040 A1 | 3/2016 | Agrawal et al. |
| 2016/0120645 A1 | 5/2016 | Alon |
| 2016/0135951 A1 | 5/2016 | Salahieh et al. |
| 2016/0143731 A1 | 5/2016 | Backus et al. |
| 2016/0158003 A1 | 6/2016 | Wallace et al. |
| 2016/0166384 A1 | 6/2016 | Olson et al. |
| 2016/0199184 A1 | 7/2016 | Ma et al. |
| 2016/0206423 A1 | 7/2016 | O'Connor et al. |
| 2016/0213467 A1 | 7/2016 | Backus et al. |
| 2016/0220256 A1 | 8/2016 | Khosrovaninejad |
| 2016/0220359 A1 | 8/2016 | Backus et al. |
| 2016/0220360 A1 | 8/2016 | Lin et al. |
| 2016/0220365 A1 | 8/2016 | Backus et al. |
| 2016/0250024 A1 | 9/2016 | Hill et al. |
| 2016/0256271 A1 | 9/2016 | Backus et al. |
| 2016/0262878 A1 | 9/2016 | Backus et al. |
| 2016/0346107 A1 | 12/2016 | Matthison-Hansen et al. |
| 2016/0354203 A1 | 12/2016 | Tuval et al. |
| 2016/0374793 A1 | 12/2016 | Lafontaine et al. |
| 2016/0376063 A1 | 12/2016 | Salahieh et al. |
| 2017/0000609 A1 | 1/2017 | Gross et al. |
| 2017/0007400 A1 | 1/2017 | Sogard et al. |
| 2017/0027654 A1 | 2/2017 | Frimer et al. |
| 2017/0027693 A1 | 2/2017 | Paul et al. |
| 2017/0049563 A1 | 2/2017 | Straubinger et al. |
| 2017/0049568 A1 | 2/2017 | Straubinger et al. |
| 2017/0056172 A1 | 3/2017 | Salahieh et al. |
| 2017/0065410 A1 | 3/2017 | Straubinger et al. |
| 2017/0087343 A1 | 3/2017 | Assaf et al. |
| 2017/0095595 A1 | 4/2017 | Nakamura |
| 2017/0189177 A1 | 7/2017 | Schweich, Jr. et al. |
| 2017/0212723 A1 | 7/2017 | Atarot et al. |
| 2017/0265849 A1 | 9/2017 | Assaf et al. |
| 2017/0325954 A1 | 11/2017 | Perszyk |
| 2017/0333230 A1 | 11/2017 | Folan et al. |
| 2017/0348013 A1 | 12/2017 | Mottola et al. |
| 2018/0116843 A1 | 5/2018 | Schreck et al. |
| 2018/0325604 A1 | 11/2018 | Atarot et al. |
| 2018/0368976 A1 | 12/2018 | Bonhoeffer et al. |
| 2019/0328522 A1 | 10/2019 | Straubinger et al. |
| 2020/0054449 A1 | 2/2020 | Min et al. |
| 2020/0383717 A1 | 12/2020 | Lederman et al. |
| 2021/0038313 A1 | 2/2021 | Sholev et al. |
| 2021/0322153 A1 | 10/2021 | Tuval et al. |
| 2022/0061987 A1 | 3/2022 | Duffy |
| 2022/0079747 A1 | 3/2022 | Girard et al. |
| 2022/0192765 A1 | 6/2022 | Brasset et al. |
| 2022/0304803 A1 | 9/2022 | Guyenot et al. |
| 2024/0008978 A1 | 1/2024 | Nawalakhe et al. |
| 2024/0148503 A1 | 5/2024 | Chu et al. |
| 2024/0164902 A1 | 5/2024 | Lee et al. |
| 2024/0164903 A1 | 5/2024 | Chu et al. |

FOREIGN PATENT DOCUMENTS

| | | |
|---|---|---|
| AU | 777443 B2 | 10/2004 |
| AU | 778831 B2 | 12/2004 |
| AU | 2004231189 A1 | 12/2004 |
| AU | 2004242527 A1 | 1/2005 |
| AU | 2001281277 B2 | 9/2005 |
| AU | 2006308187 A1 | 5/2007 |
| AU | 2006310681 A1 | 5/2007 |
| AU | 2006328896 A1 | 6/2007 |
| AU | 2002329324 B2 | 7/2007 |
| AU | 2007294199 A1 | 3/2008 |
| AU | 2009200985 A1 | 4/2009 |
| AU | 2006328896 B2 | 8/2013 |
| CA | 2378589 A1 | 2/2001 |
| CA | 2381192 A1 | 2/2001 |
| CA | 2385662 A1 | 3/2001 |
| CA | 2407987 A1 | 11/2001 |
| CA | 2418958 A1 | 2/2002 |
| CA | 2435962 A1 | 8/2002 |
| CA | 2457755 A1 | 2/2003 |
| CA | 2436258 A1 | 1/2005 |
| CA | 2848485 A1 | 1/2005 |
| CA | 2848490 A1 | 1/2005 |
| CA | 2595233 A1 | 7/2006 |
| CA | 2627409 A1 | 5/2007 |
| CA | 2627555 A1 | 5/2007 |
| CA | 2634358 A1 | 6/2007 |
| CA | 2657839 A1 | 3/2008 |
| CA | 2659690 A1 | 3/2008 |
| CN | 1338951 A | 3/2002 |
| CN | 1342443 A | 4/2002 |
| CN | 1745727 A | 3/2006 |
| CN | 2762776 Y | 3/2006 |
| CN | 1897892 A | 1/2007 |
| CN | 2933337 Y | 8/2007 |
| CN | 101011298 A | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| CN | 102413793 A | 4/2012 |
| CN | 103118630 A | 5/2013 |
| DE | 2815756 A1 | 10/1979 |
| DE | 3640745 A1 | 6/1987 |
| DE | 3920657 A1 | 1/1991 |
| DE | 3640745 C2 | 3/1992 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 5/2000 |
| DE | 19857887 A1 | 7/2000 |
| DE | 19907646 A1 | 8/2000 |
| DE | 10010073 A1 | 9/2001 |
| DE | 10010074 A1 | 10/2001 |
| DE | 10034105 C1 | 4/2002 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10048814 A1 | 5/2002 |
| DE | 10121210 A1 | 11/2002 |
| DE | 19546692 C2 | 11/2002 |

(56) References Cited

FOREIGN PATENT DOCUMENTS

| | | | |
|---|---|---|---|
| DE | 10301026 | A1 | 2/2004 |
| DE | 10048814 | B4 | 4/2004 |
| DE | 10049812 | B4 | 6/2004 |
| DE | 10302447 | A1 | 7/2004 |
| DE | 10335948 | B3 | 2/2005 |
| DE | 10010074 | B4 | 4/2005 |
| DE | 19857887 | B4 | 5/2005 |
| DE | 10049815 | B4 | 10/2005 |
| DE | 10010073 | B4 | 12/2005 |
| DE | 102005003632 | A1 | 8/2006 |
| DE | 102005051849 | A1 | 5/2007 |
| DE | 102005052628 | A1 | 5/2007 |
| DE | 202007005491 | U1 | 6/2007 |
| DE | 20221871 | U1 | 9/2008 |
| DE | 69937568 | T2 | 9/2008 |
| DK | 1112042 | T3 | 2/2008 |
| DK | 200800058 | U1 | 6/2008 |
| DK | 200800058 | U3 | 7/2008 |
| DK | 1259195 | T3 | 2/2009 |
| DK | 1281375 | T3 | 5/2012 |
| EP | 0084395 | A1 | 7/1983 |
| EP | 0103546 | A1 | 3/1984 |
| EP | 0254701 | A1 | 1/1988 |
| EP | 0103546 | B1 | 5/1988 |
| EP | 0144167 | B1 | 11/1989 |
| EP | 0402036 | A1 | 12/1990 |
| EP | 0402176 | A2 | 12/1990 |
| EP | 0411118 | A1 | 2/1991 |
| EP | 0458877 | A1 | 12/1991 |
| EP | 0515324 | A1 | 11/1992 |
| EP | 0547135 | A1 | 6/1993 |
| EP | 0579523 | A1 | 1/1994 |
| EP | 0402176 | B1 | 4/1994 |
| EP | 0592410 | A1 | 4/1994 |
| EP | 0597967 | A1 | 5/1994 |
| EP | 0597967 | A4 | 12/1994 |
| EP | 0458877 | B1 | 5/1995 |
| EP | 0657147 | A2 | 6/1995 |
| EP | 0592410 | B1 | 10/1995 |
| EP | 0696447 | A2 | 2/1996 |
| EP | 0402036 | B1 | 4/1996 |
| EP | 0729364 | A1 | 9/1996 |
| EP | 0732088 | A2 | 9/1996 |
| EP | 0756498 | A1 | 2/1997 |
| EP | 0409929 | B1 | 4/1997 |
| EP | 0778775 | A1 | 6/1997 |
| EP | 0786970 | A1 | 8/1997 |
| EP | 0792624 | A1 | 9/1997 |
| EP | 0797957 | A1 | 10/1997 |
| EP | 0797958 | A1 | 10/1997 |
| EP | 0799604 | A1 | 10/1997 |
| EP | 0801928 | A1 | 10/1997 |
| EP | 0815798 | A2 | 1/1998 |
| EP | 0826346 | A1 | 3/1998 |
| EP | 0829239 | A1 | 3/1998 |
| EP | 0836834 | A2 | 4/1998 |
| EP | 0850607 | A1 | 7/1998 |
| EP | 0853921 | A2 | 7/1998 |
| EP | 0858779 | A1 | 8/1998 |
| EP | 0871414 | A1 | 10/1998 |
| EP | 0876796 | A2 | 11/1998 |
| EP | 0876803 | A2 | 11/1998 |
| EP | 0778775 | B1 | 1/1999 |
| EP | 0888142 | A1 | 1/1999 |
| EP | 0888750 | A1 | 1/1999 |
| EP | 0895752 | A1 | 2/1999 |
| EP | 0896813 | A2 | 2/1999 |
| EP | 0903122 | A2 | 3/1999 |
| EP | 0876796 | A3 | 5/1999 |
| EP | 0928615 | A1 | 7/1999 |
| EP | 0657147 | B1 | 8/1999 |
| EP | 0934728 | A2 | 8/1999 |
| EP | 0938877 | A2 | 9/1999 |
| EP | 0943302 | A2 | 9/1999 |
| EP | 0597967 | B1 | 12/1999 |
| EP | 0696447 | B1 | 1/2000 |
| EP | 0971649 | A1 | 1/2000 |
| EP | 0986348 | A1 | 3/2000 |
| EP | 1000590 | A1 | 5/2000 |
| EP | 1011523 | A1 | 6/2000 |
| EP | 1020166 | A1 | 7/2000 |
| EP | 1027870 | A1 | 8/2000 |
| EP | 1041942 | A1 | 10/2000 |
| EP | 1041943 | A1 | 10/2000 |
| EP | 1051204 | A2 | 11/2000 |
| EP | 1057459 | A1 | 12/2000 |
| EP | 1057460 | A1 | 12/2000 |
| EP | 1078610 | A2 | 2/2001 |
| EP | 1088529 | A2 | 4/2001 |
| EP | 1089676 | A2 | 4/2001 |
| EP | 1093771 | A2 | 4/2001 |
| EP | 1097676 | A1 | 5/2001 |
| EP | 1112042 | A1 | 7/2001 |
| EP | 1112097 | A1 | 7/2001 |
| EP | 1117446 | A1 | 7/2001 |
| EP | 1158937 | A1 | 12/2001 |
| EP | 0547135 | B1 | 1/2002 |
| EP | 0729364 | B1 | 1/2002 |
| EP | 1164976 | A1 | 1/2002 |
| EP | 1166721 | A2 | 1/2002 |
| EP | 1171061 | A1 | 1/2002 |
| EP | 1206179 | A1 | 5/2002 |
| EP | 0756498 | B1 | 7/2002 |
| EP | 1233731 | A1 | 8/2002 |
| EP | 0986348 | B1 | 9/2002 |
| EP | 1235537 | A1 | 9/2002 |
| EP | 1248655 | A1 | 10/2002 |
| EP | 1251804 | A1 | 10/2002 |
| EP | 1251805 | A2 | 10/2002 |
| EP | 1255510 | A1 | 11/2002 |
| EP | 1257305 | A1 | 11/2002 |
| EP | 1259193 | A1 | 11/2002 |
| EP | 1259195 | A1 | 11/2002 |
| EP | 0959815 | B1 | 12/2002 |
| EP | 0971649 | B1 | 12/2002 |
| EP | 1262201 | A1 | 12/2002 |
| EP | 1264582 | A2 | 12/2002 |
| EP | 1281357 | A2 | 2/2003 |
| EP | 1281375 | A2 | 2/2003 |
| EP | 0888142 | B1 | 5/2003 |
| EP | 1112097 | B1 | 6/2003 |
| EP | 1330213 | A1 | 7/2003 |
| EP | 0937439 | B1 | 9/2003 |
| EP | 1017868 | B1 | 9/2003 |
| EP | 1340473 | A2 | 9/2003 |
| EP | 1347785 | A1 | 10/2003 |
| EP | 1354569 | A1 | 10/2003 |
| EP | 1356793 | A2 | 10/2003 |
| EP | 1281375 | A3 | 12/2003 |
| EP | 1340473 | A3 | 2/2004 |
| EP | 1041943 | B1 | 3/2004 |
| EP | 1356793 | A3 | 3/2004 |
| EP | 1395208 | A1 | 3/2004 |
| EP | 1401359 | A2 | 3/2004 |
| EP | 0871414 | B1 | 4/2004 |
| EP | 1406561 | A2 | 4/2004 |
| EP | 1408882 | A1 | 4/2004 |
| EP | 1042045 | B1 | 5/2004 |
| EP | 1414295 | A2 | 5/2004 |
| EP | 0819013 | B1 | 6/2004 |
| EP | 1430853 | A2 | 6/2004 |
| EP | 1347785 | B1 | 7/2004 |
| EP | 1435878 | A1 | 7/2004 |
| EP | 1435879 | A1 | 7/2004 |
| EP | 1439800 | A2 | 7/2004 |
| EP | 1441672 | A1 | 8/2004 |
| EP | 0954248 | B1 | 9/2004 |
| EP | 1452153 | A1 | 9/2004 |
| EP | 0987998 | B1 | 10/2004 |
| EP | 1206179 | B1 | 10/2004 |
| EP | 1469797 | A1 | 10/2004 |
| EP | 1087727 | B1 | 11/2004 |
| EP | 1115452 | B1 | 11/2004 |
| EP | 1117446 | B1 | 11/2004 |

(56)  References Cited

FOREIGN PATENT DOCUMENTS

| | | | |
|---|---|---|---|
| EP | 1472996 | A1 | 11/2004 |
| EP | 1477202 | A2 | 11/2004 |
| EP | 1107710 | B1 | 12/2004 |
| EP | 1233731 | B1 | 12/2004 |
| EP | 1484081 | A1 | 12/2004 |
| EP | 1494616 | A2 | 1/2005 |
| EP | 1499366 | A1 | 1/2005 |
| EP | 1143879 | B1 | 3/2005 |
| EP | 1516599 | A2 | 3/2005 |
| EP | 1518518 | A2 | 3/2005 |
| EP | 1229864 | B1 | 4/2005 |
| EP | 1253875 | B1 | 4/2005 |
| EP | 1519697 | A1 | 4/2005 |
| EP | 1521414 | A1 | 4/2005 |
| EP | 1522278 | A2 | 4/2005 |
| EP | 1088529 | B1 | 6/2005 |
| EP | 1093771 | B1 | 6/2005 |
| EP | 1251803 | B1 | 6/2005 |
| EP | 1430853 | A3 | 6/2005 |
| EP | 1539047 | A2 | 6/2005 |
| EP | 1547533 | A2 | 6/2005 |
| EP | 1059894 | B1 | 7/2005 |
| EP | 1551274 | A2 | 7/2005 |
| EP | 1551336 | A1 | 7/2005 |
| EP | 1000590 | B1 | 8/2005 |
| EP | 1027013 | B1 | 8/2005 |
| EP | 1078610 | B1 | 8/2005 |
| EP | 1560542 | A1 | 8/2005 |
| EP | 1562515 | A1 | 8/2005 |
| EP | 1570809 | A1 | 9/2005 |
| EP | 1576937 | A2 | 9/2005 |
| EP | 0943302 | B1 | 10/2005 |
| EP | 1267753 | B1 | 10/2005 |
| EP | 1582178 | A2 | 10/2005 |
| EP | 1582179 | A2 | 10/2005 |
| EP | 1011523 | B1 | 11/2005 |
| EP | 1067869 | B1 | 11/2005 |
| EP | 1469797 | B1 | 11/2005 |
| EP | 1589902 | A1 | 11/2005 |
| EP | 1598031 | A2 | 11/2005 |
| EP | 1600110 | A1 | 11/2005 |
| EP | 1600121 | A1 | 11/2005 |
| EP | 0786970 | B1 | 12/2005 |
| EP | 1156757 | B1 | 12/2005 |
| EP | 1603493 | A2 | 12/2005 |
| EP | 1605871 | A1 | 12/2005 |
| EP | 1021141 | B1 | 1/2006 |
| EP | 1614400 | A2 | 1/2006 |
| EP | 1616531 | A2 | 1/2006 |
| EP | 1616536 | A2 | 1/2006 |
| EP | 1041942 | B1 | 6/2006 |
| EP | 1441672 | A4 | 6/2006 |
| EP | 1663070 | A2 | 6/2006 |
| EP | 1667614 | A1 | 6/2006 |
| EP | 1494616 | A4 | 7/2006 |
| EP | 1690515 | A1 | 8/2006 |
| EP | 1702247 | A2 | 9/2006 |
| EP | 1051204 | B1 | 12/2006 |
| EP | 1734902 | A1 | 12/2006 |
| EP | 1395208 | B1 | 1/2007 |
| EP | 1251805 | B1 | 3/2007 |
| EP | 1255510 | B1 | 4/2007 |
| EP | 1499366 | B1 | 7/2007 |
| EP | 1600121 | B1 | 7/2007 |
| EP | 1835948 | A1 | 9/2007 |
| EP | 1112042 | B1 | 11/2007 |
| EP | 1251797 | B1 | 11/2007 |
| EP | 1616531 | B1 | 12/2007 |
| EP | 1863545 | A2 | 12/2007 |
| EP | 1878407 | A1 | 1/2008 |
| EP | 1886649 | A2 | 2/2008 |
| EP | 1406561 | A4 | 3/2008 |
| EP | 1893132 | A2 | 3/2008 |
| EP | 1900343 | A2 | 3/2008 |
| EP | 1901681 | A1 | 3/2008 |
| EP | 1435878 | B1 | 4/2008 |
| EP | 1886649 | A3 | 4/2008 |
| EP | 1251804 | B1 | 7/2008 |
| EP | 1605871 | B1 | 7/2008 |
| EP | 1968491 | A2 | 9/2008 |
| EP | 1259195 | B1 | 10/2008 |
| EP | 1980220 | A1 | 10/2008 |
| EP | 1994913 | A2 | 11/2008 |
| EP | 1994913 | A3 | 12/2008 |
| EP | 2000115 | A2 | 12/2008 |
| EP | 1560542 | A4 | 1/2009 |
| EP | 1408882 | B1 | 2/2009 |
| EP | 1255510 | B3 | 3/2009 |
| EP | 1330213 | B1 | 3/2009 |
| EP | 2033593 | A1 | 3/2009 |
| EP | 2047824 | A1 | 4/2009 |
| EP | 2059192 | A1 | 5/2009 |
| EP | 2074964 | A1 | 7/2009 |
| EP | 1401359 | B1 | 8/2009 |
| EP | 1968491 | B1 | 7/2010 |
| EP | 1259193 | B1 | 11/2010 |
| EP | 2257242 | A1 | 12/2010 |
| EP | 2266503 | A2 | 12/2010 |
| EP | 2266504 | A2 | 12/2010 |
| EP | 1893132 | B1 | 3/2011 |
| EP | 2266503 | A3 | 4/2011 |
| EP | 2266504 | A3 | 4/2011 |
| EP | 2059192 | B1 | 7/2011 |
| EP | 1441672 | B1 | 9/2011 |
| EP | 2364669 | A2 | 9/2011 |
| EP | 2366363 | A1 | 9/2011 |
| EP | 2387977 | A1 | 11/2011 |
| EP | 1603493 | B1 | 12/2011 |
| EP | 1281375 | B1 | 2/2012 |
| EP | 2364669 | A3 | 3/2012 |
| EP | 2047824 | B1 | 5/2012 |
| EP | 2474287 | A1 | 7/2012 |
| EP | 2340075 | B1 | 3/2013 |
| EP | 2387977 | B1 | 11/2013 |
| EP | 1551274 | B1 | 12/2014 |
| EP | 2874812 | A1 | 5/2015 |
| EP | 2749254 | B1 | 6/2015 |
| EP | 1702247 | B1 | 8/2015 |
| EP | 2926766 | A1 | 10/2015 |
| EP | 1519697 | B1 | 11/2015 |
| EP | 1863545 | B1 | 11/2015 |
| EP | 1835948 | B1 | 2/2016 |
| EP | 1734902 | B1 | 6/2016 |
| EP | 3028668 | A1 | 6/2016 |
| EP | 1539047 | B1 | 11/2016 |
| EP | 1667614 | B1 | 12/2016 |
| EP | 3181096 | A1 | 6/2017 |
| EP | 2659861 | B1 | 3/2019 |
| EP | 1667614 | B2 | 4/2020 |
| EP | 3270825 | B1 | 4/2020 |
| EP | 3730094 | A1 | 10/2020 |
| EP | 3730094 | A1 | 4/2024 |
| EP | 4175594 | B1 | 5/2024 |
| ES | 2293734 | T3 | 3/2008 |
| ES | 2313954 | T3 | 3/2009 |
| ES | 2353733 | T3 | 3/2011 |
| ES | 2381337 | T3 | 5/2012 |
| ES | 2421438 | T3 | 9/2013 |
| FI | 8311 | U1 | 5/2009 |
| FR | 2432305 | A1 | 2/1980 |
| FR | 2788217 | A1 | 7/2000 |
| FR | 2815844 | A1 | 5/2002 |
| FR | 2826863 | A1 | 1/2003 |
| FR | 2828263 | A1 | 2/2003 |
| FR | 2874812 | A1 | 3/2006 |
| FR | 2828263 | B1 | 5/2007 |
| GB | 2018950 | A | 10/1979 |
| GB | 2056023 | A | 3/1981 |
| GB | 2316322 | A | 2/1998 |
| GB | 2316322 | B | 10/1998 |
| GB | 2398214 | A | 8/2004 |
| GB | 2398245 | A | 8/2004 |
| GB | 2398245 | B | 3/2007 |
| GB | 2433700 | A | 7/2007 |

(56)  References Cited

FOREIGN PATENT DOCUMENTS

| | | |
|---|---|---|
| GB | 2433700 B | 12/2007 |
| GB | 2440809 A | 2/2008 |
| GB | 2440809 B | 8/2011 |
| HK | 1053600 A1 | 7/2012 |
| JP | S5286296 A | 7/1977 |
| JP | S54137896 A | 9/1979 |
| JP | S62227352 A | 10/1987 |
| JP | S6449571 A | 2/1989 |
| JP | H0447576 B2 | 8/1992 |
| JP | H04505866 A | 10/1992 |
| JP | H06505187 A | 6/1994 |
| JP | H06343703 A | 12/1994 |
| JP | H07504091 A | 5/1995 |
| JP | H07505803 A | 6/1995 |
| JP | H07265339 A | 10/1995 |
| JP | H0833715 A | 2/1996 |
| JP | H1049571 A | 2/1998 |
| JP | H10507673 A | 7/1998 |
| JP | H11503056 A | 3/1999 |
| JP | 2001000460 A | 1/2001 |
| JP | 2001504016 A | 3/2001 |
| JP | 2001526574 A | 12/2001 |
| JP | 2002525168 A | 8/2002 |
| JP | 2002525169 A | 8/2002 |
| JP | 2002536115 A | 10/2002 |
| JP | 2003515386 A | 5/2003 |
| JP | 2003518984 A | 6/2003 |
| JP | 2003523262 A | 8/2003 |
| JP | 2003524504 A | 8/2003 |
| JP | 2004504111 A | 2/2004 |
| JP | 2004130068 A | 4/2004 |
| JP | 2004514467 A | 5/2004 |
| JP | 2004255186 A | 9/2004 |
| JP | 2004267750 A | 9/2004 |
| JP | 2004283461 A | 10/2004 |
| JP | 2005505343 A | 2/2005 |
| JP | 2005103321 A | 4/2005 |
| JP | 2005118585 A | 5/2005 |
| JP | 2007521125 A | 8/2007 |
| JP | 2007296375 A | 11/2007 |
| JP | 2007298375 A | 11/2007 |
| JP | 2007534381 A | 11/2007 |
| JP | 2007536003 A | 12/2007 |
| JP | 2008506497 A | 3/2008 |
| JP | 2008514345 A | 5/2008 |
| JP | 2008535572 A | 9/2008 |
| JP | 2008539985 A | 11/2008 |
| JP | 2008541865 A | 11/2008 |
| JP | 2009034529 A | 2/2009 |
| JP | 2009061293 A | 3/2009 |
| JP | 2009509635 A | 3/2009 |
| JP | 4246433 B2 | 4/2009 |
| JP | 2009520535 A | 5/2009 |
| JP | 2009131397 A | 6/2009 |
| JP | 4295460 B2 | 7/2009 |
| JP | 2009528905 A | 8/2009 |
| JP | 2009534157 A | 9/2009 |
| JP | 2010525896 A | 7/2010 |
| JP | 2010526609 A | 8/2010 |
| JP | 4636794 B2 | 2/2011 |
| JP | 2011509805 A | 3/2011 |
| JP | 4739223 B2 | 8/2011 |
| JP | 2012500665 A | 1/2012 |
| JP | 4904362 B2 | 3/2012 |
| JP | 4912395 B2 | 4/2012 |
| JP | 2012518446 A | 8/2012 |
| JP | 2013520260 A | 6/2013 |
| JP | 2013521884 A | 6/2013 |
| JP | 2013526388 A | 6/2013 |
| JP | 5341455 B2 | 11/2013 |
| JP | 2013540495 A | 11/2013 |
| JP | 6144009 B2 | 6/2017 |
| JP | 6449571 B2 | 1/2019 |
| PT | 1112042 E | 1/2008 |
| PT | 1259195 E | 12/2008 |
| PT | 1259193 E | 1/2011 |
| PT | 1281375 E | 3/2012 |
| PT | 1994913 E | 8/2013 |
| RU | 2149037 C1 | 5/2000 |
| SE | 7901667 L | 10/1979 |
| SU | 1271508 A1 | 11/1986 |
| SU | 1371700 A1 | 2/1988 |
| WO | WO-8402266 A1 | 6/1984 |
| WO | WO-9009102 A1 | 8/1990 |
| WO | WO-9014804 A1 | 12/1990 |
| WO | WO-9117720 A1 | 11/1991 |
| WO | WO-9203990 A1 | 3/1992 |
| WO | WO-9212690 A1 | 8/1992 |
| WO | WO-9214419 A1 | 9/1992 |
| WO | WO-9217118 A1 | 10/1992 |
| WO | WO-9301768 A1 | 2/1993 |
| WO | WO-9315693 A1 | 8/1993 |
| WO | WO-9320757 A2 | 10/1993 |
| WO | WO-9504556 A2 | 2/1995 |
| WO | WO-9504556 A3 | 4/1995 |
| WO | WO-9511055 A1 | 4/1995 |
| WO | WO-9524873 A1 | 9/1995 |
| WO | WO-9528183 A1 | 10/1995 |
| WO | WO-9528899 A1 | 11/1995 |
| WO | WO-9529640 A1 | 11/1995 |
| WO | WO-9529713 A1 | 11/1995 |
| WO | WO-9613227 A1 | 5/1996 |
| WO | WO-9614032 A1 | 5/1996 |
| WO | WO-9624306 A1 | 8/1996 |
| WO | WO-9630072 A1 | 10/1996 |
| WO | WO-9632972 A1 | 10/1996 |
| WO | WO-9635469 A1 | 11/1996 |
| WO | WO-9639962 A1 | 12/1996 |
| WO | WO-9639964 A1 | 12/1996 |
| WO | WO-9639965 A1 | 12/1996 |
| WO | WO-9640012 A1 | 12/1996 |
| WO | WO-9713463 A1 | 4/1997 |
| WO | WO-9713471 A1 | 4/1997 |
| WO | WO-9724082 A1 | 7/1997 |
| WO | WO-9727893 A1 | 8/1997 |
| WO | WO-9727897 A1 | 8/1997 |
| WO | WO-9727898 A1 | 8/1997 |
| WO | WO-9728839 A1 | 8/1997 |
| WO | WO-9732551 A1 | 9/1997 |
| WO | WO-9732615 A1 | 9/1997 |
| WO | WO-9743961 A1 | 11/1997 |
| WO | WO-9748350 A1 | 12/1997 |
| WO | WO-9803118 A1 | 1/1998 |
| WO | WO-9806356 A1 | 2/1998 |
| WO | WO-9808456 A1 | 3/1998 |
| WO | WO-9810714 A1 | 3/1998 |
| WO | WO-9811846 A1 | 3/1998 |
| WO | WO-9814137 A1 | 4/1998 |
| WO | WO-9816161 A1 | 4/1998 |
| WO | WO-9819633 A1 | 5/1998 |
| WO | WO-9824373 A1 | 6/1998 |
| WO | WO-9825533 A1 | 6/1998 |
| WO | WO-9825549 A1 | 6/1998 |
| WO | WO-9829057 A1 | 7/1998 |
| WO | WO-9836790 A1 | 8/1998 |
| WO | WO-9838916 A1 | 9/1998 |
| WO | WO-9838925 A1 | 9/1998 |
| WO | WO-9838939 A1 | 9/1998 |
| WO | WO-9838941 A1 | 9/1998 |
| WO | WO-9839038 A1 | 9/1998 |
| WO | WO-9843556 A1 | 10/1998 |
| WO | WO-9844869 A1 | 10/1998 |
| WO | WO-9846115 A2 | 10/1998 |
| WO | WO-9846119 A1 | 10/1998 |
| WO | WO-9846165 A1 | 10/1998 |
| WO | WO-9849964 A1 | 11/1998 |
| WO | WO-9850103 A1 | 11/1998 |
| WO | WO-9853759 A2 | 12/1998 |
| WO | WO-9853761 A1 | 12/1998 |
| WO | WO-9855027 A2 | 12/1998 |
| WO | WO-9855047 A1 | 12/1998 |
| WO | WO-9857590 A1 | 12/1998 |
| WO | WO-9857591 A1 | 12/1998 |
| WO | WO-9857592 A1 | 12/1998 |

(56)                    References Cited

FOREIGN PATENT DOCUMENTS

| | | |
|---|---|---|
| WO | WO-9857599 A2 | 12/1998 |
| WO | WO-9907296 A1 | 2/1999 |
| WO | WO-9908624 A1 | 2/1999 |
| WO | WO-9915112 A1 | 4/1999 |
| WO | WO-9915220 A1 | 4/1999 |
| WO | WO-9917671 A1 | 4/1999 |
| WO | WO-9917683 A1 | 4/1999 |
| WO | WO-9921490 A1 | 5/1999 |
| WO | WO-9921510 A1 | 5/1999 |
| WO | WO-9922655 A1 | 5/1999 |
| WO | WO-9922656 A1 | 5/1999 |
| WO | WO-9922658 A1 | 5/1999 |
| WO | WO-9925273 A1 | 5/1999 |
| WO | WO-9927985 A1 | 6/1999 |
| WO | WO-9933414 A1 | 7/1999 |
| WO | WO-9935977 A1 | 7/1999 |
| WO | WO-9935979 A1 | 7/1999 |
| WO | WO-9935980 A1 | 7/1999 |
| WO | WO-9936000 A1 | 7/1999 |
| WO | WO-9936001 A1 | 7/1999 |
| WO | WO-9937337 A2 | 7/1999 |
| WO | WO-9938459 A2 | 8/1999 |
| WO | WO-9940853 A1 | 8/1999 |
| WO | WO-9940868 A1 | 8/1999 |
| WO | WO-9940963 A1 | 8/1999 |
| WO | WO-9940964 A1 | 8/1999 |
| WO | WO-9942058 A1 | 8/1999 |
| WO | WO-9944524 A2 | 9/1999 |
| WO | WO-9944540 A2 | 9/1999 |
| WO | WO-9944542 A2 | 9/1999 |
| WO | WO-9947071 A1 | 9/1999 |
| WO | WO-9947075 A1 | 9/1999 |
| WO | WO-9948545 A1 | 9/1999 |
| WO | WO-9948549 A2 | 9/1999 |
| WO | WO-9949793 A1 | 10/1999 |
| WO | WO-9949910 A2 | 10/1999 |
| WO | WO-9951162 A1 | 10/1999 |
| WO | WO-9951165 A1 | 10/1999 |
| WO | WO-9953863 A1 | 10/1999 |
| WO | WO-9953987 A1 | 10/1999 |
| WO | WO-9955406 A1 | 11/1999 |
| WO | WO-9960941 A1 | 12/1999 |
| WO | WO-9962430 A1 | 12/1999 |
| WO | WO-9966863 A2 | 12/1999 |
| WO | WO-0002503 A1 | 1/2000 |
| WO | WO-0009059 A2 | 2/2000 |
| WO | WO-0009195 A1 | 2/2000 |
| WO | WO-0010623 A1 | 3/2000 |
| WO | WO-0012029 A1 | 3/2000 |
| WO | WO-0013722 A1 | 3/2000 |
| WO | WO-0015146 A1 | 3/2000 |
| WO | WO-0015147 A1 | 3/2000 |
| WO | WO-0015148 A1 | 3/2000 |
| WO | WO-0015149 A1 | 3/2000 |
| WO | WO-0015275 A2 | 3/2000 |
| WO | WO-0016848 A1 | 3/2000 |
| WO | WO-0018302 A2 | 4/2000 |
| WO | WO-0018323 A2 | 4/2000 |
| WO | WO-0018325 A1 | 4/2000 |
| WO | WO-0018326 A1 | 4/2000 |
| WO | WO-0018330 A1 | 4/2000 |
| WO | WO-0018331 A2 | 4/2000 |
| WO | WO-0018333 A1 | 4/2000 |
| WO | WO-0018445 A1 | 4/2000 |
| WO | WO-0018462 A2 | 4/2000 |
| WO | WO-0021436 A1 | 4/2000 |
| WO | WO-0021461 A2 | 4/2000 |
| WO | WO-0021463 A1 | 4/2000 |
| WO | WO-0021464 A1 | 4/2000 |
| WO | WO-0024449 A1 | 5/2000 |
| WO | WO-0025702 A1 | 5/2000 |
| WO | WO-0028922 A1 | 5/2000 |
| WO | WO-0028924 A2 | 5/2000 |
| WO | WO-0033725 A2 | 6/2000 |
| WO | WO-0035376 A1 | 6/2000 |
| WO | WO-0036997 A1 | 6/2000 |
| WO | WO-0041632 A1 | 7/2000 |
| WO | WO-0041633 A1 | 7/2000 |
| WO | WO-0041652 A1 | 7/2000 |
| WO | WO-0043051 A1 | 7/2000 |
| WO | WO-0044211 A1 | 7/2000 |
| WO | WO-0044308 A2 | 8/2000 |
| WO | WO-0044311 A2 | 8/2000 |
| WO | WO-0044313 A1 | 8/2000 |
| WO | WO-0044331 A1 | 8/2000 |
| WO | WO-0045711 A1 | 8/2000 |
| WO | WO-0045874 A1 | 8/2000 |
| WO | WO-0045886 A2 | 8/2000 |
| WO | WO-0047136 A1 | 8/2000 |
| WO | WO-0047139 A1 | 8/2000 |
| WO | WO-0048531 A1 | 8/2000 |
| WO | WO-0049952 A1 | 8/2000 |
| WO | WO-0049954 A2 | 8/2000 |
| WO | WO-0049956 A1 | 8/2000 |
| WO | WO-0049970 A1 | 8/2000 |
| WO | WO-0053122 A1 | 9/2000 |
| WO | WO-0053125 A1 | 9/2000 |
| WO | WO-0054660 A1 | 9/2000 |
| WO | WO-0054661 A1 | 9/2000 |
| WO | WO-0056224 A1 | 9/2000 |
| WO | WO-0056225 A1 | 9/2000 |
| WO | WO-0056387 A1 | 9/2000 |
| WO | WO-0060995 A2 | 10/2000 |
| WO | WO-0062714 A1 | 10/2000 |
| WO | WO-0066007 A1 | 11/2000 |
| WO | WO-0066009 A1 | 11/2000 |
| WO | WO-0066035 A1 | 11/2000 |
| WO | WO-0067661 A2 | 11/2000 |
| WO | WO-0069345 A1 | 11/2000 |
| WO | WO-0069367 A1 | 11/2000 |
| WO | WO-0069504 A1 | 11/2000 |
| WO | WO-0071195 A1 | 11/2000 |
| WO | WO-0078226 A1 | 12/2000 |
| WO | WO-0105331 A1 | 1/2001 |
| WO | WO-0106959 A1 | 2/2001 |
| WO | WO-0108566 A1 | 2/2001 |
| WO | WO-0108596 A1 | 2/2001 |
| WO | WO-0108602 A1 | 2/2001 |
| WO | WO-0110209 A1 | 2/2001 |
| WO | WO-0110320 A1 | 2/2001 |
| WO | WO-0110340 A1 | 2/2001 |
| WO | WO-0110341 A2 | 2/2001 |
| WO | WO-0110343 A1 | 2/2001 |
| WO | WO-0110347 A1 | 2/2001 |
| WO | WO-0110348 A1 | 2/2001 |
| WO | WO-0110349 A1 | 2/2001 |
| WO | WO-0110350 A1 | 2/2001 |
| WO | WO-0117440 A1 | 3/2001 |
| WO | WO-0117456 A1 | 3/2001 |
| WO | WO-0135864 A1 | 5/2001 |
| WO | WO-0135870 A1 | 5/2001 |
| WO | WO-0136870 A1 | 5/2001 |
| WO | WO-0139700 A1 | 6/2001 |
| WO | WO-0141679 A1 | 6/2001 |
| WO | WO-0149185 A1 | 7/2001 |
| WO | WO-0149187 A1 | 7/2001 |
| WO | WO-0149213 A2 | 7/2001 |
| WO | WO-0151104 A1 | 7/2001 |
| WO | WO-0154625 A1 | 8/2001 |
| WO | WO-0158503 A1 | 8/2001 |
| WO | WO-0162189 A1 | 8/2001 |
| WO | WO-0047139 A9 | 9/2001 |
| WO | WO-0164137 A1 | 9/2001 |
| WO | WO-0176510 A2 | 10/2001 |
| WO | WO-0182837 A2 | 11/2001 |
| WO | WO-0197715 A1 | 12/2001 |
| WO | WO-0211647 A2 | 2/2002 |
| WO | WO-0219926 A1 | 3/2002 |
| WO | WO-0222054 A1 | 3/2002 |
| WO | WO-0224118 A1 | 3/2002 |
| WO | WO-0236048 A1 | 5/2002 |
| WO | WO-0241789 A2 | 5/2002 |
| WO | WO-0243620 A1 | 6/2002 |
| WO | WO-0247575 A2 | 6/2002 |

(56) References Cited

FOREIGN PATENT DOCUMENTS

| | | | |
|---|---|---|---|
| WO | WO-0249540 | A2 | 6/2002 |
| WO | WO-02051489 | A2 | 7/2002 |
| WO | WO-02056798 | A2 | 7/2002 |
| WO | WO-02056955 | A1 | 7/2002 |
| WO | WO-02058745 | A1 | 8/2002 |
| WO | WO-02060509 | A1 | 8/2002 |
| WO | WO-02067782 | A2 | 9/2002 |
| WO | WO-02069842 | A2 | 9/2002 |
| WO | WO-02076349 | A1 | 10/2002 |
| WO | WO-02100297 | A2 | 12/2002 |
| WO | WO-02100301 | A1 | 12/2002 |
| WO | WO-02102286 | A1 | 12/2002 |
| WO | WO-03003943 | A2 | 1/2003 |
| WO | WO-03003949 | A2 | 1/2003 |
| WO | WO-03007795 | A2 | 1/2003 |
| WO | WO-03009785 | A1 | 2/2003 |
| WO | WO-03011195 | A2 | 2/2003 |
| WO | WO-03013239 | A2 | 2/2003 |
| WO | WO-03015851 | A1 | 2/2003 |
| WO | WO-03022183 | A1 | 3/2003 |
| WO | WO-03028592 | A1 | 4/2003 |
| WO | WO-03030776 | A2 | 4/2003 |
| WO | WO-03032869 | A1 | 4/2003 |
| WO | WO-03032870 | A1 | 4/2003 |
| WO | WO-03037222 | A2 | 5/2003 |
| WO | WO-03037227 | A2 | 5/2003 |
| WO | WO-03047460 | A2 | 6/2003 |
| WO | WO-03047468 | A1 | 6/2003 |
| WO | WO-03047648 | A2 | 6/2003 |
| WO | WO-03051231 | A2 | 6/2003 |
| WO | WO-03063729 | A2 | 8/2003 |
| WO | WO-03079928 | A2 | 10/2003 |
| WO | WO-03079932 | A2 | 10/2003 |
| WO | WO-03079933 | A1 | 10/2003 |
| WO | WO-03088873 | A1 | 10/2003 |
| WO | WO-03015851 | B1 | 11/2003 |
| WO | WO-03063729 | A3 | 11/2003 |
| WO | WO-03092554 | A1 | 11/2003 |
| WO | WO-03094793 | A1 | 11/2003 |
| WO | WO-03094797 | A1 | 11/2003 |
| WO | WO-03096932 | A1 | 11/2003 |
| WO | WO-03096935 | A1 | 11/2003 |
| WO | WO-03101195 | A1 | 12/2003 |
| WO | WO-03103949 | A1 | 12/2003 |
| WO | WO-03003949 | A3 | 1/2004 |
| WO | WO-2004004597 | A2 | 1/2004 |
| WO | WO-2004006803 | A1 | 1/2004 |
| WO | WO-2004006804 | A1 | 1/2004 |
| WO | WO-2004014256 | A1 | 2/2004 |
| WO | WO-2004016200 | A1 | 2/2004 |
| WO | WO-2004016201 | A2 | 2/2004 |
| WO | WO-2004019811 | A2 | 3/2004 |
| WO | WO-2004019817 | A1 | 3/2004 |
| WO | WO-2004019825 | A1 | 3/2004 |
| WO | WO-2004021922 | A2 | 3/2004 |
| WO | WO-2004023980 | A2 | 3/2004 |
| WO | WO-2004019811 | A9 | 4/2004 |
| WO | WO-2004026117 | A2 | 4/2004 |
| WO | WO-2004026173 | A2 | 4/2004 |
| WO | WO-2004028399 | A2 | 4/2004 |
| WO | WO-2004030515 | A2 | 4/2004 |
| WO | WO-2004041126 | A1 | 5/2004 |
| WO | WO-2004043293 | A2 | 5/2004 |
| WO | WO-2004043301 | A1 | 5/2004 |
| WO | WO-2004047681 | A1 | 6/2004 |
| WO | WO-2004058106 | A2 | 7/2004 |
| WO | WO-2004062980 | A1 | 7/2004 |
| WO | WO-2004058106 | A3 | 8/2004 |
| WO | WO-2004064671 | A2 | 8/2004 |
| WO | WO-2004066876 | A1 | 8/2004 |
| WO | WO-2004071352 | A1 | 8/2004 |
| WO | WO-2004082527 | A2 | 9/2004 |
| WO | WO-2004082528 | A2 | 9/2004 |
| WO | WO-2004082536 | A1 | 9/2004 |
| WO | WO-2004089250 | A1 | 10/2004 |
| WO | WO-2004089253 | A1 | 10/2004 |
| WO | WO-2004093728 | A2 | 11/2004 |
| WO | WO-2004096100 | A1 | 11/2004 |
| WO | WO-2004103162 | A2 | 12/2004 |
| WO | WO-2004105651 | A1 | 12/2004 |
| WO | WO-2005002466 | A2 | 1/2005 |
| WO | WO-2005004753 | A1 | 1/2005 |
| WO | WO-2005007343 | A1 | 1/2005 |
| WO | WO-2005009285 | A2 | 2/2005 |
| WO | WO-2005011534 | A1 | 2/2005 |
| WO | WO-2005011535 | A2 | 2/2005 |
| WO | WO-2005021063 | A2 | 3/2005 |
| WO | WO-2005023155 | A1 | 3/2005 |
| WO | WO-2005027790 | A1 | 3/2005 |
| WO | WO-2005027797 | A1 | 3/2005 |
| WO | WO-2005032622 | A2 | 4/2005 |
| WO | WO-2005034812 | A1 | 4/2005 |
| WO | WO-2005010215 | A3 | 5/2005 |
| WO | WO-2005046528 | A1 | 5/2005 |
| WO | WO-2005046529 | A1 | 5/2005 |
| WO | WO-2005048883 | A1 | 6/2005 |
| WO | WO-2005062980 | A2 | 7/2005 |
| WO | WO-2005063980 | A1 | 7/2005 |
| WO | WO-2005065585 | A1 | 7/2005 |
| WO | WO-2005065594 | A1 | 7/2005 |
| WO | WO-2005070343 | A1 | 8/2005 |
| WO | WO-2005072654 | A1 | 8/2005 |
| WO | WO-2005076890 | A2 | 8/2005 |
| WO | WO-2005084595 | A1 | 9/2005 |
| WO | WO-2005087140 | A1 | 9/2005 |
| WO | WO-2005096993 | A1 | 10/2005 |
| WO | WO-2005102015 | A2 | 11/2005 |
| WO | WO-2005110240 | A1 | 11/2005 |
| WO | WO-2005112779 | A1 | 12/2005 |
| WO | WO-2006005015 | A2 | 1/2006 |
| WO | WO-2006005082 | A2 | 1/2006 |
| WO | WO-2006009690 | A1 | 1/2006 |
| WO | WO-2006026371 | A1 | 3/2006 |
| WO | WO-2006027499 | A2 | 3/2006 |
| WO | WO-2005062980 | A3 | 5/2006 |
| WO | WO-2006058163 | A2 | 6/2006 |
| WO | WO-2006065949 | A2 | 6/2006 |
| WO | WO-2006066327 | A1 | 6/2006 |
| WO | WO-2006068944 | A2 | 6/2006 |
| WO | WO-2006070372 | A2 | 7/2006 |
| WO | WO-2006076890 | A1 | 7/2006 |
| WO | WO-2006083763 | A1 | 8/2006 |
| WO | WO-2006086135 | A2 | 8/2006 |
| WO | WO-2006086736 | A2 | 8/2006 |
| WO | WO-2006089517 | A1 | 8/2006 |
| WO | WO-2006093795 | A1 | 9/2006 |
| WO | WO-2006102063 | A2 | 9/2006 |
| WO | WO-2006108090 | A2 | 10/2006 |
| WO | WO-2006118766 | A1 | 11/2006 |
| WO | WO-2006124649 | A2 | 11/2006 |
| WO | WO-2006127756 | A2 | 11/2006 |
| WO | WO-2006127765 | A1 | 11/2006 |
| WO | WO-2006129441 | A1 | 12/2006 |
| WO | WO-2006132948 | A1 | 12/2006 |
| WO | WO-2006133959 | A1 | 12/2006 |
| WO | WO-2006138173 | A2 | 12/2006 |
| WO | WO-2006138391 | A2 | 12/2006 |
| WO | WO-2007009117 | A1 | 1/2007 |
| WO | WO-2007009609 | A1 | 1/2007 |
| WO | WO-2007013999 | A2 | 2/2007 |
| WO | WO-2007033093 | A2 | 3/2007 |
| WO | WO-2007035471 | A2 | 3/2007 |
| WO | WO-2005102015 | A3 | 4/2007 |
| WO | WO-2006138391 | A9 | 4/2007 |
| WO | WO-2007044285 | A2 | 4/2007 |
| WO | WO-2007047488 | A2 | 4/2007 |
| WO | WO-2007047945 | A2 | 4/2007 |
| WO | WO-2007048529 | A1 | 5/2007 |
| WO | WO-2007051620 | A1 | 5/2007 |
| WO | WO-2007053243 | A2 | 5/2007 |
| WO | WO-2007058847 | A2 | 5/2007 |
| WO | WO-2007059252 | A1 | 5/2007 |
| WO | WO-2006086736 | A3 | 6/2007 |
| WO | WO-2007071436 | A2 | 6/2007 |

(56) References Cited

FOREIGN PATENT DOCUMENTS

| WO | WO-2007092354 A2 | 8/2007 |
| WO | WO-2007097983 A2 | 8/2007 |
| WO | WO-2007098232 A2 | 8/2007 |
| WO | WO-2007053243 A3 | 9/2007 |
| WO | WO-2007120543 A1 | 10/2007 |
| WO | WO-2007071436 A3 | 11/2007 |
| WO | WO-2007123658 A1 | 11/2007 |
| WO | WO-2007123956 A2 | 11/2007 |
| WO | WO-2007127351 A1 | 11/2007 |
| WO | WO-2007127352 A1 | 11/2007 |
| WO | WO-2007033093 A3 | 1/2008 |
| WO | WO-2007071436 B1 | 1/2008 |
| WO | WO-2008028569 A1 | 3/2008 |
| WO | WO-2008031103 A2 | 3/2008 |
| WO | WO-2008035337 A2 | 3/2008 |
| WO | WO-2008040555 A2 | 4/2008 |
| WO | WO-2008045949 A2 | 4/2008 |
| WO | WO-2008047354 A2 | 4/2008 |
| WO | WO-2008051554 A2 | 5/2008 |
| WO | WO-2008070442 A1 | 6/2008 |
| WO | WO-2008070797 A2 | 6/2008 |
| WO | WO-2008079962 A1 | 7/2008 |
| WO | WO-2008098191 A2 | 8/2008 |
| WO | WO-2008100599 A1 | 8/2008 |
| WO | WO-2008101083 A2 | 8/2008 |
| WO | WO-2008118481 A2 | 10/2008 |
| WO | WO-2008125153 A1 | 10/2008 |
| WO | WO-2008137603 A2 | 11/2008 |
| WO | WO-2008138584 A1 | 11/2008 |
| WO | WO-2008150529 A1 | 12/2008 |
| WO | WO-2009002548 A1 | 12/2008 |
| WO | WO-2009024859 A2 | 2/2009 |
| WO | WO-2009029199 A1 | 3/2009 |
| WO | WO-2009042196 A2 | 4/2009 |
| WO | WO-2009045334 A1 | 4/2009 |
| WO | WO-2009045338 A1 | 4/2009 |
| WO | WO-2009053497 A1 | 4/2009 |
| WO | WO-2009054397 A1 | 4/2009 |
| WO | WO-2007044285 A3 | 5/2009 |
| WO | WO-2009061389 A2 | 5/2009 |
| WO | WO-2009085206 A2 | 7/2009 |
| WO | WO-2009091509 A1 | 7/2009 |
| WO | WO-2009094188 A2 | 7/2009 |
| WO | WO-2009094501 A1 | 7/2009 |
| WO | WO-2009100198 A2 | 8/2009 |
| WO | WO-2009106545 A1 | 9/2009 |
| WO | WO-2009108615 A1 | 9/2009 |
| WO | WO-2009111241 A2 | 9/2009 |
| WO | WO-2009137712 A1 | 11/2009 |
| WO | WO-2009149462 A2 | 12/2009 |
| WO | WO-2009155561 A2 | 12/2009 |
| WO | WO-2010022138 A2 | 2/2010 |
| WO | WO-2010042950 A2 | 4/2010 |
| WO | WO-2010043950 A2 | 4/2010 |
| WO | WO-2010044851 A1 | 4/2010 |
| WO | WO-2010045238 A2 | 4/2010 |
| WO | WO-2010045297 A2 | 4/2010 |
| WO | WO-2010049160 A1 | 5/2010 |
| WO | WO-2010083558 A1 | 7/2010 |
| WO | WO-2010086460 A1 | 8/2010 |
| WO | WO-2010098857 A1 | 9/2010 |
| WO | WO-2010104638 A2 | 9/2010 |
| WO | WO-2010045238 A3 | 10/2010 |
| WO | WO-2010141626 A2 | 12/2010 |
| WO | WO-2011008812 A2 | 1/2011 |
| WO | WO-2011008853 A2 | 1/2011 |
| WO | WO-2011035327 A1 | 3/2011 |
| WO | WO-2011051043 A1 | 5/2011 |
| WO | WO-2011057087 A1 | 5/2011 |
| WO | WO-2011060386 A2 | 5/2011 |
| WO | WO-2011102968 A1 | 8/2011 |
| WO | WO-2011102970 A1 | 8/2011 |
| WO | WO-2011104269 A1 | 9/2011 |
| WO | WO-2011120050 A1 | 9/2011 |
| WO | WO-2011126749 A1 | 10/2011 |
| WO | WO-2011133368 A1 | 10/2011 |
| WO | WO-2011144351 A2 | 11/2011 |
| WO | WO-2011147849 A1 | 12/2011 |
| WO | WO-2012002228 A1 | 1/2012 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012116368 A2 | 8/2012 |
| WO | WO-2012142189 A1 | 10/2012 |
| WO | WO-2012145546 A1 | 10/2012 |
| WO | WO-2012162228 A1 | 11/2012 |
| WO | WO-2013009975 A1 | 1/2013 |
| WO | WO-2013028387 A2 | 2/2013 |
| WO | WO-2013033791 A1 | 3/2013 |
| WO | WO-2013074671 A1 | 5/2013 |
| WO | WO-2013096545 A1 | 6/2013 |
| WO | WO-2013134214 A1 | 9/2013 |
| WO | WO-2014056644 A1 | 4/2014 |
| WO | WO-2014072439 A1 | 5/2014 |
| WO | WO-2014072439 A9 | 7/2014 |
| WO | WO-2014143126 A1 | 9/2014 |
| WO | WO-2015006139 A1 | 1/2015 |
| WO | WO-2015028209 A1 | 3/2015 |
| WO | WO-2015063118 A1 | 5/2015 |
| WO | WO-2016093877 A1 | 6/2016 |
| WO | WO-2016126511 A2 | 8/2016 |
| WO | WO-2016150806 A1 | 9/2016 |
| WO | WO-2016177562 A1 | 11/2016 |
| WO | WO-2021242607 A1 | 12/2021 |
| WO | WO-2022144741 A1 | 7/2022 |
| WO | WO-2023156879 A1 | 8/2023 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Akins C.W., et al., "Risk of Reoperative Valve Replacement for Failed Mitral and Aortic Bioprostheses," The Annals of Thoracic Surgery, 65:545-1552 (Jan. 1998). Retrieved from the Internet: URL: http://ats.ctsnetjournals.org/cgi/contenUfull/65/6/1545 (Jan. 1998).
Allen et al., "What are the characteristics of the ideal endovascular graft for abdominal aortic aneurysm exclusion?", J. Endovasc. Surg., vol. 4(2), May 1997, pp. 195-202.
Anabtawi I.N., et al., "Experimental evaluation of myocardial tunnelization as a method of myocardial revascularization," Journal of Thoracic and Cardiovascular Surgery, 58(5):638-646 (Nov. 1969).
Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.
"Aortenklappenbioprothese erfolgreich in der Entwicklung," May 16, 2003, 1 page (with English Translation).
Archie J.P., et al., "Intramyocardial Pressure: Effect of Preload on Transmural Distribution of Systolic Coronary Blood Flow," The American Journal of Cardiology, 35(6):904-911 (Jun. 1975).
Baba H., et al., "Hemodynamic effects of venous valves in aorta-coronary bypass grafts," The Journal of Thoracic and Cardiovascular Surgery, 71(5):774-778 (May 1976).
Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.
Bailey S.R., "Percutaneous Expandable Prosthetic Valves," Textbook of Interventional Cardiology, Second Edition, W.B. Saunders Company, 1994, vol. 2, pp. 1268-1276.
Block P.C., et al., "Percutaneous Approaches to Valvular Heart Disease," Current Cardiology Reports, Mar. 2005, vol. 7(2), pp. 108-113.

(56)                   References Cited

OTHER PUBLICATIONS

Blum et al., "Endoluminal Stent—Grafts for Intrarenal Abdominal Aortic Aneurysms." New Engl. J. Med., 336:13-20 (Jan. 1997).

Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.

Bonhoeffer P., et al., "Percutaneous Insertion of the Pulmonary Valve," Journal of the American College of Cardiology, May 15, 2002, vol. 39, pp. 1664-1669.

Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.

Bonhoeffer P., et al., "Technique and Results of Percutaneous Mitral Valvuloplasty With the Multi-Track System," Journal of Interventional Cadiology, 13(4):263-268 (Aug. 2000).

Bonhoeffer P., et al., "Transcatheter Implantation of a Bovine Valve in Pulmonary Position: A Lamb Study," Circulation, Aug. 15, 2000, vol. 102, pp. 813-816.

Boudjemline et al., "Percutaneous Implantation of a Biological Valve in Aortic Position: Preliminary Results in a Sheep Study," European Heart Journal, vol. 22, p. 630, Abstract Only (Sep. 2001).

Boudjemline Y., et al., "Images in Cardiovascular Medicine: Percutaneous Aortic Valve Replacement in Animals," Circulation, United States, Mar. 16, 2004, vol. 109, p. e161.

Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.

Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.

Boudjemline Y., et al., "Percutaneous Aortic Valve Replacement: Will We Get There?," Heart, British Cardiac Society, England, Dec. 2001, vol. 86, pp. 705-706.

Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.

Boudjemline Y., et al., "Percutaneous Implantation of a Valve in the Descending Aorta in Lambs," European Heart Journal, Jul. 2002, vol. 23, pp. 1045-1049.

Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.

Boudjemline Y., et al., "Percutaneous Valve Insertion: A New Approach?," Journal of Thoracic and Cardiovascular Surgery, United States, Mar. 2003, vol. 125(3), pp. 741-742.

Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.

Boudjemline Y., et al., "Steps Toward Percutaneous Aortic Valve Replacement," Circulation, Feb. 12, 2002, vol. 105, pp. 775-778.

Boudjemline Y., et al., "The Percutaneous Implantable Heart Valve," Progress in Pediatric Cardiology, Ireland, 2001, vol. 14, pp. 89-93.

Boudjemline Y., et al., "Transcatheter Reconstruction of the Right Heart," Cardiology in the Young, England, 2003, vol. 13, pp. 308-311.

Bruce C.J., et al., "Right-sided Valve Disease Deserves Little More Respect," Circulation, 119(2):2726-2734 (May 2009).

Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.

Commeau P et al., "Percutaneous Balloon Dilatation of calcific aortic Valve Stenosis: Anatomical and Haemodynamic Evaluation," British Heart Journal, 59:227-238 (Feb. 1988).

Cribier A., et al., "Percutaneous Transcatheter Implantation of an Aortic Valve Prosthesis for Calcific Aortic Stenosis: First Human Case Description," Circulation, 2002, vol. 106, pp. 3006-3008.

Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.

Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.

Cunanan et al., "Tissue Characterization and Calcification Potential of Commercial Bioprosthetic Heart Valves." Ann. Thorac. Surg., May 15, 2001, pp. S417-S421.

Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.

Dake et al., "Transluminal Placement of Endovascular Stent-Grafts for the Treatment of Descending Thoracic Aortic Aneurysms." New Engl. J. of Med., 331(26):1729-34 (Dec. 1994).

Dalby et al., "Non-Surgical Aortic Valve Replacement" Br. J. Cardiol., 10(6):450-452 (Nov. 2003).

Davidson M.J., et al., "Percutaneous Therapies for Valvular Heart Disease," Cardiovascular Pathology, Jan. 2006, vol. 15, pp. 123-129.

Dewey et al., "Transapical aortic valve implantation: An Animal Feasibility Study", The annals of thoracic surgery, 82:110-116 (Feb. 2006).

Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.

Dotter, "Transluminally-Placed Coilspring Endarterial Tube Grafts," Investigative Radiology, pp. 329-332 (Oct. 1969).

Emery et al., "Replacement of the Aortic Valve in Patients Under 50 Years of Age: Long-Term Follow-Up of the St. Jude Medical Prosthesis." Ann. Thorac. Surg., 75:1815-1819 (Jun. 2003).

European Search Report dated Aug. 10, 2011 for EP Application No. 06824992.9.

European Search Report for EP Patent Appl. Serial No. 12179049.7, dated Oct. 30, 2012, 4 pages.

European Search Report for EP Patent Appl. Serial No. 12179075.2, dated Oct. 29, 2012, 3 pages.

European Search Report for EP Patent Appl. Serial No. 12179141.2, dated Nov. 2, 2012, 3 pages.

European Search Report for EP Patent Appl. Serial No. 12179146.1, dated Nov. 7, 2012, 8 pages.

European Search Report for EP Patent Appl. Serial No. 12179330.1, dated Nov. 22, 2012, 3 pages.

European Search Report for EP Patent Appl. Serial No. 12179338.4, dated Nov. 2, 2012, 3 pages.

European Search Report for EP Patent Appl. Serial No. 12179339.2, dated Oct. 29, 2012, 4 pages.

European Search Report for EP Patent Appl. Serial No. 12179914.2, dated Nov. 7, 2012, 6 pages.

European Search Report for EP Patent Appl. Serial No. 13150337.7, dated Jul. 9, 2013, 3 pages.

European Search Report for EP Patent Appl. Serial No. 13183134.9, dated Nov. 19, 2013, 3 pages.

European Search Report for EP Patent Appl. Serial No. 14159630.4, dated May 22, 2014, 3 pages.

European Search Report for EP Patent Appl. Serial No. 14161991.6, dated Jun. 3, 2014, 3 pages.

European Search Report for EP Patent Appl. Serial No. 15167832.3, dated Jul. 23, 2015, 3 pages.

European Search Report for EP Patent Appl. Serial No. 15167847.1, dated Jul. 23, 2015, 3 pages.

European Search Report for EP Patent Appl. Serial No. 17196833.2, dated Mar. 6, 2018, 4 pages.

(56)         References Cited

OTHER PUBLICATIONS

European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Extended European Search Report dated Apr. 11, 2008 in EP Patent Appl. Serial No. 081630410, 5 pages.
Extended EP Search Report dated Sep. 24, 2020 in EP Patent Appl. Serial No. 20165841.6.
Extended European Search Report for Application No. 10183946.2.4-2320 dated Feb. 14, 2012, 7 pages.
Extended European Search Report dated Aug. 9, 2018 in EP Patent Appl. Serial No. 18158901.1.
Extended European Search Report dated Jun. 12, 2018 in EP Patent Appl. Serial No. 17209326.2.
Extended European Search Report dated 16-May 2012 in EP Patent Appl. Serial No. 11178135.7.
Extended European Search Report for Application No. 11178076.3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4,4 pages.
Extended European Search Report dated Aug. 19, 2011 in EP Patent Appl. Serial No. 07827132.7.
Extended European Search Report dated 27, Feb. 2017 in EP Patent Appl. Serial No. 16186773,6 pages.
Extended European Search Report dated 29, Sep. 2014 in EP Patent Appl. Serial No. 14164680, 5 pages.
Extended European Search Report for Application No. 07116242.4-2310 dated Mar. 31, 2008, 10 pages.
Extended European Search Report for Application No. 09154935.2, dated May 29, 2009, 7 pages.
Extended European Search Report for Application No. 10012198.7 dated Mar. 23, 2011, 7 pages.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for Application No. No. 19195062 dated Jan. 2, 2020, 7 pages.
Extended European Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.
Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.
Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.

Extended European Search Report for EP Patent Appl. Serial No. 16201320.5, dated May 19, 2017, 6 pages.
Extended European Search Report for EP Patent Appl. Serial No. 18200191.7, dated May 6, 2019, 8 pages.
Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159. (With English Translation).
Ferrari, "Entwicklung eines Verfahrens zum transvaskulären Aortenklappenersatz," Habilitationsschrift, Medizinische Fakultät der Friedrich-Schiller-Universität Jena, Sep. 2003, pp. 49-52. (With English Translation).
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
Filsoufi F., et al., "Long-term Outcomes of Tricuspid Valve Replacement in the Current Era," Ann. Thorac. Surg., 8(3):845-850 (Sep. 2005).
Fluency Vascular Stent Graft Instructions for Use, May 2014, 20 pages.
Greeenberg, "Abdominal Aortic Endografting: Fixation and Sealing." J. Am. Coll. Surg., 194(1):S79-S87 (Jan. 2002).
Grossi A.E. et al., "Impact of Minimally Invasive Valvular Heart Surgery: A Case-Control Study", Ann. Thorac. Surg., 71:807-810 (Mar. 2001).
Gummert J.F. et al., Cardiac Surgery in Germany During 2006: A Report on Behalf of the German Society for Thoracic and Cardiovascular Surgery, Thorac. Cardiov. Surg., vol. 55, (Sep. 2007), pp. 343-350.
Gummert J.F. et al., "Cardiac Surgery in Germany During 2007: A Report on Behalf of the German Society for Thoracic and Cardiovascular Surgery," Thorac. Cardiov. Surg., vol. 56, (Sep. 2008), pp. 328-336.
Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.
Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.
Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.
Hourihan M., et al., "Transcatheter Umbrella Closure of Valvular and Paravalvular Leaks", JACC, Boston, Massachusetts, 20(6):1371-1377 (Nov. 1992).
Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.
Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.
Huber C.H., et al., "Do Valved Stents Compromise Coronary Flow?," European Journal of Cardio-thoracic Surgery, Jan. 23, 2004, vol. 25, pp. 754-759.
Ing F., "Stents: What's Available to the Pediatric Interventional Cardiologist?" Catheterization and Cardiovascular Interventions, 57:374-386 (Jun. 2002).
International Search Report dated Dec. 29, 2003 in Intl PCT Patent Appl. U.S. Appl. No. PCT/DE2003/002669.
International Search Report and Written Opinion for PCT Application No. PCT/EP2009/052230 dated Jun. 29, 2009, 12 pages.
International Search Report and Written Opinion for PCT Application No. PCT/EP2010/052429 dated Jun. 14, 2010, 12 pages.
International Search Report and Written Opinion for PCT Application No. PCT/EP2011/002524 dated Apr. 23, 2012, 15 pages.
International Search Report and Written Opinion for PCT Application No. PCT/EP2011/052674 dated Jul. 5, 2011, 12 pages.
International Search Report for PCT Application No. PCT/US1999/020736 dated Jan. 28, 2000, 3 pages.

(56)            References Cited

OTHER PUBLICATIONS

International Search Report and Written Opinion for PCT Application No. PCT/EP2009/050762 dated Jun. 23, 2009, 12 pages.
International Search Report & Written Opinion mailed Jul. 18, 2016 for PCT Patent Appl No. PCT/EP2016/059839, 10 pages.
International Search Report and Written Opinion for Appl. No. PCT/EP2016/055783, mailed on May 30, 2016, 15 pages.
International Search Report and Written Opinion for Application No. PCT/EP2013/057431 dated Jul. 26, 2013, 9 pages.
International Search Report and Written Opinion for Application No. PCT/IB2018/050438 mailed Apr. 12, 2018, 11 pages.
International Search Report and Written Opinion for International Application No. PCT/EP2010/063306, dated Nov. 17, 2010, 9 pages.
International Search Report and Written Opinion for PCT Application No. PCT/EP2006/010519 dated Mar. 1, 2007, 13 pages.
International Search Report and Written Opinion for PCT Application No. PCT/US06/36286 dated Jul. 9, 2007, 4 pages.
International Search Report and Written Opinion for PCT Application No. PCT/US2004/041513 dated Jun. 10, 2005, 4 pages.
International Search Report and Written Opinion for PCT Application No. PCT/US2004/043607 dated Mar. 20, 2006, 4 pages.
International Search Report and Written Opinion for PCT Application No. PCT/US2005/020947 dated Oct. 6, 2005, 5 pages.
International Search Report and Written Opinion for PCT Application No. PCT/US2006/038352 dated May 19, 2008, 4 pages.
International Search Report and Written Opinion for PCT Application No. PCT/US2006/043484 dated Jun. 25, 2008, 4 pages.
International Search Report and Written Opinion for PCT Application No. PCT/US2007/003992 dated Jan. 10, 2008, 5 pages.
International Search Report and Written Opinion for PCT Application No. PCT/US2007/02970 dated Oct. 19, 2007, 7 pages.
International Search Report and Written Opinion for PCT Application No. PCT/US2009/060531 dated May 13, 2010, 6 pages.
International Search Report and Written Opinion for PCT/DE2006/000056 dated Jun. 7, 2006, 11 pages.
International Search Report and Written Opinion for PCT/EP2007/061117 dated May 20, 2008, 16 pages.
International Search Report and Written Opinion for PCT/EP2008/003803 dated Aug. 20, 2008, 10 pages.
International Search Report and Written Opinion for PCT/EP2009/055958 dated Oct. 21, 2009, 8 pages.
International Search Report and Written Opinion for PCT/EP2010/056558 dated Oct. 7, 2010, 14 pages.
International Search Report and Written Opinion for PCT/EP2012/067617 dated Dec. 19, 2012, 10 pages.
International Search Report and Written Opinion for PCT/IL2007/001149 dated May 1, 2008, 4 pages.
International Search Report and Written Opinion for PCT/US2011/027730 dated May 25, 2011, 9 pages.
International Search Report and Written Opinion of the International Search Authority for International Application No. PCT/EP2008/064558, date of completion of report is Mar. 18, 2009, 14 pages.
International Search Report dated Jan. 28, 2008 in Int'l PCT Application Serial No. PCT/EP2007/007413, 4 pages.
International Search Report dated Jul. 7, 2015 in Int'l PCT Application Serial No. PCT/EP2014/065817, 6 pages.
International Search Report dated Nov. 3, 2011 in Int'l PCT Application Serial No. PCT/EP2011/058506, 4 pages.
International Search Report dated Dec. 18, 2012 in Int'l PCT Patent Application Serial No. PCT/EP2012/067714, 3 pages.
International Search Report for Application No. PCT/DE2001/000837, dated Aug. 7, 2001, 4 pages.
International Search Report for Application No. PCT/EP2006/012455, mailed Sep. 27, 2007, 5 pages.
International Search Report for Application No. PCT/EP2010/057798, dated Sep. 12, 2010, 6 pages.
International Search Report for Application No. PCT/EP2011/066677, dated Feb. 17, 2012, 7 pages.
International Search Report for Application No. PCT/EP2012/067617 mailed Dec. 19, 2012, 3 pages.
International Search Report for Application No. PCT/EP2013/073318, dated Apr. 17, 2014, 5 pages.
International Search Report for Application No. PCT/EP2016/055783, mailed on May 30, 2016, 5 pages.
International Search Report for Application No. PCT/EP2016/058532, dated Jul. 11, 2016, 4 pages.
International Search Report for Application No. PCT/IB2008/002180, dated Apr. 15, 2009, 7 pages.
International Search Report for Application No. PCT/IB2018/050438 mailed Apr. 12, 2018, 3 pages.
International Search Report for PCT/DE2001/000836 dated Jun. 13, 2001, 6 pages.
International Search Report for PCT/EP2006/010023 dated Mar. 30, 2007, 6 pages.
International Search Report for PCT/IB2017/052718, dated Sep. 5, 2017, 4 pages.
Kato et al., "Traumatic Thoracic Aortic Aneurysm: Treatment with Endovascular Stent-Grafts." Radiol., 205:657-662 (Dec. 1997).
Khambadkone S., et al., "Nonsurgical Pulmonary Valve Replacement: Why, When, and How?," Catheterization and Cardiovascular Interventions, United States, Jul. 2004, vol. 62, pp. 401-408.
Khambadkone S., et al., "Percutaneous Implantation of Pulmonary Valves," Expert Review of Cardiovascular Therapy (England), Nov. 2003, vol. 1(4), pp. 541-548.
Khambadkone S., et al., "Percutaneous Pulmonary Valve Implantation: Early and Medium Term Results," Circulation, Oct. 28, 2003, vol. 108(17), p. IV-375.
Klein A.L., et al., "Age-related Prevalence of Valvular Regurgitation in Normal Subjects: A Comprehensive Color Flow Examination of 118 Volunteers," Journal of the American Society of Echocardiography, vol. 3, No. 1, (Jan. 1990), pp. 54-63.
Knudsen et al., "Catheter-implanted prosthetic heart valves", Intl J. of Art. Organs, 16(5): 253-262, May 1993.
Kort et al., "Minimally Invasive Aortic Valve Replacement: Echocardiographic and Clinical Results." Am. Heart J., Sep. 2001, vol. 142(3), pp. 476-481.
Kuzela L., et al., "Experimental evaluation of direct transventricular revascularization," Journal of Thoracic and Cardiovascular Surgery, 57(6):770-773 (Jun. 1969).
Laborde et al., "Percutaneous Implantation of the Corevalve Aortic Valve Prosthesis for Patients Presenting High Risk for Surgical Valve Replacement," EuroIntervention, 1(4): 472-474 (Feb. 2006).
Lawrence et al., "Percutaneous Endovascular Graft: Experimental Evaluation", Radiology, May 1987, vol. 163(2), pp. 357-360.
Levi et al., "Future of Interventional Cardiology in Pediactrics." Current Opinion in Cardiol., 18:79-90 (Mar. 2003).
Levy, "Mycobacterium chelonei Infection of Porcine Heart Valves." The New England Journal of Medicine, Washington DC, 297(12), Sep. 22, 1977, pp. 667-668.
Lichtenstein et al., "Transapical Transcatheter Aortic Valve Implantation in Humans: Initial Clinical Experience", circulation, American Heart Association vol. 114, Jul. 31, 2006, pp. 591-596.
Lichtenstein, S.V., "Closed heart surgery: Back to the future" The Journal of Thoracic and Cardiovascular Surgery, vol. 131(5), May 2006, pp. 941-943.
Liu et al., "Effect of Fiber Orientation on the Stress Distribution within a Leaflet of a Polymer Composite Heart Valve in be Closed Position", Journal of Biomechanics, 4:1099-1106 (Jan. 2007).
Lonescu et al., "Prevalence and Clinical Significance of Incidental Paraprosthetic Valvar Regurgitation: A prospective study using transesophageal echocardiography." Heart, 89:1316-21 (Oct. 2003).
Love S.C. et al., The Autogenous Tissue Heart Valve: Current Status, Journal of Cardiac Surgery, , Mar. 1991, vol. 6(4), pp. 499-507.
Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.
Lutter G., et al., "Percutaneous Valve Replacement: Current State and Future Prospects," Annals of Thoracic Surgery, Netherlands, Dec. 2004, vol. 78, pp. 2199-2206.

(56) References Cited

OTHER PUBLICATIONS

Ma L., et al., "Double-Crowned Valved Stents for Off-Pump Mitral Valve Replacement," European Journal of Cardio-Thoracic Surgery, Jun. 13, 2005, vol. 28(2), pp. 194-199.

Mack, M.J., "Minimally invasive cardiac surgery", Surg Endosc, 20:S488-S492 (Mar. 2006).

Magovern et al., "Twenty-five-Year Review of the Magovern-Cromie Sutureless Aortic Valve", Ann. Thorac. Surg., 48:S33-S334 (Jan. 1989).

Maraj et al., Evaluation of Hemolysis in Patients with Prosthetic Heart Valves, Clin. Cardiol. 21:387-392 (Jun. 1998).

Marcus RH et al., "Assessment of small-diameter aortic mechanical prostheses: physiological relevance of the Doppler gradient, utility of flow augmentation, and limitations of orifice area estimation," Circulation, 98(9):866-872 (Sep. 1998).

McKay G. R et al., "The Mansfield Scientific Aortic Valvuloplasty Registry: Overview of Acute Hemodynamic Results and Procedural Complications." J. Am. Coll. Cardiol., 17(2):485-491 (Feb. 1991).

Mills N.L., et al., "Valvulotomy of valves in the saphenous vein graft before coronary artery bypass," The Journal of Thoracic and Cardiovascular Surgery, 71(6):878-879 (Jun. 1976).

Mirich et al., "Percutaneously Placed Endovascular Grafts for Aortic Aneurysms: Feasibility Study", Radiology, 170:1033-1037 (Mar. 1989).

Moazami N et al. "Transluminal Aortic Valve Placement: a Fesibility Study with a Newly Designed Collapsible Aortic Valve", ASAIO Journal, vol. 42, No. 2, Mar.-Apr. 1996.

Moulopoulos et al., "Catheter-Mounted Aortic Valves," Annals of Thoracic Surg., vol. 11, No. 5, May 1971, pp. 423-430.

Munro I., et al., "The possibility of myocardial revascularization by creation of a left ventriculocoronary artery fistula," The Journal of Thoracic and Cardiovascular Surgery, 58(1):25-32 (Jul. 1969).

Nath J., et al., Impact of Tricuspid Regurgitation on Long-term Survival, Journal of the American College of Cardiology, 43(3):405-406 (Feb. 2004).

Nietlispach F., et al., "Current Balloon-Expandable Transcatheter Heart Valve and Delivery Systems", Catheterization and Cardiovascular Interventions, 75:295-300 (Sep. 2009).

Palacios I.F., "Percutaneous Valve Replacement and Repair: Fiction or Reality?," Journal of American College of Cardiology, Oct. 2004, vol. 44(8), pp. 1662-1663.

Palmaz J.C., et al., "Expandable Intrahepatic Portacaval Shunt Stents: Early Experience in the Dog," American Journal of Roentgenology, 145 (4):821-825 (Oct. 1985).

Palmaz J.C., et al., "Expandable Intrahepatic Portacaval Shunt Stents in Dogs with Chronic Portal Hypertension," American Journal of Roentgenology, 147(6):1251-1254 (Dec. 1986).

Paniagua et al., "Percutaneous Heart Valve in the Chronic in Vitro Testing Model." Circulation, Sep. 17, 2002, vol. 106: e51-e52.

Parodi J.C., et al., "Transfemoral Intraluminal Graft Implantation for Abdominal Aortic Aneurysms", Ann. Vasc. Surg., 5(6):491-499 (Nov. 1991).

Partial European Search Report dated Feb. 28, 2012 in EP Patent Appl. Serial No. 11178135.7.

Partial European Search Report for Application No. 10168525.3-1269 dated Sep. 20, 2010, 5 pages.

Partial European Search Report for Application No. 07116242.4-2310 dated Jan. 14, 2008, 5 pages.

Partial European Search Report for Application No. 11153142.2-1257 dated Apr. 4, 2011, 5 pages.

Partial European Search Report for EP Patent Appl. Serial No. 07110318.8, dated Mar. 10, 2008, 6 pages.

Partial European Search Report for EP Patent Appl. Serial No. 10163478.0, dated Nov. 2, 2010, 6 pages.

Partial International Search Report for International Application No. PCT/EP2014/055044, filed Mar. 13, 2014, 7 pages.

Paul et al., U.S. Appl. No. 12/578,463 entitled "Medical Devices and Delivery Systems for Delivering Medical Devices," filed Oct. 13, 2009, 79 pages.

Pavcnik D., et al., "Aortic and Venous Valve for Percutaneous Insertion," Minimally Invasive Therapy & Allied Technologies, Jan. 2000, vol. 9(3/4), pp. 287-292.

Pavcnik D., et al., "Development and Initial Experimental Evaluation of a Prosthetic Aortic Valve for Transcatheter Placement." Radiology, 183:151-154 (Apr. 1992).

Pavcnik et al., "Percutaneous Bioprosthetic Venous Valve: A Long-term Study in Sheep," Jounal of Vascular Surg., vol. 35, No. 3, Mar. 2002, pp. 598-603.

Pawelec-Wojtalk M., "Closure of left ventricle perforation with the use of muscular VSD occluder," European Journal of Cardia-Thoracic Surgery, 27(4):714-716 (Apr. 2005).

Pelton A.R., et al., "Medical Uses of Nitinol," Materials Science Forum, Jan. 2000, vol. 327-328, pp. 63-70.

Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.

Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.

Preliminary Search Report (Rapport De Recherche Preliminaire) dated Jul. 8, 2002 in French Patent Application No. 0110444 (2 pages).

Raillat et al., "Treatment of Iliac Artery Stenosis with the Wallstent Endoprosthesis." AJR, Mar. 1990, vol. 154(3), pp. 613-616.

Remadi et al., "Preliminary results of 130 aortic valve replacements with a new mechanical bileaflet prosthesis: The Edwards MIRA valve," Interactive Cardiovasc. and Thorac. Surg., 2:80-83 (Mar. 2003).

Rogers J.H., et al., "The Tricuspid Valve: Current Perspective and Evolving Management of Tricuspid Regurgitation," Circulation, 119(20):2718-2725 (May 2009).

Ruiz C.E., "Transcatheter Aortic Valve Implantation and Mitral Valve Repair: State of the Art," Pediatric Cardiology, Jun. 2005, vol. 26(3), pp. 289-294.

Saliba Z., et al., "Treatment of Obstructions of Prosthetic Conduits by Percutaneous Implantation of Stents," Archives Des Maladies Du Coeur Et Des Vaisseaux, May 1999, pp. 591-596.

Schurink et al., "Stent Attachment Site—related Endoleakage after Stent Graft Treatment: An in vitro study of the effects of graft size, stent type, and atherosclerotic wall changes", J. Vasc. Surg., vol. 30(4), Oct. 1999, pp. 658-667.

Search Report dated Oct. 15, 2003 from the European Patent Office for European Patent Application No. EP 02291953.4, 2 pages.

Search Report from the European Patent Office for European Patent Application No. EP 02291954.4, 4 pages, 2005.

Sochman et al., "Percutaneous Transcatheter Aortic Disc Valve Prosthesis Implantation: A Feasibility Study." Cardiovasc. Intervent. Radiol., Sep. 2000, 23: 384-388.

Stanley et al., "Evaluation of Patient Selection Guidelines for Endoluminal AAA Repair With the Zenith Stent Graft: The Australasian Experience." J. Endovasc. Ther., 8:457-464 (Oct. 2001).

Stassano P., et al., "Mid-term Results of the Valve-on-Valve Technique for Bioprosthetic Failure," European Journal of Cardiothoracic Surgery, Oct. 2000, vol. 18, pp. 453-457.

Stein D.P., et al., "Turbulent blood flow in the ascending aorta of humans with normal and diseased aortic valves", Circulation Research by American Heart Association, 39:58-65 (Jul. 1976).

Steinhoff et al., "Tissue Engineering of Pulmonary Heart Valves on Allogenic Acellular Matrix Conduits." Circulation102 [suppl. III], pp. III-50-III-55 (Nov. 2000).

Supplemental Search Report from EP Patent Office for EP Application No. 04813777.2, dated Aug. 19, 2011.

Supplemental Search Report from EP Patent Office for EP Application No. 04815634.3, dated Aug. 19, 2011.

Supplemental Search Report from EP Patent Office for EP Application No. 05758878.2, dated Oct. 24, 2011.

Supplementary European Search Report dated Jan. 2, 2012 in EP Patent Appl. Serial No. 09820051.2.

Thompson et al., "Endoluminal stent grafting of the thoracic aorta: Initial experience with the Gore Excluder," Journal of Vascular Surgery, Jun. 2002, pp. 1163-1170.

(56) References Cited

OTHER PUBLICATIONS

Topol, Eric., Textbook of Interventional Cardiology, 4th Ed; Chapter 24: "Endovascular Options For Peripheral Arterial Occlusive and Aneurysmal Disease," Saunders, pp. 499-503, 949-953 (Dec. 2003).

Triennial Review of the National Nanotechnology Initiative: "A Matter of Size", The National Academies Press, Washington DC, V-13, Retrieved from the Internet: URL: http://www.nap.edu/catalog/11752/a-matter-of-size-triennial-review-of-the-national-nanotechnology, 200 pages (Mar. 2006) (Parts 1-5).

Vahanian et al., "Percutaneous Approaches to Valvular Disease", Circulation, Apr. 6, 2004, 109: 1572-1579.

Van Herwerden et al., "Percutaneous Valve Implantation: Back to the Future?", Euro. Heart J., Sep. 2002, 23(18): 1415-1416.

Walther et al., "Transapical approach for sutureless stent-fixed aortic valve implantation: experimental results", European Journal of Cardio-thoracic Surgery 29, 703-708 (May 2006).

Webb J.G., et al., "Percutaneous Aortic Valve Implantation Retrograde from the Femoral Artery," Circulation, American Heart Association, Feb. 14, 2006, vol. 113, pp. 842-850.

Weerasinghe A., et al., "First Redo Heart Valve Replacement: A 10-Year Analysis," Circulation, 99(5):655-658 (Feb. 1999).

Weyman AB et al., "Aortic Stenosis: Physics and Physiology-What Do the Numbers Really Mean?", Rev Cardiovasc Med., 6(1):23-32 (Jan. 2005).

White et al., "Endoleak as a Complication of Endoluminal Grafting of Abdominal Aortic Aneurysms: Classification, Incidence, Diagnosis, and Management," J. Endovasc. Surg., 4:152-168 (May 1997).

Written Opinion dated Mar. 30, 2007 in Int'l PCT Application Serial No. PCT/EP2006/010023, 10 Pages.

Written Opinion dated Sep. 27, 2007 in Int'l Application No. PCT/EP2006/012455, 11 pages.

Written Opinion for Application No. PCT/EP2007/007413, mailed Jan. 28, 2008, 5 pages.

Written Opinion for Application No. PCT/EP2011/058506, mailed Nov. 3, 2011, 5 pages.

Written Opinion for Application No. PCT/EP2014/065817, mailed Jan. 7, 2015, 7 pages.

Written Opinion for PCT/EP2012/067714 dated Dec. 18, 2012, 5 Pages.

Yonga G.O., et al., "Percutaneous Transvenous Mitral Commissurotomy in Juvenile Mitral Stenosis", East African Medical Journal, 80(4):172-174 (Apr. 2003).

Yoshioka et al., "Self-Expanding Endovascular Graft: An Experimental Study in Dogs." AJR 151, Oct. 1988, pp. 673-676.

Zhou et al., "Self-expandable Valved Stent of Large Size: Off-Bypass Implantation in Pulmonary Position", Eur. J. Cardiothorac, Aug. 2003, 24: 212-216.

Cheng, et al., "Successful trans-apical aortic valve implantation for a high risk patient with aortic stenosis using a new second-generation TAVI device J-Valve system," J. of Cardiothoracic Surgery, 10(5):1-4 (2015).

EPO Communication of a Notice of Opposition in EP Patent No. 3 730 094 dated Jan. 30, 2025.

Ford, Omar, "JC Medical Becoming Serious Challenger in TAVR Fray" (May 31, 2018), available at: https://www.mddionline.com/cardiovascular/jc-medical-becoming-serious-challenger-in-tavr-fray.

International Search Report & Written Opinion dated Feb. 20, 2024 in Int'l PCT Patent Appl. Serial No. PCT/IB2023/037029.

International Search Report & Written Report Opinion dated Apr. 17, 2024 in Int'l PCT Patent Appl. Serial No. PCT/US2023/080979.

Invitation to Pay Additional Fees & Partial Search Report dated Feb. 28, 2024 in Int'l PCT Patent Appl. Serial No. PCT/US2023/080979.

Wei, et al., "A New Transcatheter Aortic Valve Replacement System for Predominant Aortic Regurgitation Implantation of the J-Valve and Early Outcome," J Am Coll Cardiol Intv., 8(14):1831-1841 (2015).

(1:2)

CATHETER SYSTEM FOR IMPLANTATION OF PROSTHETIC HEART VALVES

This application is a continuation of U.S. application Ser. No. 16/665,502, filed on Oct. 28, 2019, now U.S. Pat. No. 11,517,431, which is a continuation of U.S. application Ser. No. 15/700,366, filed on Sep. 11, 2017, now U.S. Pat. No. 10,492,906, which is a continuation of U.S. application Ser. No. 15/464,891, filed on Mar. 21, 2017, now U.S. Pat. No. 9,788,945, which is a continuation of U.S. application Ser. No. 14/168,976, filed on Jan. 30, 2014, now U.S. Pat. No. 9,775,705, which is a continuation of U.S. application Ser. No. 11/795,590, filed on Jun. 5, 2008, now U.S. Pat. No. 8,679,174, which is the national stage entry under 35 U.S.C. § 371 of PCT/DE2006/000056, filed on Jan. 12, 2006, which claims priority to German Application No. 10 2005 003 632.5, filed on Jan. 20, 2005, the entire contents of each of which are incorporated herein by reference.

The invention relates to catheters for the transvascular implantation of prosthetic heart valves with self-expanding anchoring systems, by means of which prosthetic heart valves can be implanted with minimal invasion.

It is becoming more frequently necessary for an increasing number of patients to have prosthetic heart valves implanted, for which purpose both artificial and biological implants are used for heart valve prostheses.

In the past, such operations have been conducted in such a way that it as necessary to use a heart-lung-machine on the anaesthetised patient. This therefore makes it a cost-intensive surgical intervention, which subjects the respective patients to a high degree of psychological and physical stress. The aim is to keep the lethality risk below 3%. As the age of the respective patients increases and impairment of the respective heart valves becomes more advanced, a situation is reached in which patients in need of actual treatment become inoperable. Since surgical valve replacement is not possible for these patients, they suffer from a reduce quality of life and have a considerably reduced life expectancy. Intervention would pose an extremely high risk.

These same issues also apply to operations whereby prosthetic heart valves with anchoring systems are implanted by means of so-called balloon catheters.

In a procedure of this type, incorrect positioning can occur, which can have considerable consequences for the patient, possibly leading to the death of the respective patient.

In recent times, therefore, attempts have been made to implant heart valve prostheses by means of intervention methods involving minimal invasion, whereby such prostheses are fed together with an anchoring support via the aorta of a patient and through the aorta to the heart. On reaching the implantation site at the heart, self-expansion of such anchoring supports with a heart valve prosthesis attached to them is initiated, the intended result being a reliable anchoring and exact positioning of the heart valve prosthesis. Such anchoring supports have tended to be made from shape memory alloys, such as "Nitinol" for example, and the alloy is selected so that its transition temperature is around 37° C., and self-expansion can be initiated on reaching the transition temperature.

As a result of such expansion, the anchoring support opens up so that it is able to lie against the aorta wall, where it can be securely fixed by means of additional barb elements if necessary. The heart valve prosthesis is folded open simultaneously, so that it is able to assume its function.

An anchoring support of this type incorporating a heart valve prosthesis is described in patent specification WO 2004/019825 A1, for example.

Support hoops are provided at the proximal end of such an anchoring support, which can be introduced into the pockets of a patient's heart valve, thereby enabling the anchoring support to be very accurately positioned by means of these support hoops during a surgical intervention. What are referred to as commissural hoops are provided on this anchoring support in addition, which, together with the support hoops, clamp parts of a patient's old heart valve once the anchoring support has unfolded so that the anchoring support can be reliably positioned and secured as a result of this clamping effect.

The support and commissural hoops of this known anchoring support should therefore be disposed and dimensioned so that they permit a sequential self-expansion. This means that the anchoring support is accommodated inside a cartridge for the implantation procedure. It is then fed by means of a catheter through the aorta as far as the diseased heart. On reaching the implantation site, the cartridge is manipulated so that the support hoops are released to allow them to self-expand. The cartridge is then moved and oriented together with the anchoring support so that the support hoops are introduced into the pockets of the heart valve of the respective patient. This enables exact positioning to be achieved.

The respective cartridge is then further manipulated, so that the commissural hoops are also released and able to self-expand. As this happens, the old heart valve is clamped between the support and commissural hoops and the heart valve prosthesis is opened up into its unfolded functional position.

After implanting the anchoring support incorporating the heart valve prosthesis, the catheter can then be removed from the patient's body together with the cartridge through the aorta.

Although the support hoops provided on the anchoring support can result in significantly easier and better positioning of the heart valve prosthesis to be implanted in the manner described above, there is a possibility of incorrect implantation and the heart valve prosthesis may not be capable of functioning or may be so to only an unsatisfactory degree. In certain situations, it is then no longer possible to remove a non-functioning or unsatisfactorily functioning heart valve prosthesis and it poses an increased risk of mortality for the respective patient in some cases.

The bend in the aorta in the human body during introduction through the aorta poses another problem during such surgical interventions. As the cartridge and the respective catheter are moved during this procedure, a change of direction of approximately 180° with a relatively small radius of about 50 mm has to be negotiated without causing damage to the vessel wall.

Accordingly, the objective of the invention is to reduce risk to the patient during implantation of prosthetic heart valves.

This objective is achieved by the invention on the basis of a catheter incorporating the characterising features defined in claim 1. Advantageous embodiments and designs of the invention may be obtained on the basis of the characterising features defined in the dependent claims.

In a preferred embodiment, a catheter proposed by the invention may be used in conjunction with a heart valve prosthesis with a self-expanding anchoring support of the known from patent specification WO 2004/019825 and the disclosed contents are included herein by way of reference.

This being the case, the anchoring support with the heart valve prosthesis attached to it can be temporarily accommodated inside a cartridge unit in a collapsed state during the implantation.

A cartridge unit prepared in this manner can be releasably attached to the proximal end of a guide system. The cartridge unit and guide system are minimised in term of their external diameter to the degree that they can be fed through an aorta of a patient to be operated on without any difficulty, and to this end, the total free cross-section available inside the aorta should not be completely filled.

The guide system used is sufficiently long in terms of its length for the cartridge unit to be fed with the guide system by introducing it into the groin of a patient, through the aorta as far as the patient's heart.

A flexible, bendable region is provided on the guide system, by means of which a bending radius and bending angle can be achieved that will follow and make allowance for the bend in the patient's aorta.

Elements for operating the cartridge unit are fed by means of the guide system, which has a hollow interior. These operating elements enable parts of the cartridge unit to be manipulated and moved in a specific way. For example, a radial or also lateral movement of parts of the cartridge unit can be effected by means of the operating elements. Moving parts of the cartridge unit in this specific way enables parts of the anchoring support to be released in sequence so that implantation and anchoring can take place in the manner described in WO 2004/019825.

For example, support hoops of an anchoring support can be released by a rotation or by a lateral movement in the proximal or distal direction of a part of the cartridge unit, but other parts, such as the commissural hoops for example, continue to be retained inside the cartridge unit in the collapsed state, which can subsequently be released with a-view to expansion by moving another part of the cartridge unit accordingly or by continuing the movement of the same part of the cartridge unit which previously still enabled the support hoop to be retained inside the cartridge unit in the collapsed state.

The heart valve prosthesis, which is attached to the anchoring support by stitching for example, opens simultaneously as the respective hoops of the anchoring support, to which the heart valve prosthesis is attached, expand.

In a preferred embodiment, in addition to the operating elements for parts of the cartridge unit, other operating elements are fed through the internally hollow guide system, which act on the bendable region in order to influence its curvature in a specific manner.

Due in particular to traction forces triggered via the operating elements, a specific curvature of the bendable region can be achieved during the implantation on penetrating the bend of the aorta. Tension cables or tension wires may be used as the operating elements, which are run through the internally hollow guide system as far as the proximal edge of the bendable region, where they are secured on the guide system, in which case the attacking points of the force of two such operating elements should be disposed diametrically opposite one another and in addition should be disposed at with respect to the bending axis about which the bendable region is required to curve.

For example, the curvature of the bendable region can be influenced in a specific way by applying a traction force via one of the operating elements as the guide system is pushed through the bend in the aorta by means of the bendable region and pulled out of it once the implantation has been completed.

The bendable region of a guide system may be provided in the form of a link chain, in which the individual links are connected to one another by individual joints. This being the case, the individual joints positively engage in respective adjacent links. They are designed so that a curvature of more than 180° can be maintained in the bending region, with a bending radius which guarantees that at least the radius of the bend in the aorta can be achieved.

The individual joints on the individual links of a link chain should also be disposed diametrically opposite one another in pairs on the individual links and parallel with the rotation axis of the bendable region.

The guide system used with a catheter proposed by the invention should advantageously also be designed so that a liquid coolant or a pharmaceutical preparation can be circulated through the internally hollow guide system as far as the cartridge unit. With the aid of such a liquid coolant, for example a salt solution, the anchoring support can be kept below the transition temperature of the shape memory alloy. This also prevents body fluids from being able to penetrate the interior of the guide system and a liquid pressure should therefore be maintained which lends a sufficiently high resistance to penetration by body fluid or other elements contained in body fluid.

Introducing liquid coolant in an appropriate manner can also prevent gas, for example air, from getting into the aorta and the blood.

To this end, the entire guide system should be as liquid-proof as possible. Accordingly, a flexible, bendable region provided in the form of a link chain in this instance may be sealed from the outside by means of a plastic hose to render it liquid-proof.

The parts of the cartridge unit which can be moved in a specific way in order to release hoops of the anchoring support are preferably provided in the form of sleeve-shaped elements, the internal and external diameters of which are adapted to one another so that they can engage in one another telescopically, and at least two of the sleeve-shaped elements have mutually adapted internal and external diameters such that a collapsed anchoring support with heart valve prosthesis can be accommodated between them and retained in the collapsed state.

When introducing the catheter, the cartridge unit should be completely closed as far as possible and to facilitate introduction through the aorta should have a tip at its proximal end, which is in turn preferably made from a flexible material, for example silicone.

When the cartridge unit reaches the respective patient's heart, the appropriate manipulation can then be performed, in other words parts/sleeve-shaped elements of the cartridge unit moved, so that the different hoops of the anchoring support are sequentially released and the heart valve prosthesis secured to them simultaneously opened up.

As this happens; however, the anchoring support is still securely retained on the cartridge unit. To this end, anchoring elements are provided on one sleeve-shaped element of the cartridge unit, disposed at the distal end, for example at a point where eyes are provided on the anchoring support. In this position, these anchoring elements together with the distal part of the anchoring support are also covered by a sleeve-shaped element of the cartridge unit, so that the distal part of the anchoring element is still retained in the collapsed state.

In this position, it is possible to check the function of the heart valve prosthesis, which has already unfolded. Once it is evident that the heart valve prosthesis is functioning, a further manipulation may be effected by moving the sleeve element that was previously covering the anchoring element with the distal part of the anchoring support accordingly, which causes the distal part of the anchoring support to be fully released as well so that it can then fully unfold.

If, on checking, it is found that the implanted heart valve prosthesis is not fulfilling its function or is so but not satisfactorily, it is advantageously possible to move the anchoring support together with the heart valve prosthesis back into the cartridge unit by moving the parts/sleeve-shaped elements in the opposite direction accordingly and removing all the parts, in other words the entire catheter, from the patient's body again, thereby significantly reducing the risk of the operation, after which a further attempt at implantation can be made on the same patient.

In one advantageous embodiment of the catheter proposed by the invention, a guide wire can also be run through the entire catheter. Such guide wires are already used for operations of this type and they are fed through the patient's aorta to a point behind the heart before introducing the catheter. The catheter can then be placed over the cartridge unit and guide system and into the guide wire and pushed in along it into the aorta as far as the patient's heart.

In order to monitor the process of introducing the catheter and also manipulation of the bendable region, in particular at the bend of the aorta, it is of advantage to provide marker elements on the guide system and/or the cartridge unit, made from a material which absorbs X-radiation, so that the respective position can be pinpointed on an X-ray image during the operation.

A screen filter may also be used with the catheter proposed by the invention, by means of which particles can be prevented from penetrating the respective patient's blood circulation system. Such a screen filter may be attached to the guide system so that it completely surrounds it in the radial direction. In this respect, it should be elastically biased so that it lies against the vessel wall of the aorta, thereby guaranteeing a closure that is impermeable to particles.

Furthermore, the catheter proposed by the invention may additionally be provided with a conventional balloon disposed in the interior of the guide system or cartridge unit and carried with it there or alternatively it can be fed through the interior of the guide system as far as the anchoring support to be expanded. Using such a balloon, the volume of which can be increased by means of a fluid at increased pressure, will further assist expansion of the anchoring support.

The operating elements described above, which may be fed through the interior of the guide system and provided in the form of traction and compression means, may advantageously be manipulated from a manipulating part. The manipulating part may be designed as a handle, by means of which the movement for introducing the catheter can then be effected by the respective surgeon.

Other control elements are also provided on such a manipulating part, by means of which the respective movement of the operating elements can be initiated. This being the case, it should be possible to effect the corresponding movement in as measured a manner as possible, for example with appropriate translation ratios, and it should be possible to restrict the respective movement by end stops or catch positions at least. This enables specific maximum distances or angles to be preserved, for which allowance can be made in achieving the sequential expansion of the anchoring support or the specific way in which the curvature of the bendable region is influenced. In this respect, it should be possible to adjust the end stops or individual catches as finely as possible.

All the parts of a catheter proposed by the invention but at least those which come into direct contact with the respective patient and are also introduced into the aorta should be made from bio-compatible materials which are compatible with the respective organism. It should also be possible to sterilise them, in which case it should be possible to use one of the standard sterilisation processes.

The invention will be explained in more detail on the basis examples.

Of the drawings:

FIGS. 1 to 4 are intended to illustrate and provide a clearer understanding of an example of a catheter proposed by the invention. The individual diagrams illustrate different phases which take place during implantation of an anchoring support 10 incorporating a heart valve prosthesis.

Figure 1:
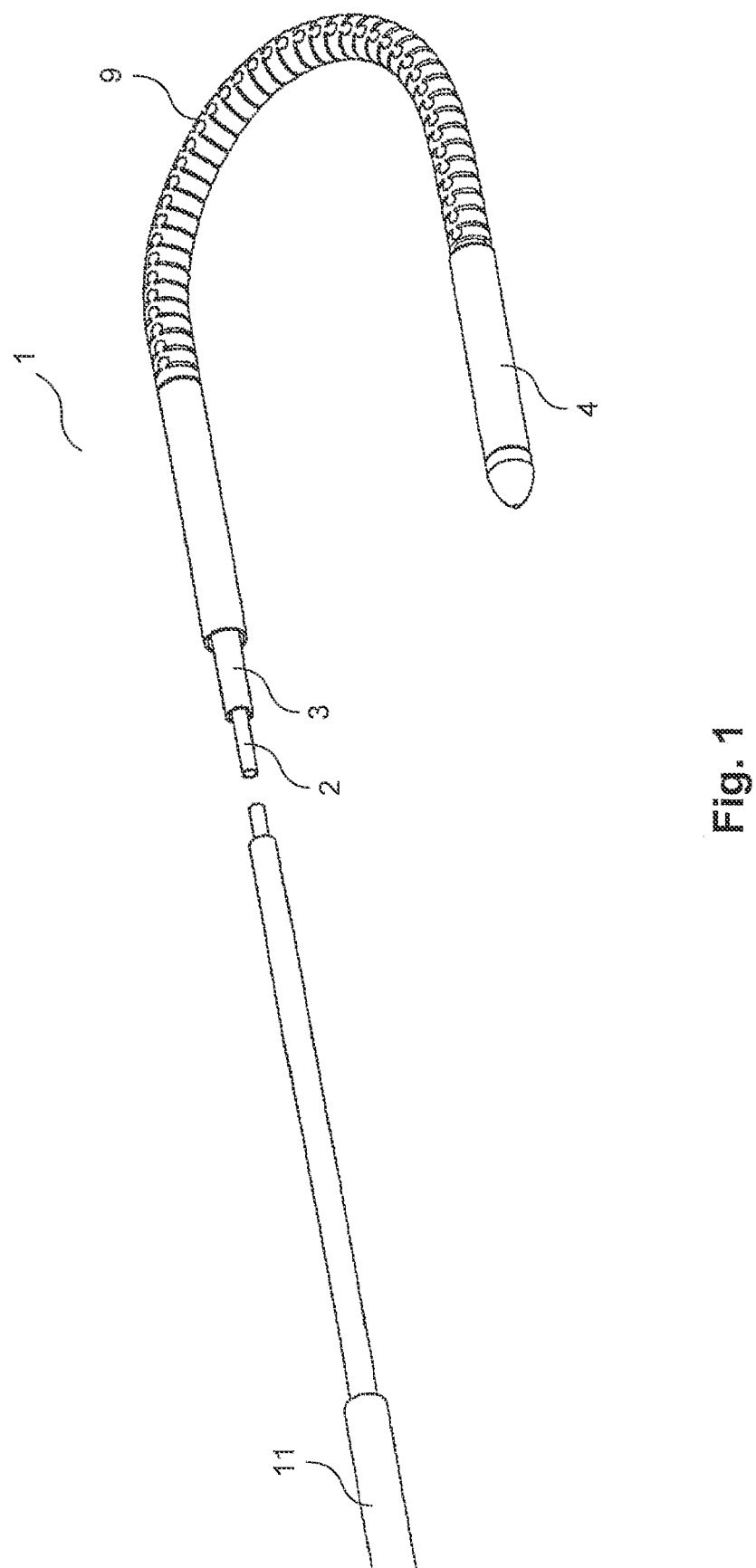
FIGS. 1 to 4 are schematic diagrams illustrating an example of a catheter proposed by the invention during different possible phases of an implantation procedure.

The example of a catheter proposed by the invention illustrated in FIG. 1 is shown with the cartridge unit 4, which is still completely closed, containing an anchoring support 10 incorporating a heart valve prosthesis in the non-expanded state and thus collapsed, so that it can be fed by means of the internally hollow guide system 1 through an appropriate access into the aorta and through it to the respective implantation site on the patient's heart.

Proximally disposed on the cartridge unit 4 is a flexible tip made from silicone, which facilitates the introduction procedure and reduces the risk of damage.

Part 5 of the cartridge unit is releasably connected to the other parts of the guide system 1, for example by means of a screw connection.

Adjoining the cartridge unit 4 is a bendable region 9, which is designed and dimensioned so that it is guaranteed to be able to move through the bend of a patient's aorta without causing problems.

Possible designs of such a bendable region 9 will be explained below.

Other parts of the internally hollow guide system 1 are also illustrated and FIGS. 1 to 4 show two operating elements 2 and 3 running through the guide system 1 as far as the cartridge unit 4, and in this instance the operating element 2 likewise runs through the internally hollow operating element 3 as far as the cartridge unit 4.

The operating elements 2 and 3 in this instance are provided in the form of lengths of compression spring, which are preferably reinforced by means of tension wire. Such tension wires make the catheter safer as it is being removed from the patient's body once the operation is complete.

Other parts 11 of the guide system 1 are illustrated on the left-hand side, which may be provided in the form of more or fewer sleeve-shaped parts, although these must be secured so that they are sufficiently pressure- and tension-resistant to withstand introduction into the aorta and extraction from the aorta again. Appropriately stiff plastic hoses may be used for this purpose, for example PTFE hoses or hoses with a PTFE base, because they are sufficiently compatible with the organism and can also be sterilised.

Figure 2:
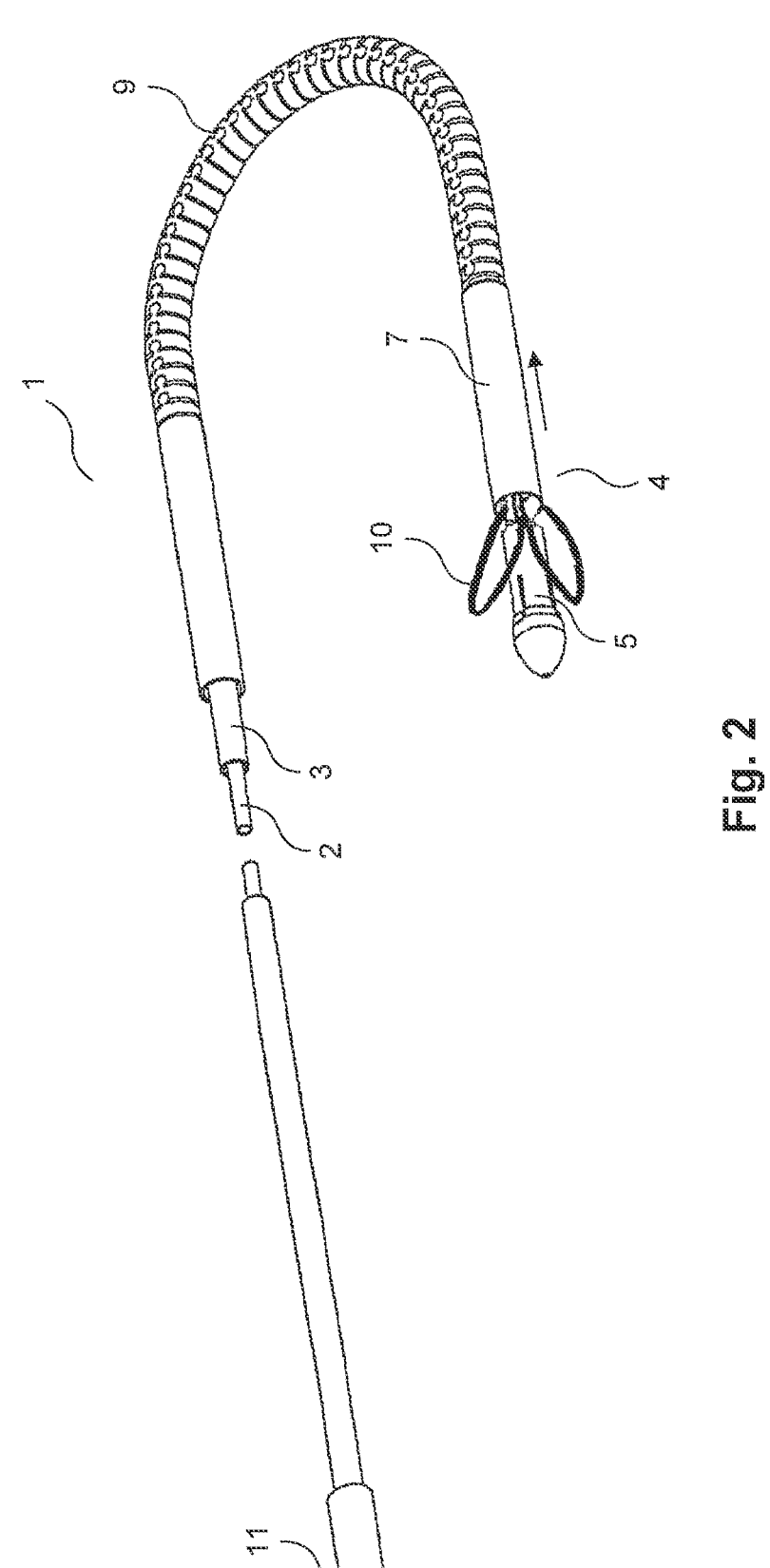

FIG. 2 illustrates the procedure which takes place during a first stage of the operation on reaching the implantation site on the respective patient's heart. The part/sleeve-shaped element 7 of the cartridge unit 4 can be pulled back in the distal direction by a distal movement of one of the operating elements 2 and/or 3 so that some hoops of the anchoring support 10, for example and preferably the support hoops provided on the known heart valve prosthesis disclosed in WO 2004/019825 A1, expand and are biased radially outwards.

The entire catheter with the guide system and the cartridge unit 4 can therefore be pushed proximally and these hoops (support hoops) introduced into the pockets of the patient's old heart valve. When the surgeon feels a perceptible resistance, the process of introducing the support hoops of the anchoring support 10 into the pockets of the old heart valve is complete.

The part/sleeve-shaped element 5 of the cartridge unit 4 can then be moved distally forwards, so that other hoops of the anchoring support can then also be released so that they can self-expand and open up the heart valve prosthesis.

Figure 3:
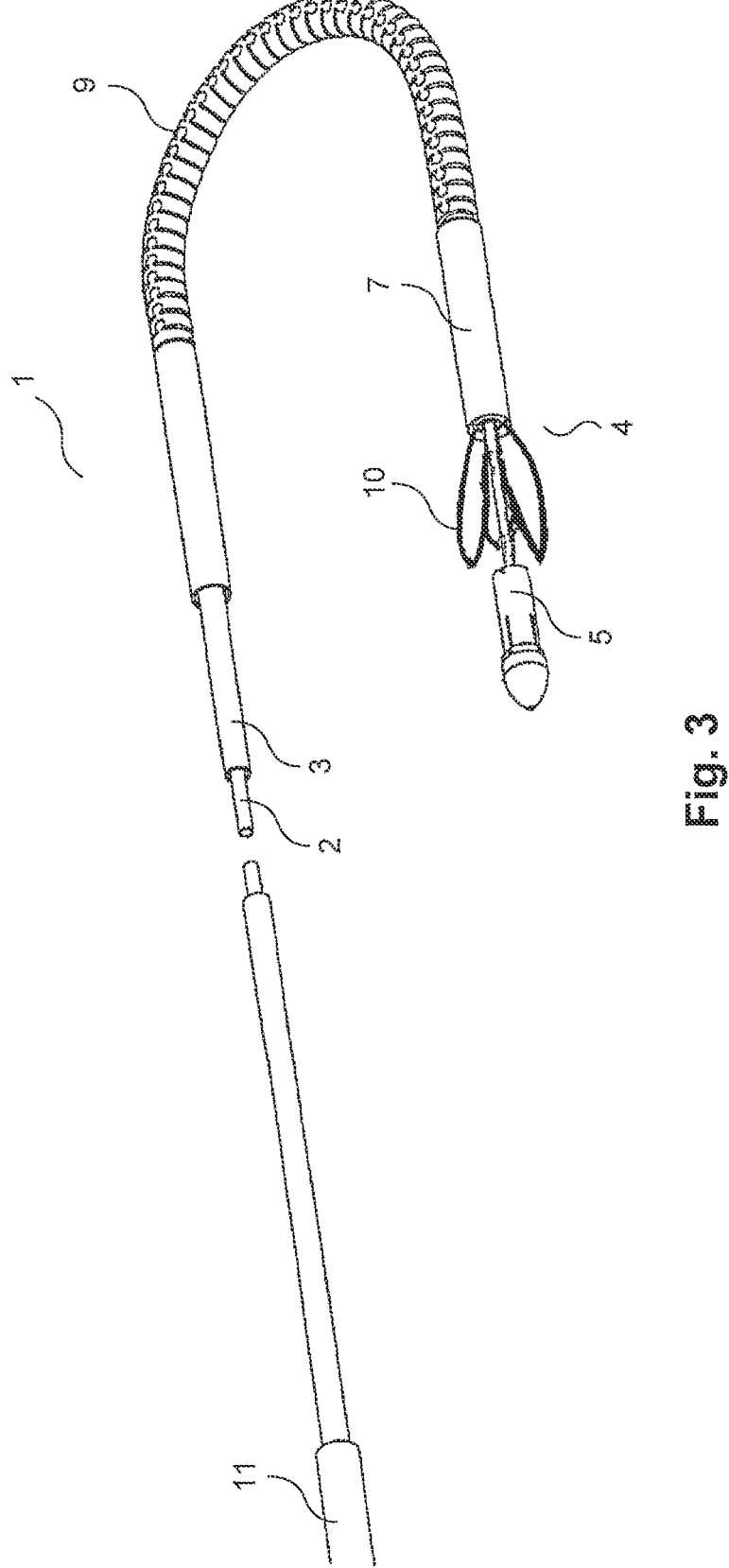

A preliminary stage of this is illustrated in FIG. 3, where a heart valve prosthesis has not yet been fully unfolded and the anchoring support 10 can also not yet be fully anchored.

As also illustrated in FIG. 3, a distal part of the anchoring support 10 is still accommodated inside the cartridge unit 4, underneath the part/sleeve-shaped element 7 in the cartridge unit 4. This remains the case until the process of unfolding and positioning the heart Valve prosthesis has reached the stage where its functionality can be checked.

If the check reveals incorrect functioning or faulty positioning, the part/sleeve-shaped element 7 can be pushed proximally again by one of the two operating elements 2 or 3 so that the anchoring support 10 with the heart valve prosthesis is at east partially accommodated in the cartridge unit 4 again and then the entire catheter can be removed from the patient by pulling it out of the aorta without causing damage to the vessel-wall.

Figure 4:
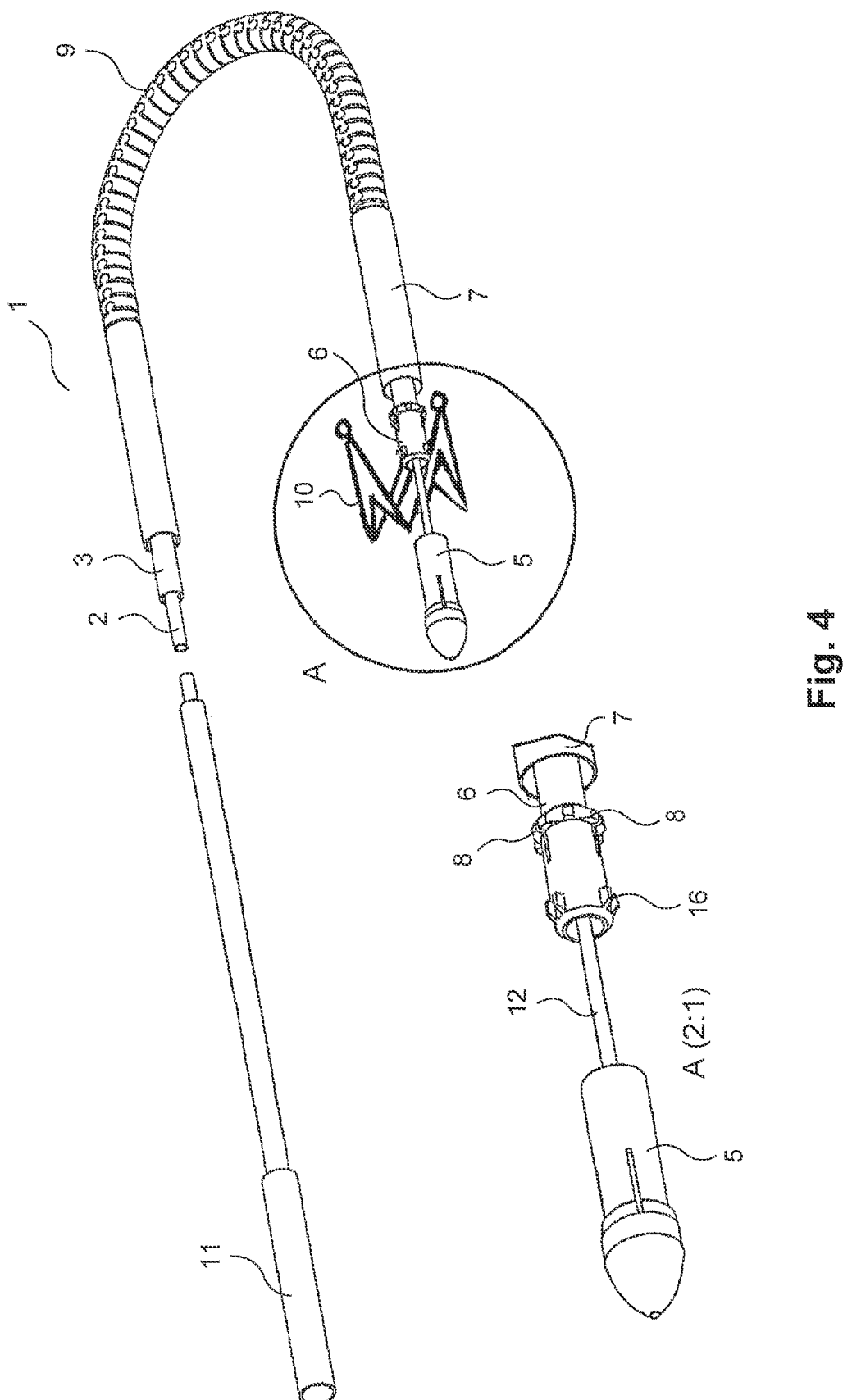

If the function test reveals that the heart valve prosthesis is able to fulfil its function to at least a sufficient capacity, the part/sleeve-shaped element 7 may be moved distally back, as illustrated in FIG. 4, or another part/sleeve-shaped element 6 of the cartridge unit 4 may be pushed in the proximal direction so that the distal part of the anchoring support 10 can also be released and expand fully.

As also illustrated in FIG. 4, eyes or other appropriate elements are provided at distal end regions of the anchoring support 10, which were previously engaged in anchoring elements 8 provided on the part/sleeve-shaped element 6. These eyes and the anchoring elements 8 ensure reliable retraction or extraction if it is established that an anchoring support 10 incorporating a heart valve prosthesis has been incorrectly or badly implanted, enabling the anchoring support 10 and heart valve prosthesis to be removed from the patient's body.

By means of the anchoring elements 8 as well as other guide elements 16 which may optionally be provided on the part/sleeve-shaped element 6 of the cartridge unit 4, it is also possible to effect a radial turning movement to enable the hoops of an anchoring support 10 to be introduced into the pockets of an old heart valve prosthesis in an exactly correct angular position, for example, in which case the entire catheter can be turned slightly about its longitudinal axis by the surgeon during the implantation.

Detail A of FIG. 4 also specifically illustrates a cannula 12, which is fed through the cartridge unit 4 along its longitudinal axis. By mans of the cannula 4, the guide wire described in the general part of the description can be fed through cartridge unit 4.

Figure 5:
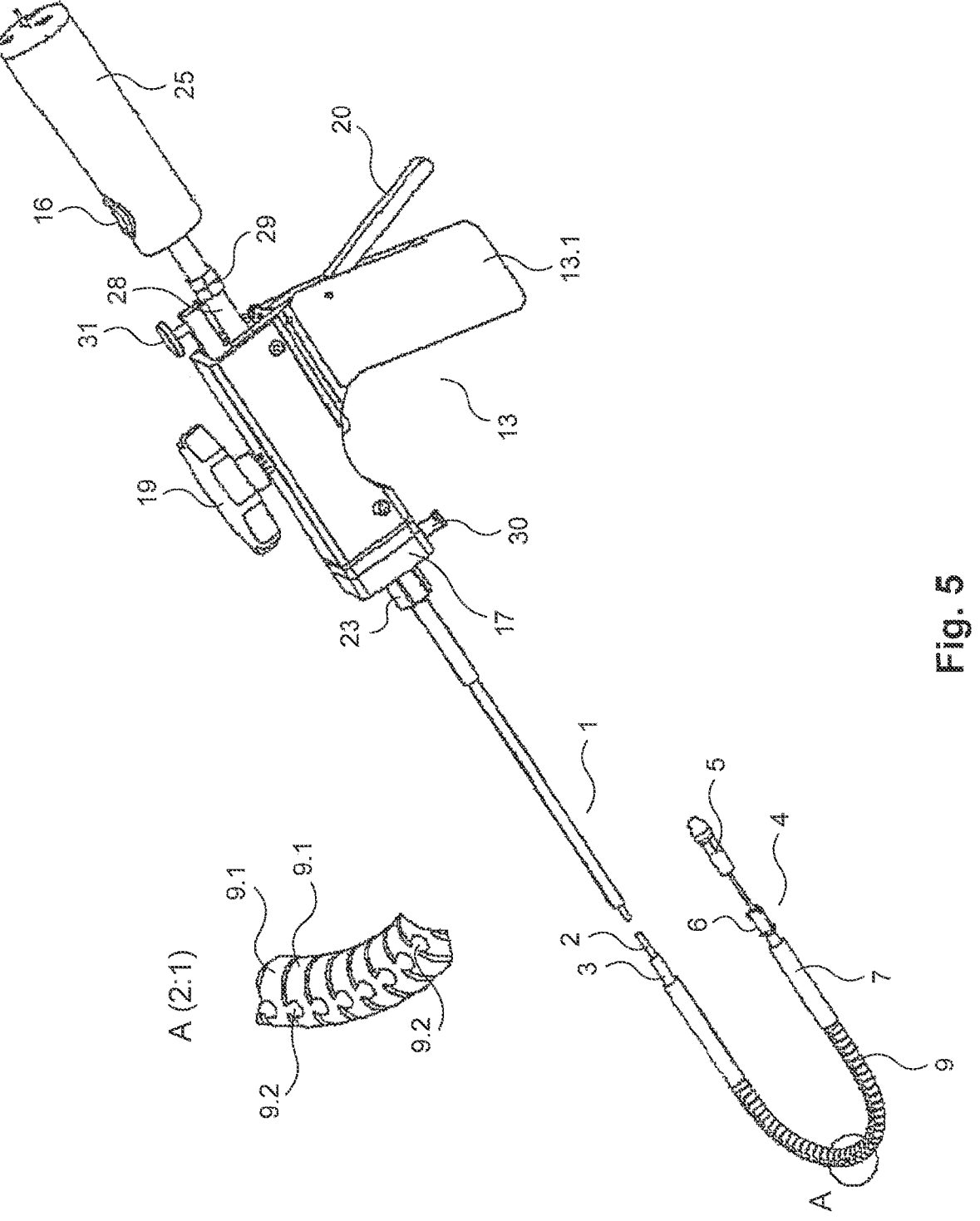
FIG. 5 shows an example of a catheter with a manipulating part.

FIG. 5 illustrates an example of a catheter with an additional manipulating part 13, on which other control elements are provided in order to permit manipulation.

The guide system 1 together with the cartridge unit 4 described above with reference to FIGS. 1 to 4 are also used in this example.

However, detail A illustrates one possible design of the bendable region 9 in the form of a link chain.

The individual links 9.1 are generally of the same shape and dimension.

In this respect, the oppositely lying end faces of the individual links 9.1 are shaped so as to form individual joints 9.2, each of which positively engages in adjacent individual links 9.1 and as a result of gaps with a sufficient gap width between the individual links 9.1 respectively ensure that the bendable region bends about at least 180° as mentioned above, with a radius of approximately 50 mm.

The individual joints 9.2 are formed by a cut-out in the respective oppositely lying end faces of the individual links 9.1, whereby a co-operating cut-out on one end face and a co-operating rounded, complementary protruding area on the diametrically opposite end face of the individual links 9.1 form the individual joints 9.2 on respective adjacent individual links 9.1.

Although not illustrated, the bendable region 9 may be enclosed by a plastic hose to render it fluid-tight.

FIG. 5 also illustrates how a manipulating part 13 may be provided to enable a catheter proposed by the invention to be introduced and manipulated.

A handle 13.1 is provided for introducing and extracting the catheter with the guide system 1 and cartridge unit 4.

A fluid-tight closure in the form of a plate 17 is provided in the proximal part of the manipulating part 13, enabling the guide system 1 to be flange-mounted by means of a locking nut 23, and seal elements are provided, although these are not illustrated here.

A standard Luer connection 30 is also provided, by means of which the coolant liquid can be circulated.

Figure 6:
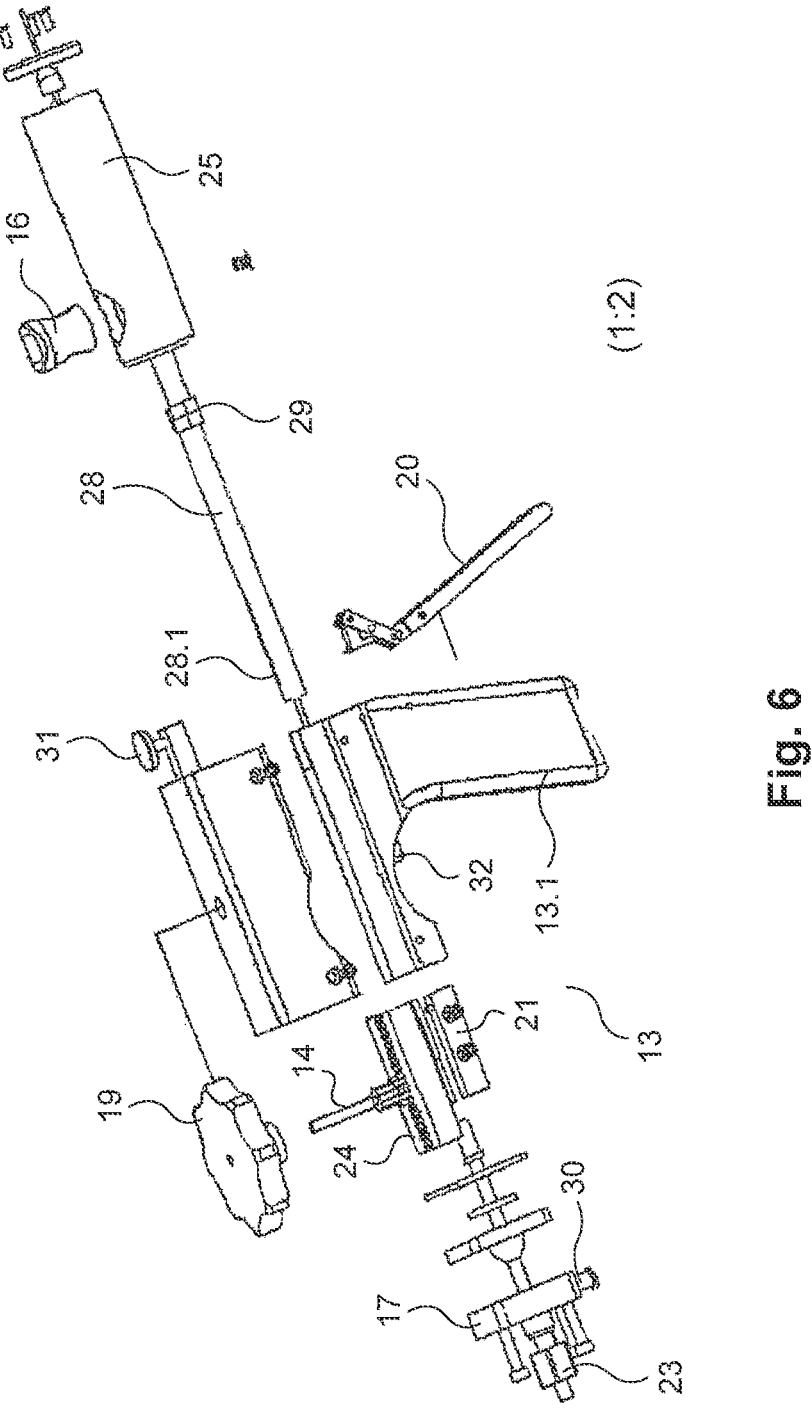
FIG. 6 is an exploded diagram illustrating the manipulating part illustrated in FIG. 5.

The respective curvature of the bendable region 9 can be obtained using the handle 19, which can be turned about an axis by means of tension cables (not illustrated) and this will be further explained with the description of FIG. 6.

The entire manipulating part 13 should be sealed with respect to the surrounding environment and with respect to the guide system 1 so that it is as far as possible fluid-tight and also gas-tight if necessary.

The tube 28 can be moved laterally in the proximal direction by means of the lever 20 acting on the handle 13.1, and the corresponding movement and resultant traction or compression force transmitted to one of the two operating elements 2 and/or 3, thereby enabling a manipulation of the individual parts/sleeve-shaped elements 5, 6 and/or 7 of the cartridge unit 4 in the manner described above, for example in finely measured doses via the pumping movements of the lever 20.

The pushing handle 25 enables the position of part 5 of the cartridge unit 4 to be manipulated relative to the sleeve-shaped part 6 of the cartridge unit 4 in the extension beyond the length of spring by means of the fixing hooks, serving as anchoring elements 8. The pushing handle 25 is latched in a thread-shaped toothing 28.1 of a tube 28 by means of a compression spring. As a result, the pushing handle 25 follows the proximal movement of the tube 28, which is connected to part 6 of the cartridge via the length of spring serving as an operating element 3.

On reaching an end stop marking the first discharge stage, the pushing handle 25 can be turned in order to effect a finely measured axial displacement of part 5 of the cartridge unit 4 relative to part 6 of the cartridge unit 4 in the direction of the pitch of the thread 28.1.

With respect to operating the pushing handle 25, the latter is able to move the part 5 of the cartridge unit 4 illustrated here without an additional fine adjustment.

Such a manipulation enables the anchoring support 10 to be released (see FIG. 3) and in this position, the anchoring support 10 can still be retracted.

When the stop 29 is released by means of an actuator member 31 provided in the form of an adjusting screw for example, the cartridge unit 4 may by extracted farther by operating the lever system 20 in the manner described above until the retaining eyes of the anchoring support 10 have moved away from the cartridge unit 4 and the anchoring support 10 is able to spring away from the anchoring elements 8 due to its expansion forces.

The elements of the cartridge unit 4 may be pulled back in stages. This being the case, part 5 of the cartridge unit 4 may be retracted by pulling back the pushing handle 25 (pushing element latched) beyond part 6 of the cartridge unit 4.

By operating a releasing bolt 32, part 6 of the cartridge unit 4 connected to the tube 28 can also be returned to its initial position by pulling the pushing handle 25 farther back so that the cartridge unit 4 is then completely closed again. In this state, the catheter can be removed from the patient's body again.

FIG. 6 is an exploded diagram providing a more detailed illustration of the manipulating part 13 used in this example.

As illustrated, when the handwheel 19 is turned via the shaft 14, two toothed racks 24 oriented parallel with one another can be displaced. Accordingly, one toothed rack 24 is moved in the proximal direction as the toothed rack 24 oriented parallel with it is moved in the distal direction.

Although these are not illustrated here, tension cables may be secured to clamping jaws 21 acting on the co-operating toothed racks 24, which are fed through the internally hollow guide system 1 as far as the bendable region 9 and are preferably secured in its proximal region.

By turning the handwheel 19 accordingly, a traction force can be applied to at least one of the two tension cables, causing the bendable region 9 to assume the appropriate curvature in measured doses so that the guide system 1 can be fed through the bend of the aorta in a defined manner together with the cartridge unit 4.

As also illustrated in FIG. 6, the lever 20 connected to the handle 13.1 acts via fine toothing 28.1 on the tube 28, enabling it to be manipulated via the operating elements and/or 3 to permit the sequential release of the anchoring support 10.

What is claimed is:

1. A catheter system for implanting a prosthetic heart valve in a patient, the catheter system comprising:
    a guide system;
    a cartridge unit disposed at a distal end of the guide system and configured to retain the prosthetic heart valve in a collapsed state, the cartridge unit comprising a first sleeve and a second sleeve configured to move with respect to the first sleeve; and
    a handle positioned at a proximal end of the guide system, the handle configured to (i) cause the cartridge unit to turn radially, and (ii) manipulate the cartridge unit to cause sequential movement of the first sleeve and the second sleeve to sequentially transition the prosthetic heart valve from the collapsed state to a partially expanded state and from the partially expanded state to a fully expanded state.

2. The catheter system of claim 1, wherein the cartridge unit further comprises a third sleeve, wherein the first sleeve is configured to be disposed within and move with respect to the third sleeve.

3. The catheter system of claim 1, wherein the first sleeve comprises at least one anchor configured to engage the prosthetic heart valve.

4. The catheter system of claim 1, wherein the handle is configured to cause both axial displacement of the second sleeve and the first sleeve and radial turning movement of the cartridge unit.

5. The catheter system of claim 1, wherein sequentially transitioning the prosthetic heart valve from the collapsed state to the partially expanded state releases anchoring supports of the prosthetic heart valve.

6. The catheter system of claim 5, wherein the handle is configured to cause the cartridge unit to turn radially to align the anchoring supports with pockets of a heart valve of the patient.

7. The catheter system of claim 1, wherein the handle comprises least one manipulator in mechanical communication with the cartridge unit.

8. The catheter system of claim 1, wherein the at least one manipulator is configured to threadedly engage the handle.

9. The catheter system of claim 1, wherein the handle further comprises a first manipulator configured to cause the guide system to bend.

10. The catheter system of claim 9, wherein the handle further comprises a second manipulator configured to cause sequential movement of the first sleeve and the second sleeve.

11. A method for implanting a prosthetic heart valve, the method comprising:
    delivering the prosthetic heart valve to an implantation site of a patient using a catheter system, the catheter system comprising a guide system, a handle positioned at a proximal end of the guide system, and a cartridge unit disposed at a distal end of the guide system and adapted to retain the prosthetic heart valve in a collapsed state, the cartridge unit comprising a first sleeve and a second sleeve adapted to move with respect to the first sleeve; and
    manipulating the handle to cause the cartridge unit to turn radially; and
    manipulating the handle to cause sequential movement of the first sleeve and second sleeve to sequentially transition the prosthetic heart valve from (i) the collapsed state to a partially expanded state and (ii) from the partially expanded state to a fully expanded state.

12. The method of claim 11, wherein the cartridge unit further comprises a third sleeve and wherein the first sleeve is disposed within the third sleeve.

13. The method of claim 12, wherein the first sleeve comprises at least one anchor adapted to engage the prosthetic heart valve, the method further comprising manipulating the handle to cause the first sleeve to move with respect to the third sleeve to disengage the prosthetic heart valve from the anchor.

14. The method of claim 11, wherein manipulating the handle to cause the cartridge unit to turn radially comprises rotating at least a portion of the handle.

15. The method of claim 11, wherein sequentially transitioning the prosthetic heart valve from the collapsed state to the partially expanded state releases anchoring supports of the prosthetic heart valve.

16. The method of claim 15, wherein manipulating the handle to cause the cartridge unit to turn radially comprises causing the cartridge unit to turn radially to align the anchoring supports with pockets of a heart valve of the patient.

17. The method of claim 11, wherein the handle comprises least one manipulator in mechanical communication with the cartridge unit.

18. The method of claim 11, wherein the handle comprises a manipulator adapted to cause the guide system to bend.

19. The method of claim 18, further comprising manipulating the manipulator to cause the guide system to bend to cause the cartridge unit to traverse an aorta of the patient.

20. The method of claim 18, wherein the handle further comprises a second manipulator adapted to cause sequential movement of the first sleeve and the second sleeve.

\* \* \* \* \*